United States Patent
Lee et al.

(10) Patent No.: US 12,215,381 B2
(45) Date of Patent: Feb. 4, 2025

(54) REPORTER AND USES THEREOF

(71) Applicant: SFC CO., LTD., Cheongju-si (KR)

(72) Inventors: Do Min Lee, Cheongju-si (KR); Ho Young Si, Cheongju-si (KR); Jae Hyung Jo, Cheongju-si (KR); Goutam Masanta, Cheongju-si (KR); Ju Man Song, Cheongju-si (KR); Min Su Eum, Cheongju-si (KR); Jong Tae Je, Cheongju-si (KR)

(73) Assignee: SFC CO., LTD., Cheongju-si (KR)

( * ) Notice: Subject to any disclaimer, the term of this patent is extended or adjusted under 35 U.S.C. 154(b) by 0 days.

(21) Appl. No.: 18/461,211

(22) Filed: Sep. 5, 2023

(65) Prior Publication Data

US 2024/0132940 A1    Apr. 25, 2024

Related U.S. Application Data

(63) Continuation of application No. PCT/KR2022/002848, filed on Feb. 28, 2022.

(30) Foreign Application Priority Data

Mar. 10, 2021 (KR) .................. 10-2021-0031308
Feb. 21, 2022 (KR) .................. 10-2022-0022318

(51) Int. Cl.
  *C09B 23/00*    (2006.01)
  *C07H 19/06*    (2006.01)
  *C12Q 1/68*     (2018.01)
  *C12Q 1/682*    (2018.01)
  *C12Q 1/6834*   (2018.01)
  *C12Q 1/686*    (2018.01)
  *G01N 21/64*    (2006.01)

(52) U.S. Cl.
  CPC ............. *C12Q 1/682* (2013.01); *C07H 19/06* (2013.01); *C09B 23/00* (2013.01); *C12Q 1/6834* (2013.01); *C12Q 1/686* (2013.01); *G01N 21/6486* (2013.01)

(58) Field of Classification Search
  CPC ...... C09B 23/00; C12Q 1/682; C12Q 1/6834; C12Q 1/686; C12Q 1/6486; C07H 19/06
  See application file for complete search history.

(56) References Cited

U.S. PATENT DOCUMENTS 5,760,201 A       6/1998   Glazer et al.
6,974,873 B2 *   12/2005   Leung .................. C07D 403/06
                                                              548/455

FOREIGN PATENT DOCUMENTS

| EP | 1209205 A1 | 5/2002 |
|---|---|---|
| KR | 10-2009-0106414 A | 10/2009 |
| KR | 10-2014-0018811 A | 2/2014 |
| KR | 10-2017-0009795 A | 1/2017 |
| KR | 10-2017-0026245 A | 3/2017 |
| KR | 10-2020-0067733 A | 6/2020 |
| WO | 2014/038561 A1 | 3/2014 |
| WO | 2016/100401 A1 | 6/2016 |
| WO | 2017/010852 A1 | 1/2017 |

OTHER PUBLICATIONS

International Search Report issued in PCT/KR2022/002848; mailed Jun. 3, 2022.
Written Opinion issued in PCT/KR2022/002848; mailed Jun. 3, 2022.
Hall, Lucy M. et al.; A highly fluorescent DNA toolkit: synthesis and properties of oligonucleotides containing new Cy3, Cy5 and Cy3B monomers; Nucleic Acids Research; Apr. 11, 2012; vol. 40; No. 14; pp. 1-10.
Richard, Jean-Alexandre; De novo synthesis of phenolic dihydroxanthene near-infrared emitting fluorophores; Organic & Biomolecular Chemistry; Jun. 29, 2015; pp. 1-4.

* cited by examiner

*Primary Examiner* — Jezia Riley
(74) *Attorney, Agent, or Firm* — Studebaker & Brackett PC

(57) ABSTRACT

The present invention relates to a fluorescent reporter capable of labeling nucleic acids including DNA and exhibiting luminescent properties at an excited energy level, and various uses thereof.

12 Claims, 5 Drawing Sheets

Specification includes a Sequence Listing.

REPORTER AND USES THEREOF

CROSS-REFERENCE TO RELATED APPLICATION

This application is based on the PCT Application No. PCT/KR2022/002848, filed on Feb. 28, 2022, and claims the benefit of priority from the prior Korean Patent Application No. 10-2021-0031308, filed on Mar. 10, 2021, and Korean Patent Application No. 10-2022-0022318, filed on Feb. 21, 2022, the disclosures of which are incorporated herein by reference in its entirety.

REFERENCE TO AN ELECTRONIC SEQUENCE LISTING

The contents of the Sequence-Listing XML (OP22-0005PCTUS_sequence listing.xml; Date of Creation: Nov. 22, 2023; and Size: 6,307 bytes) is herein incorporated by reference in its entirety.

BACKGROUND

1. Field of the Invention

The present invention relates to a fluorescent reporter capable of labeling nucleic acids including DNA and exhibiting luminescent properties at an excited energy level, and various uses thereof.

2. Discussion of Related Art

In the field of biotechnology, fluorescent dyes are used as a means for visualization to observe biological phenomena at the cellular level in vivo and in vitro, or to perform bio-imaging or examine a diseased area.

While there are self-emitting biomolecules such as a green fluorescent protein (GFP), generally, tissue or cells in the body, and lower-level biomolecules are stained with fluorescent dyes, or biomolecules such as proteins or nucleic acids are labeled with fluorescent dyes, and then imaging data is obtained by various techniques using optical equipment that is able to detect a fluorescent signal.

As mainly used optical analysis instruments, in addition to instruments for research purposes, such as a fluorescence microscope and a confocal microscope for cell observation, a flow cytometry, a microarray, a quantitative PCR system, an electrophoresis device for nucleic acid and protein separation and analysis, and a real-time in vivo imaging system, equipment for diagnosis and treatment including an in vitro diagnosis instrument based on a nucleic acid and protein diagnostic kit (or biochip), incorporating an immunoassay or PCR analysis and statistical technology, and operating tables and endoscopic equipment for medical image-guided surgery are known, and new applications and equipment with higher levels of resolution and data processing capability are continuously being developed.

To apply a fluorescent dye in the bio field, a fluorescent dye generally has less photo bleaching and quenching phenomena when present in a medium containing most biomolecules, that is, an aqueous solution, has a high molecular extinction coefficient and high quantum efficiency, and is stable under various pH conditions.

While various fluorescent dyes have been used in various research fields, those that satisfy all of the above-mentioned conditions are rare in the bio field, and currently used representative dyes include coumarin, cyanine, BODIPY, fluorescein, rhodamine, pyrene, carbopyronine, oxazine, xanthene, thioxanthene, and acridine. Among these, rhodamine derivatives and polymethine-based cyanine derivatives are particularly used.

Particularly, a cyanine-based fluorescent dye has polymethine which is connected at both ends with a nitrogen-containing heterocyclic ring and not only has the structural advantage of being able to emit various types of fluorescence across the entire visible light range of 450 to 800 nm and the near-infrared range by controlling a polymethine length but also generally has the optical property of having a very high extinction coefficient.

SUMMARY OF THE INVENTION

The present invention is directed to providing a novel reporter as a compound that can be widely used to observe the identification of biomolecules in the optical imaging field.

The present invention is also directed to providing various uses of the novel reporter defined herein, including an oligonucleotide for detecting a nucleic acid, a composition for detecting a nucleic acid, a support for detecting a nucleic acid, which include the novel reporter, and a method of detecting a nucleic acid.

Technical Solution

According to one aspect of the present invention for solving the above-mentioned technical problems, a reporter represented by Formula 1 or 2 below is provided.

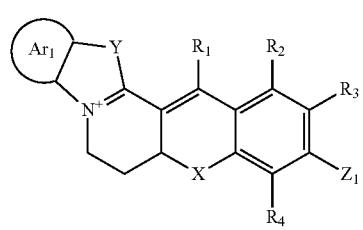

[Formula 1]

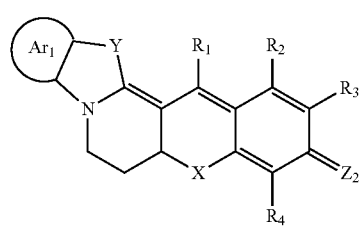

[Formula 2]

Wherein, $Ar_1$ may be substituted or unsubstituted $C_6$-$C_{20}$ aryl or $C_6$-$C_{20}$ heteroaryl containing at least one hetero atom, $Z_1$ may be $NR_5R_6$ or $OR_7$, $Z_2$ may be $NR_8$ or O, X may be O or S, Y may be $CR_9R_{10}$, $NR_{11}$, O, or S, and $R_1$ to $R_{11}$ may each be independently a functional group selected from hydrogen, deuterium, substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, substituted or unsubstituted $C_2$-$C_{20}$ heterocycloalkyl, hydroxy, oxido (—O⁻), substituted or unsubstituted $C_1$-$C_{10}$ alkoxy, substituted or unsubstituted $C_3$-$C_{20}$ cycloalkyloxy, substituted or unsubstituted $C_5$-$C_{20}$ aryloxy, substituted or unsubstituted $C_2$-$C_{20}$ heteroaryloxy, substituted or unsubstituted $C_5$-$C_{20}$ aryl, substituted or unsubstituted $C_2$-$C_{20}$ heteroaryl, substituted or unsubstituted $C_5$-$C_{20}$ aralkyl, substituted or unsubstituted $C_1$-$C_{10}$ alkylthio, substituted or unsubstituted $C_5$-$C_{20}$ arylthio, substituted or unsubstituted $C_3$-$C_{20}$ cycloalkylthio, substituted or unsubstituted $C_2$-$C_{20}$ heteroarylthio, substituted or unsubstituted acylamino, acyloxy, substituted or unsubstituted phosphino, carboxylate (—$CO_2^-$), trifluoromethylsulfonyl (—$SO_2CF_3$), substituted or unsubstituted ammonium, nitro, sulfonic acid (—$SO_3H$), sulfonate, substituted sulfonyl, substituted sulfonic acid ester, substituted or unsubstituted sulfonamide, substituted thioketone, trihalomethyl (—$CF_3$, —$CCl_3$, —$CBr_3$, or —$CI_3$), haloformyl (—COCl, —COBr, or —COI), formyl (—CHO), acyl, carboxyl, substituted ester, substituted or unsubstituted aminocarbonyl, nitro, nitroso (—N═O), fluoro (—F), chloro (—Cl), bromo (—Br), iodo (—I), substituted or unsubstituted germanium, substituted or unsubstituted boron, substituted or unsubstituted aluminum, substituted or unsubstituted silyl, substituted or unsubstituted amide, carbamate, carboxylate, substituted or unsubstituted phosphine, substituted or unsubstituted phosphoric acid, phosphate, phosphonic acid, phosphonate, nitrile, hydrazine, acetal, ketal, polyalkyleneoxide, and -$L_1$-$R_{12}$, or two adjacent functional groups are bonded to each other to form a ring.

Wherein, at least one of $R_1$ to $R_{11}$ may be -$L_1$-$R_{12}$.

$L_1$ includes a single bond or at least one selected from substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, and substituted or unsubstituted $C_2$-$C_{20}$ heterocycloalkyl, and $R_{12}$ is a deoxyribonucleoside represented by Formula 3 below.

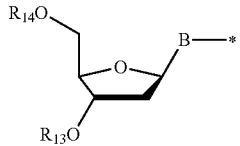

[Formula 3]

Wherein,

* indicates a location where the deoxyribonucleoside is bonded to $L_1$,

B is a nucleobase, $R_{13}$ is selected from hydrogen, deuterium, P(OR$_{15}$)(N(R$_{16}$R$_{17}$)), and -$L_2$-$R_{18}$, $R_{14}$ is an alcohol protecting group, hydroxy or P(OR$_{15}$)(N(R$_{16}$R$_{17}$)), or a support or nucleic acid to a reporter represented by Formula 1 or 2 is bound, $R_{15}$ to $R_{17}$ are each independently selected from hydrogen, deuterium, substituted or unsubstituted $C_1$-$C_{10}$ alkyl, and substituted or unsubstituted $C_1$-$C_{10}$ heteroalkyl containing at least one hetero atom, $L_2$ is a single bond, or selected from an internucleotide phosphodiester bond, substituted or unsubstituted $C_1$-$C_{10}$ alkyl and substituted or unsubstituted $C_1$-$C_{10}$ heteroalkyl containing at least one hetero atom, and $R_{18}$ is hydroxy or P(OR$_{15}$)(N(R$_{16}$R$_{17}$)), or a support or nucleic acid to which a reporter represented by Formula 1 or Formula 2 is bound.

According to another aspect of the present invention, a reporter represented by Formula 5 below is provided.

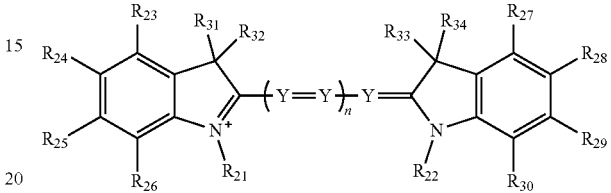

[Formula 5]

Wherein, $R_{21}$ and $R_{22}$ may each be independently selected from hydrogen, deuterium, substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, substituted or unsubstituted $C_2$-$C_{20}$ heterocycloalkyl, substituted or unsubstituted $C_5$-$C_{20}$ aryl, and substituted or unsubstituted $C_2$-$C_{20}$ heteroaryl, and $R_{23}$ to $R_{30}$ may each be independently a functional group selected from hydrogen, deuterium, substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, substituted or unsubstituted $C_2$-$C_{20}$ heterocycloalkyl, hydroxy, oxido (—O⁻), substituted or unsubstituted $C_1$-$C_{10}$ alkoxy, substituted or unsubstituted $C_3$-$C_{20}$ cycloalkyloxy, substituted or unsubstituted $C_5$-$C_{20}$ aryloxy, substituted or unsubstituted $C_2$-$C_{20}$ heteroaryloxy, substituted or unsubstituted $C_5$-$C_{20}$ aryl, substituted or unsubstituted $C_2$-$C_{20}$ heteroaryl, substituted or unsubstituted $C_5$-$C_{20}$ aralkyl, substituted or unsubstituted $C_1$-$C_{10}$ alkylthio, substituted or unsubstituted $C_5$-$C_{20}$ arylthio, substituted or unsubstituted $C_3$-$C_{20}$ cycloalkylthio, substituted or unsubstituted $C_2$-$C_{20}$ heteroarylthio, substituted or unsubstituted acylamino, acyloxy, substituted or unsubstituted phosphino, carboxylate (—$CO_2^-$), trifluoromethylsulfonyl (—$SO_2CF_3$), substituted or unsubstituted ammonium, nitro, sulfonic acid (—$SO_3H$), sulfonate, substituted sulfonyl, substituted sulfonic acid ester, substituted or unsubstituted sulfonamide, substituted thioketone, trihalomethyl (—$CF_3$, —$CCl_3$, —$CBr_3$, or —$CI_3$), haloformyl (—COCl, —COBr, or —COI), formyl (—CHO), acyl, carboxyl, substituted ester, substituted or unsubstituted aminocarbonyl, nitro, nitroso (—N═O), fluoro (—F), chloro (—Cl), bromo (—Br), iodo (—I), substituted or unsubstituted germanium, substituted or unsubstituted boron, substituted or unsubstituted aluminum, substituted or unsubstituted silyl, substituted or unsubstituted amide, carbamate, carboxylate, substituted or unsubstituted phosphine, substituted or unsubstituted phosphoric acid, phosphate, phosphonic acid, phosphonate, nitrile, hydrazine, acetal, ketal, polyalkyleneoxide, and -$L_1$-$R_{12}$, or two adjacent functional groups are bonded to each other to form a ring.

In addition, $R_{31}$ to $R_{34}$ may each be independently selected from hydrogen, deuterium, substituted or unsubstituted $C_1$-$C_{10}$ alkyl, substituted or unsubstituted $C_1$-$C_{10}$ heteroalkyl containing at least one hetero atom, and -$L_1$-$R_{12}$, and at least one of $R_{31}$ to $R_{34}$ may be -$L_1$-$R_{12}$.

$L_1$ is a single bond or at least one selected from substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, and substituted or unsubstituted $C_2$-$C_{20}$ heterocycloalkyl, and $R_{12}$ is a deoxyribonucleoside represented by Formula 3 below.

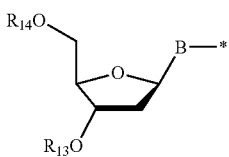

[Formula 3]

Wherein,

* indicates a location where the deoxyribonucleoside is bonded to $L_1$,

B is a nucleobase, $R_{13}$ is selected from hydrogen, deuterium, P(O$R_{15}$)(N($R_{16}R_{17}$), and -$L_2$-$R_{18}$, $R_{14}$ is an alcohol protecting group, hydroxy or P(O$R_{15}$)(N($R_{16}R_{17}$), or a support or nucleic acid to which a reporter represented by Formula 1 or 2 is bound, $R_{15}$ to $R_{17}$ are each independently selected from hydrogen, deuterium, substituted or unsubstituted $C_1$-$C_{10}$ alkyl, and substituted or unsubstituted $C_1$-$C_{10}$ heteroalkyl containing at least one hetero atom, $L_2$ is a single bond, or selected from an internucleotide phosphodiester bond, substituted or unsubstituted $C_1$-$C_{10}$ alkyl, and substituted or unsubstituted $C_1$-$C_{10}$ heteroalkyl containing at least one hetero atom, $R_{18}$ is hydroxy or P(O$R_{15}$)(N($R_{16}R_{17}$), or a support or nucleic acid to which a reporter represented by Formula 1 or 2 is bound, Y is C$R_{35}$, and each $R_{35}$ is selected from hydrogen, deuterium, substituted or unsubstituted $C_1$-$C_{10}$ alkyl, substituted or unsubstituted $C_1$-$C_{10}$ heteroalkyl containing at least one hetero atom, fluoro (—F), chloro (—Cl), bromo (—Br), and iodo (—I), and n is an integer of 1 to 4.

Specifically, the deoxyribonucleoside represented by Formula 3 may be represented by Formula 4 below.

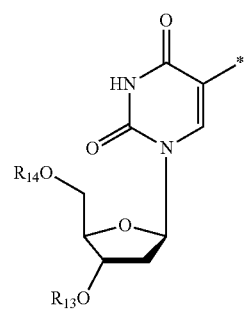

[Formula 4]

In addition, according to still another aspect of the present invention, an oligonucleotide including the reporter defined herein and a quencher is provided.

In addition, according to yet another aspect of the present invention, a composition for detecting a nucleic acid, including the oligonucleotide defined in the present invention, is provided.

In addition, according to yet another aspect of the present invention, a support for detecting a nucleic acid, which includes the reporter defined in the present invention, a support, and a linker connecting the reporter and the support, is provided.

In addition, according to yet another aspect of the present invention, a method of detecting a nucleic acid, which includes (a) preparing a reaction mixture including a target nucleic acid, a reagent required for amplifying the target nucleic acid, and the oligonucleotide defined in the present invention, (b) amplifying the target nucleic acid in the reaction mixture through polymerase chain reaction, and (c) measuring the fluorescence intensity of the reaction mixture, is provided.

A reporter according to the present invention can be effectively used to label various targets including a biomolecule due to having excellent solubility in water and excellent fluorescence intensity.

DETAILED DESCRIPTION OF EXEMPLARY EMBODIMENTS

Figure 1:
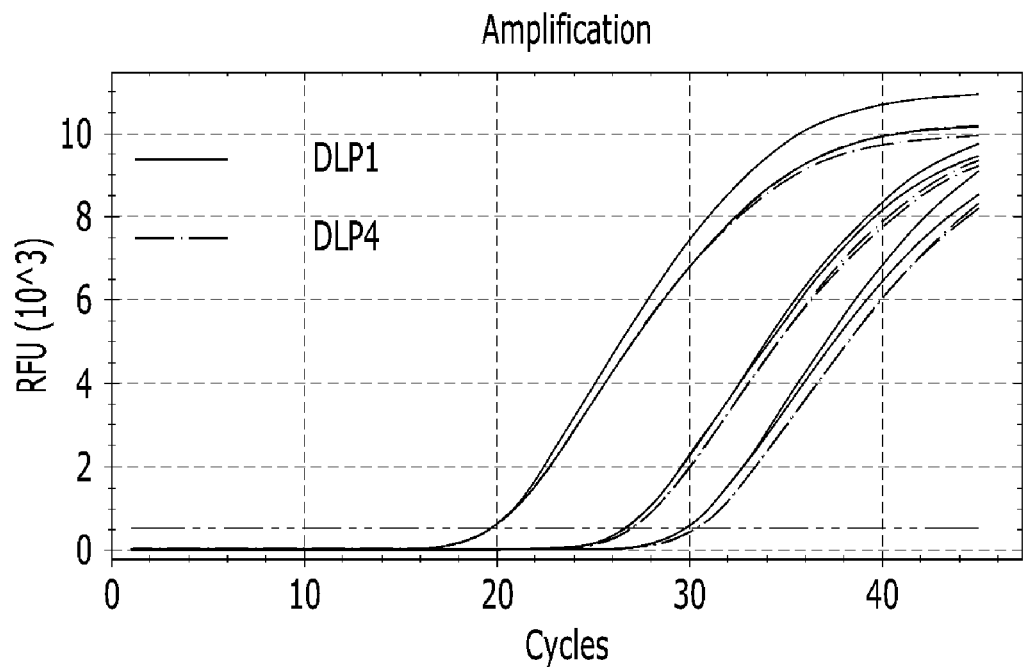
FIG. 1 is a graph showing the result of real-time PCR repeated twice on a *Chlamydia trachomatis* (CT) target sequence using a dual-labeled probe with DLP1 and DLP4.

In order to better understand the present invention, certain terms are defined herein for convenience. Unless defined otherwise herein, scientific and technical terms used herein will have meanings commonly understood by those of ordinary skill in the art.

In addition, unless specifically indicated otherwise, terms in a singular form also include plural forms, and terms in a plural form should be understood to include singular forms as well.

Novel Reporter for Labeling Nucleic Acid

According to one aspect of the present invention, a reporter for labeling a nucleic acid, represented by Formula 1 or 2 below, is provided.

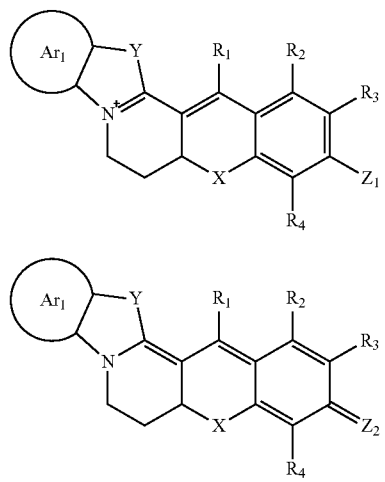

[Formula 1]

[Formula 2]

Wherein, $Ar_1$ may be substituted or unsubstituted $C_6$-$C_{20}$ aryl or $C_6$-$C_{20}$ heteroaryl containing at least one hetero atom, $Z_1$ may be $NR_5R_6$ or $OR_7$, $Z_2$ may be $NR_8$ or O, X may be O or S, Y may be $CR_9R_{10}$, $NR_{11}$, O, or S, and $R_1$ to $R_{11}$ may each be independently a functional group selected from hydrogen, deuterium, substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, substituted or unsubstituted $C_2$-$C_{20}$ heterocycloalkyl, hydroxy, oxido (—$O^-$), substituted or unsubstituted $C_1$-$C_{10}$ alkoxy, substituted or unsubstituted $C_3$-$C_{20}$ cycloalkyloxy, substituted or unsubstituted $C_5$-$C_{20}$ aryloxy, substituted or unsubstituted $C_2$-$C_{20}$ heteroaryloxy, substituted or unsubstituted $C_5$-$C_{20}$ aryl, substituted or unsubstituted $C_2$-$C_{20}$ heteroaryl, substituted or unsubstituted $C_5$-$C_{20}$ aralkyl, substituted or unsubstituted $C_1$-$C_{10}$ alkylthio, substituted or unsubstituted $C_5$-$C_{20}$ arylthio, substituted or unsubstituted $C_3$-$C_{20}$ cycloalkylthio, substituted or unsubstituted $C_2$-$C_{20}$ heteroarylthio, substituted or unsubstituted acylamino, acyloxy, substituted or unsubstituted phosphino, carboxylate (—$CO_2^-$), trifluoromethylsulfonyl (—$SO_2CF_3$), substituted or unsubstituted ammonium, nitro, sulfonic acid (—$SO_3H$), sulfonate, substituted sulfonyl, substituted sulfonic acid ester, substituted or unsubstituted sulfonamide, substituted thioketone, trihalomethyl (—$CF_3$, —$CCl_3$, —$CBr_3$, or —$CI_3$), haloformyl (—COCl, —COBr, or —COI), formyl (—CHO), acyl, carboxyl, substituted ester, substituted or unsubstituted aminocarbonyl, nitro, nitroso (—N=O), fluoro (—F), chloro (—Cl), bromo (—Br), iodo (—I), substituted or unsubstituted germanium, substituted or unsubstituted boron, substituted or unsubstituted aluminum, substituted or unsubstituted silyl, substituted or unsubstituted amide, carbamate, carboxylate, substituted or unsubstituted phosphine, substituted or unsubstituted phosphoric acid, phosphate, phosphonic acid, phosphonate, nitrile, hydrazine, acetal, ketal, polyalkyleneoxide, and -$L_1$-$R_{12}$, or two adjacent functional groups are bonded to each other to form a ring.

In addition, when any functional group of $R_1$ to $R_{11}$ is a substituted functional group, any substituent other than hydrogen may be bonded to at least one carbon in the functional group. The substituent may be selected from deuterium, substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, substituted or unsubstituted $C_2$-$C_{20}$ heterocycloalkyl, hydroxy, oxido (—$O^-$), substituted or unsubstituted $C_1$-$C_{10}$ alkoxy, substituted or unsubstituted $C_3$-$C_{20}$ cycloalkyloxy, substituted or unsubstituted $C_5$-$C_{20}$ aryloxy, substituted or unsubstituted $C_2$-$C_{20}$ heteroaryloxy, substituted or unsubstituted $C_5$-$C_{20}$ aryl, substituted or unsubstituted $C_2$-$C_{20}$ heteroaryl, substituted or unsubstituted $C_5$-$C_{20}$ aralkyl, substituted or unsubstituted $C_1$-$C_{10}$ alkylthio, substituted or unsubstituted $C_5$-$C_{20}$ arylthio, substituted or unsubstituted $C_3$-$C_{20}$ cycloalkylthio, substituted or unsubstituted $C_2$-$C_{20}$ heteroarylthio, substituted or unsubstituted acylamino, acyloxy, substituted or unsubstituted phosphino, carboxylate (—$CO_2^-$), trifluoromethylsulfonyl (—$SO_2CF_3$), substituted or unsubstituted ammonium, nitro, sulfonic acid (—$SO_3H$), sulfate, substituted sulfonyl, substituted sulfonic acid ester, substituted or unsubstituted sulfonamide, substituted thioketone, trihalomethyl (—$CF_3$, —$CCl_3$, —$CBr_3$, or —$CI_3$), haloformyl (—COCl, —COBr, or —COI), formyl (—CHO), acyl, carboxyl, substituted ester, substituted or unsubstituted aminocarbonyl, nitro, nitroso (—N=O), fluoro (—F), chloro (—Cl), bromo (—Br), iodo (—I), substituted or unsubstituted germanium, substituted or unsubstituted boron, substituted or unsubstituted aluminum, substituted or unsubstituted silyl, substituted or unsubstituted amide, carbamate, carboxylate, substituted or unsubstituted phosphine, substituted or unsubstituted phosphoric acid, phosphate, phosphonic acid, phosphonate, nitrile, hydrazine, acetal, ketal, polyalkyleneoxide, and -$L_1$-$R_{12}$.

In reporters according to various embodiments of the present invention, at least one of $R_1$ to $R_{11}$ has a functional group represented by -$L_1$-$R_{12}$, and the reporters may bond to and label a target biomolecule (e.g., a nucleic acid) via a functional group represented by -$L_1$-$R_{12}$.

According to one embodiment, in the reporter represented by Formula 1 or 2, Y may be $CR_9R_{10}$, and at least one of $R_9$ and $R_{10}$ may be -$L_1$-$R_{12}$.

$L_1$ is a linker connecting a main body represented by Formula 1 or 2 and $R_{12}$, and may be a single bond (i.e., there is no element or functional group between the main body represented by Formula 1 or 2 and $R_{12}$), or at least one selected from a saturated or unsaturated, substituted or unsubstituted, or branched or unbranched alkyl, heteroalkyl, alkenyl, alkynyl, cycloalkyl, cycloalkenyl, and heterocycloalkyl. For example, when $L_1$ is not a single bond, $L_1$ may include (1) substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, or substituted or unsubstituted $C_2$-$C_{20}$ heterocycloalkyl, or (2) at least one selected from substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, and substituted or unsubstituted $C_2$-$C_{20}$ heterocycloalkyl.

In addition, $L_1$ is a linker including at least one carbon, which is mentioned above, and any carbon of the linker may be a carbonyl carbon. The carbonyl may be at least one selected from aldehydes, ketones, carboxylic acids, esters, amides, enones, acyl halides, acid anhydrides, and imides.

In another case, $L_1$ may have a structure in which neighboring linkers are interconnected via a carbonyl carbon. Wherein, $L_1$ may include both a linker directly connected without a carbonyl carbon and a linker connected by a carbonyl carbon. For example, $L_1$ may have a structure including an amide (aminocarbonyl), such as "—$CH_2$—$CH_2$—C(=O)—NH—$CH_2$—$CH_2$—CH—$CH_2$—." In addition, $L_1$ may have a structure including a carbonylamino, such as "—$CH_2$—$CH_2$—NH—C(=O)—$CH_2$—$CH_2$—CH=CH—$CH_2$—."

$R_{12}$ is a deoxyribonucleoside represented by Formula 3.

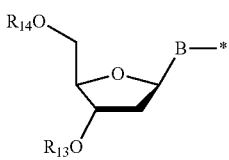

[Formula 3]

Wherein,
* indicates a location where the deoxyribonucleoside is bonded to $L_1$,
B is a nucleobase. As a component of the deoxyribonucleoside represented by Formula 3, the nucleobase may be a purine-based base such as adenine, guanine, hypoxanthine, xanthine, or 7-methylguanine; or a pyrimidine-based base such as cytosine, thymine, uracil, 5,6-dihydrouracil, 5-methylcytosine, or 5-hydroxymethylcytosine.

As the nucleobase, a deoxyribonucleoside including thymine (thymidine) may be represented by Formula 4 below.

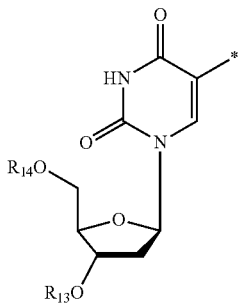

[Formula 4]

In the deoxyribonucleoside represented by Formula 3 or 4, $R_{13}$ may be selected from hydrogen, deuterium, P(OR$_{15}$)(N(R$_{16}$R$_{17}$), and -$L_2$-$R_{18}$, and $R_{14}$ may be an alcohol protecting group, hydroxy, or P(OR$_{15}$)(N(R$_{16}$R$_{17}$), or a support or nucleic acid to which the reporter represented by Formula 1 or 2 is bound.

When $R_{13}$ or $R_{14}$ is P(OR$_{15}$)(N(R$_{16}$R$_{17}$), $R_{15}$ to $R_{17}$ may each be independently selected from hydrogen, deuterium, substituted or unsubstituted $C_1$-$C_{10}$ alkyl, and substituted or unsubstituted $C_1$-$C_{10}$ heteroalkyl containing at least one hetero atom.

In addition, when any functional group in $R_{15}$ to $R_{17}$ is a substituted functional group, any substituent other than hydrogen may be bonded to at least one carbon of the functional group. The substituent may be selected from deuterium, substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, substituted or unsubstituted $C_2$-$C_{20}$ heterocycloalkyl, hydroxy, oxido (—O$^-$), substituted or unsubstituted $C_1$-$C_{10}$ alkoxy, substituted or unsubstituted $C_3$-$C_{20}$ cycloalkyloxy, substituted or unsubstituted $C_5$-$C_{20}$ aryloxy, substituted or unsubstituted $C_2$-$C_{20}$ heteroaryloxy, substituted or unsubstituted $C_5$-$C_{20}$ aryl, substituted or unsubstituted $C_2$-$C_{20}$ heteroaryl, substituted or unsubstituted $C_5$-$C_{20}$ aralkyl, substituted or unsubstituted $C_1$-$C_{10}$ alkylthio, substituted or unsubstituted $C_5$-$C_{20}$ arylthio, substituted or unsubstituted $C_3$-$C_{20}$ cycloalkylthio, substituted or unsubstituted $C_2$-$C_{20}$ heteroarylthio, substituted or unsubstituted acylamino, acyloxy, substituted or unsubstituted phosphino, carboxylate (—$CO_2^-$), trifluoromethylsulfonyl (—$SO_2CF_3$), substituted or unsubstituted ammonium, nitro, sulfonic acid (—$SO_3H$), sulfate, substituted sulfonyl, substituted sulfonic acid ester, substituted or unsubstituted sulfonamide, substituted thioketone, trihalomethyl (—$CF_3$, —$CCl_3$, —$CBr_3$, or —$CI_3$), haloformyl (—COCl, —COBr, or —COI), formyl (—CHO), acyl, carboxyl, substituted ester, substituted or unsubstituted aminocarbonyl, nitro, nitroso (—N=O), fluoro (—F), chloro (—Cl), bromo (—Br), iodo (—I), substituted or unsubstituted germanium, substituted or unsubstituted boron, substituted or unsubstituted aluminum, substituted or unsubstituted silyl, substituted or unsubstituted amide, carbamate, carboxylate, substituted or unsubstituted phosphine, substituted or unsubstituted phosphoric acid, phosphate, phosphonic acid, phosphonate, nitrile, hydrazine, acetal, ketal, polyalkyleneoxide, and -$L_1$-$R_{12}$.

When $R_{13}$ is -$L_2$-$R_{18}$, $L_2$ is a linker connecting O with $R_{18}$, and may be a single bond (i.e., there is no element or functional group between O and $R_{18}$), an internucleotide phosphodiester bond, or a saturated or unsaturated, substituted or unsubstituted, or branched or unbranched alkyl or heteroalkyl.

For example, when $L_2$ is neither a single bond nor an internucleotide phosphodiester bond, $L_2$ may be substituted or unsubstituted $C_1$-$C_{10}$ alkyl, or substituted or unsubstituted $C_1$-$C_{10}$ heteroalkyl containing at least one hetero atom.

In addition, $L_2$ is a linker including at least one carbon, which is mentioned above, and any carbon in the liker may be a carbonyl carbon. The carbonyl may be at least one selected from aldehydes, ketones, carboxylic acids, esters, amides, enones, acyl halides, acid anhydrides, and imides.

In another case, $L_2$ may have a structure in which neighboring linkers are interconnected via a carbonyl carbon. Wherein, $L_2$ may include both a linker directly connected without a carbonyl carbon and a linker connected by a carbonyl carbon. For example, $L_2$ may have a structure including an amide (aminocarbonyl), such as "—$CH_2$—$CH_2$—C(=O)—NH—$CH_2$—$CH_2$—CH—CH—$CH_2$—." In addition, $L_2$ may have a structure including a carbonylamino, such as "—$CH_2$—$CH_2$—CH=CH—$CH_2$—."

When $L_2$ is an internucleotide phosphodiester bond, the deoxyribonucleoside represented by Formula 3 or 4 may be represented by Formulas 3-1 or 4-1 below, respectively.

[Formula 3-1]

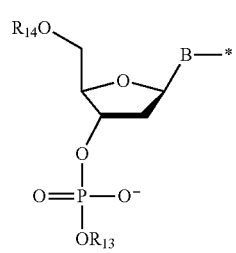

[Formula 4-1]

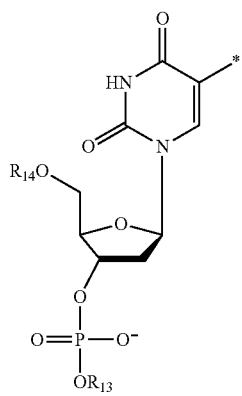

$R_{18}$ may be hydroxy or $P(OR_{15})(N(R_{16}R_{17}))$, or a support or nucleic acid to which the reporter represented by Formula 1 or Formula 2 is bound.

That is, when $R_{13}$ is -$L_2$-$R_{18}$, the reporter represented by Formula 1 or 2 may be bound to a support or a nucleic acid (RNA or DNA) via $L_2$.

The support may be prepared with at least one selected from glass, cellulose, nylon, acrylamide gel, dextran, polystyrene, alginate, collagen, peptides, fibrin, hyaluronic acid, agarose, polyhydroxyethyl methacrylate, polyvinyl alcohol, polyethylene glycol, polyethylene oxide, polyethylene glycol diacrylate, gelatin, Matrigel, polylactic acid, carboxymethyl cellulose, dextran, chitosan, latex, and Sepharose, and may be prepared in the form of beads or a membrane.

Meanwhile, when $R_{14}$ is an alcohol protecting group, the alcohol protecting group may be at least one selected from acetal, acetyl, benzoyl, benzyl, β-methoxyethoxymethyl, dimethoxytrityl, methoxymethyl, methoxytrityl, p-methoxybenzyl, p-methoxyphenyl, methylthiomethyl, trityl, tetrahydropyranyl, tetrahydrofuran, trimethylsilyl, tert-butyldimethylsilyl, tri-iso-propylsiloxymethyl, and tri-iso-propylsilyl.

$R_1$ to $R_{11}$ may be independently present as the functional groups defined above, but in some embodiments, at least one of $R_1$ to $R_{11}$ may be bonded with an adjacent substituent, thereby forming substituted or unsubstituted ring (e.g., a 4-membered ring, a 5-membered ring, a 6-membered ring, a ring formed of more than 6 members, or a fusion ring formed by joining a plurality of rings). Alternatively, the ring may be an aliphatic or aromatic ring.

When at least one of $R_1$ to $R_{11}$ is bonded with an adjacent substituent to form substituted or unsubstituted ring, at least one of $R_1$ to $R_{11}$ may be bonded with an adjacent substituent via C, N, O, S, Se, or Si, or may be directly bonded with an adjacent substituent using a single bond.

In one embodiment, the reporter may be represented by Formula 1, and when $Z_1$ is $NR_5R_6$, $R_5$ or $R_6$ may be bonded with $R_3$ or $R_4$, thereby forming substituted or unsubstituted ring.

The formation of the substituted or unsubstituted rings by $R_5$ and $R_6$ is independent, and a ring formed by bonding $R_5$ and $R_3$ (or $R_4$) and a ring formed by bonding $R_6$ and $R_4$ (or $R_3$) may be simultaneously present in one compound.

In another embodiment, the reporter is represented by Formula 1, and when $Z_1$ is $OR_7$, $R_7$ is bonded with $R_3$ or $R_4$, thereby forming substituted or unsubstituted ring.

In still another embodiment, the reporter may be represented by Formula 2, when $Z_2$ is $NR_8$, $R_8$ may be bonded with $R_3$ or $R_4$, thereby forming substituted or unsubstituted ring.

When at least one of $R_1$ to $R_{11}$ is bonded with an adjacent substituent to form a substituted ring, any substituent other than hydrogen may be bonded to at least one carbon of the ring. The substituent may be selected from deuterium, substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, substituted or unsubstituted $C_2$-$C_{20}$ heterocycloalkyl, hydroxy, oxido (—$O^-$), substituted or unsubstituted $C_1$-$C_{10}$ alkoxy, substituted or unsubstituted $C_3$-$C_{20}$ cycloalkyloxy, substituted or unsubstituted $C_5$-$C_{20}$ aryloxy, substituted or unsubstituted $C_2$-$C_{20}$ heteroaryloxy, substituted or unsubstituted $C_5$-$C_{20}$ aryl, substituted or unsubstituted $C_2$-$C_{20}$ heteroaryl, substituted or unsubstituted $C_5$-$C_{20}$ aralkyl, substituted or unsubstituted $C_1$-$C_{10}$ alkylthio, substituted or unsubstituted $C_5$-$C_{20}$ arylthio, substituted or unsubstituted $C_3$-$C_{20}$ cycloalkylthio, substituted or unsubstituted $C_2$-$C_{20}$ heteroarylthio, substituted or unsubstituted acylamino, acyloxy, substituted or unsubstituted phosphino, carboxylate (-$CO_2^-$), trifluoromethylsulfonyl (-$SO_2CF_3$), substituted or unsubstituted ammonium, nitro, sulfonic acid (-$SO_3H$), sulfate, substituted sulfonyl, substituted sulfonic acid ester, substituted or unsubstituted sulfonamide, substituted thioketone, trihalomethyl (—$CF_3$, —$CCl_3$, —$CBr_3$, or —$CI_3$), haloformyl (—COCl, —COBr, or —COI), formyl (—CHO), acyl, carboxyl, substituted ester, substituted or unsubstituted aminocarbonyl, nitro, nitroso (—N=O), fluoro (—F), chloro (—Cl), bromo (—Br), iodo (—I), substituted or unsubstituted germanium, substituted or unsubstituted boron, substituted or unsubstituted aluminum, substituted or unsubstituted silyl, substituted or unsubstituted amide, carbamate, carboxylate, substituted or unsubstituted phosphine, substituted or unsubstituted phosphoric acid, phosphate, phosphonic acid, phosphonate, nitrile, hydrazine, acetal, ketal, polyalkyleneoxide, and -$L_1$-$R_{12}$.

In addition, according to another aspect of the present invention, a reporter for labeling a nucleic acid, represented by Formula 5 below, is provided.

[Formula 5]

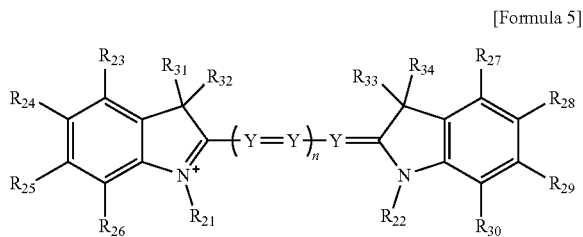

Wherein, $R_{21}$ and $R_{22}$ may each be independently selected from hydrogen, deuterium, substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, substituted or unsubstituted $C_2$-$C_{20}$ heterocycloalkyl, substituted or unsubstituted $C_5$-$C_{20}$ aryl, and substituted or unsubstituted $C_2$-$C_{20}$ heteroaryl, and $R_{23}$ to $R_{30}$ may each be independently a functional group selected from hydrogen, deuterium, substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, substituted or unsubstituted $C_2$-$C_{20}$ heterocycloalkyl, hydroxy, oxido (—O$^-$), substituted or unsubstituted $C_1$-$C_{10}$ alkoxy, substituted or unsubstituted $C_3$-$C_{20}$ cycloalkyloxy, substituted or unsubstituted $C_5$-$C_{20}$ aryloxy, substituted or unsubstituted $C_2$-$C_{20}$ heteroaryloxy, substituted or unsubstituted $C_5$-$C_{20}$ aryl, substituted or unsubstituted $C_2$-$C_{20}$ heteroaryl, substituted or unsubstituted $C_5$-$C_{20}$ aralkyl, substituted or unsubstituted $C_1$-$C_{10}$ alkylthio, substituted or unsubstituted $C_5$-$C_{20}$ arylthio, substituted or unsubstituted $C_3$-$C_{20}$ cycloalkylthio, substituted or unsubstituted $C_2$-$C_{20}$ heteroarylthio, substituted or unsubstituted acylamino, acyloxy, substituted or unsubstituted phosphino, carboxylate (—CO$_2^-$), trifluoromethylsulfonyl (—SO$_2$CF$_3$), substituted or unsubstituted ammonium, nitro, sulfonic acid (—SO$_3$H), sulfonate, substituted sulfonyl, substituted sulfonic acid ester, substituted or unsubstituted sulfonamide, substituted thioketone, trihalomethyl (—CF$_3$, —CCl$_3$, —CBr$_3$, or —CI$_3$), haloformyl (—COCl, —COBr, or —COI), formyl (—CHO), acyl, carboxyl, substituted ester, substituted or unsubstituted aminocarbonyl, nitro, nitroso (—N=O), fluoro (—F), chloro (—Cl), bromo (—Br), iodo (—I), substituted or unsubstituted germanium, substituted or unsubstituted boron, substituted or unsubstituted aluminum, substituted or unsubstituted silyl, substituted or unsubstituted amide, carbamate, carboxylate, substituted or unsubstituted phosphine, substituted or unsubstituted phosphoric acid, phosphate, phosphonic acid, phosphonate, nitrile, hydrazine, acetal, ketal, polyalkyleneoxide, and -L$_1$-R$_{12}$, or two adjacent functional groups are bonded to each other to form a ring.

In addition, $R_{31}$ to $R_{34}$ may each be independently selected from hydrogen, deuterium, substituted or unsubstituted $C_1$-$C_{10}$ alkyl, substituted or unsubstituted $C_1$-$C_{10}$ heteroalkyl containing at least one hetero atom, and -L$_1$-R$_{12}$, and at least one of $R_{31}$ to $R_{34}$ may be -L$_1$-R$_{12}$. The definition of -L$_1$-R$_{12}$ is the same as described above.

In reporters according to various embodiments of the present invention, at least one of $R_{31}$ to $R_{34}$ has a functional group represented by -L$_1$-R$_{12}$, and the reporters can bond to and label a target biomolecule (e.g., a nucleic acid) via a functional group represented by -L$_1$-R$_{12}$.

Y is CR$_{35}$, each R$_{35}$ is selected from hydrogen, deuterium, substituted or unsubstituted $C_1$-$C_{10}$ alkyl, substituted or unsubstituted $C_1$-$C_{10}$ heteroalkyl containing at least one hetero atom, fluoro (—F), chloro (—Cl), bromo (—Br), and iodo (—I), and n is an integer of 1 to 4.

In addition, R$_{35}$ may be independently present as the functional groups defined above, but in some embodiments, R$_{35}$ may be bonded with R$_{35}$ of neighboring Y to form substituted or unsubstituted ring (e.g., a 4-membered ring, a 5-membered ring, a 6-membered ring, a ring formed of more than 6 members, or a fusion ring formed by joining a plurality of rings). In addition, the ring may be an aliphatic or aromatic ring.

When R$_{35}$ is bonded with R$_{35}$ of a neighboring Y to form a substituted ring, any substituent other than hydrogen may be bonded to at least one carbon of the ring. The substituent may be selected from deuterium, substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, substituted or unsubstituted $C_2$-$C_{20}$ heterocycloalkyl, hydroxy, oxido (—O$^-$), substituted or unsubstituted $C_1$-$C_{10}$ alkoxy, substituted or unsubstituted $C_3$-$C_{20}$ cycloalkyloxy, substituted or unsubstituted $C_5$-$C_{20}$ aryloxy, substituted or unsubstituted $C_2$-$C_{20}$ heteroaryloxy, substituted or unsubstituted $C_5$-$C_{20}$ aryl, substituted or unsubstituted $C_2$-$C_{20}$ heteroaryl, substituted or unsubstituted $C_5$-$C_{20}$ aralkyl, substituted or unsubstituted $C_1$-$C_{10}$ alkylthio, substituted or unsubstituted $C_5$-$C_{20}$ arylthio, substituted or unsubstituted $C_3$-$C_{20}$ cycloalkylthio, substituted or unsubstituted $C_2$-$C_{20}$ heteroarylthio, substituted or unsubstituted acylamino, acyloxy, substituted or unsubstituted phosphino, carboxylate (—CO$_2$), trifluoromethylsulfonyl (—SO$_2$CF$_3$), substituted or unsubstituted ammonium, nitro, sulfonic acid (—SO$_3$H), sulfate, substituted sulfonyl, substituted sulfonic acid ester, substituted or unsubstituted sulfonamide, substituted thioketone, trihalomethyl (—CF$_3$, —CCl$_3$, —CBr$_3$, or —CI$_3$), haloformyl (—COCl, —COBr, or —COI), formyl (—CHO), acyl, carboxyl, substituted ester, substituted or unsubstituted aminocarbonyl, nitro, nitroso (—N=O), fluoro (—F), chloro (—Cl), bromo (—Br), iodo (—I), substituted or unsubstituted germanium, substituted or unsubstituted boron, substituted or unsubstituted aluminum, substituted or unsubstituted silyl, substituted or unsubstituted amide, carbamate, carboxylate, substituted or unsubstituted phosphine, substituted or unsubstituted phosphoric acid, phosphate, phosphonic acid, phosphonate, nitrile, hydrazine, acetal, ketal, polyalkyleneoxide, and -L$_1$-R$_{12}$.

In addition, when any functional group of $R_{21}$ to $R_{35}$ is a substituted functional group, any substituent other than hydrogen may be bonded to at least one carbon of the functional group. The substituent may be selected from deuterium, substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, substituted or unsubstituted $C_2$-$C_{20}$ heterocycloalkyl, hydroxy, oxido (—O$^-$), substituted or unsubstituted $C_1$-$C_{10}$ alkoxy, substituted or unsubstituted $C_3$-$C_{20}$ cycloalkyloxy, substituted or unsubstituted $C_5$-$C_{20}$ aryloxy, substituted or unsubstituted $C_2$-$C_{20}$ heteroaryloxy, substituted or unsubstituted $C_5$-$C_{20}$ aryl, substituted or unsubstituted $C_2$-$C_{20}$ heteroaryl, substituted or unsubstituted $C_5$-$C_{20}$ aralkyl, substituted or unsubstituted $C_1$-$C_{10}$ alkylthio, substituted or unsubstituted $C_5$-$C_{20}$ arylthio, substituted or unsubstituted $C_3$-$C_{20}$ cycloalkylthio, substituted or unsubstituted $C_2$-$C_{20}$ heteroarylthio, substituted or unsubstituted acylamino, acyloxy, substituted or unsubstituted phosphino, carboxylate (—CO$_2^-$), trifluoromethylsulfonyl (—SO$_2$CF$_3$), substituted or unsubstituted ammonium, nitro, sulfonic acid (—SO$_3$H), sulfate, substituted sulfonyl, substituted sulfonic acid ester, substituted or unsubstituted sulfonamide, substituted thioketone, trihalomethyl (—CF$_3$, —CCl$_3$, —CBr$_3$, or —CI$_3$), haloformyl (—COCl, —COBr, or —COI), formyl (—CHO), acyl, carboxyl, substituted ester, substituted or unsubstituted aminocarbonyl, nitro, nitroso (—N=O), fluoro (—F), chloro (—Cl), bromo (—Br), iodo (—I), substituted or unsubstituted germanium, substituted or unsubstituted boron, substituted or unsubstituted aluminum, substituted or unsubstituted silyl, substituted or unsubstituted amide, carbamate, carboxylate, substituted or unsubstituted phosphine, substituted or unsubstituted phosphoric acid, phosphate, phosphonic acid, phosphonate, nitrile, hydrazine, acetal, ketal, polyalkyleneoxide, and -$L_1$-$R_{12}$.

When the functional group defined in the present invention is alkenyl or alkynyl, the sp$^2$-hybrid carbon of an alkenyl or the sp-hybrid carbon of an alkynyl is directly bonded, or indirectly bonded via the sp$^3$-hybrid carbon of an alkyl bonded thereto.

In the present invention, the $C_a$-$C_b$ functional group refers to a functional group having a to b carbon atoms. For example, $C_a$-$C_b$ alkyl refers to a saturated aliphatic group, including a linear or branched alkyl having a to b carbon atoms. The linear or branched alkyl may have 40 or less carbon atoms in its main chain (e.g., $C_1$-$C_{40}$ linear, or $C_3$-$C_{40}$ branched).

Specifically, the alkyl may be methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, or n-octyl.

In addition, in the present invention, alkoxy is either of an —O-(alkyl) group and an —O-(unsubstituted cycloalkyl) group, and is linear or branched hydrocarbon having one or more ether groups and 1 to 10 carbon atoms.

Specific examples of the alkoxy include methoxy, ethoxy, propoxy, isopropoxy, n-butoxy, tert-butoxy, sec-butoxy, n-pentoxy, n-hexoxy, 1,2-dimethylbutoxy, cyclopropyloxy, cyclobutyloxy, cyclopentyloxy, and cyclohexyloxy, but the present invention is not limited thereto.

In addition, in the present invention, halogen means fluoro (—F), chloro (—Cl), bromo (—Br), or iodo (—I), and haloalkyl is alkyl substituted with the above-described halogen. For example, halomethyl means methyl in which at least one of the hydrogens is substituted with halogen (—CH$_2$X, —CHX$_2$ or —CX$_3$).

In the present invention, "aralkyl" is the generic term for —(CH$_2$)$_n$Ar, which is a functional group in which a carbon of alkyl is substituted with aryl. Examples of the aralkyl include benzyl (—CH$_2$C$_6$H$_5$) and phenethyl (—CH$_2$CH$_2$C$_6$H$_5$).

In the present invention, aryl is, unless defined otherwise, an unsaturated aromatic ring including a single ring, or multiple rings (preferably, 1 to 4 rings) conjugated or connected by covalent bonds. Non-limiting examples of the aryl include phenyl, biphenyl, o-terphenyl, m-terphenyl, p-terphenyl, 1-naphthyl, 2-naphthyl, 1-anthryl, 2-anthryl, 9-anthryl, 1-phenanthrenyl, 2-phenanthrenyl, 3-phenanthrenyl, 4-phenanthrenyl, 9-phenanthrenyl, 1-pyrenyl, 2-pyrenyl, and 4-pyrenyl.

In the present invention, heteroaryl is a functional group in which one or more carbon atoms in the aryl defined above are substituted with a non-carbon atom such as nitrogen, oxygen or sulfur. Non-limiting examples of the heteroaryl include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridaziyl, triazinyl, piperidinyl, morpholinyl, thiomorpholinyl, pyrazinyl, piperainyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazoyl, acridinyl, phenazinyl, phenothizinyl, phenoxazinyl, purinyl, benzimidazolyl, benzothiazolyl, and analogs conjugated therewith.

In the present invention, unless defined otherwise, a hydrocarbon ring (cycloalkyl) or a hydrocarbon ring having a hetero atom (heterocycloalkyl) may be understood as a cyclic structure of an alkyl or heteroalkyl, respectively.

Non-limiting examples of the cycloalkyls include cyclopentyl, cyclohexyl, 1-cyclohexenyl, 3-cyclohexenyl, and cycloheptyl. Non-limiting examples of the heterocycloalkyls include 1-(1,2,5,6-tetrahydropyrinyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothiene-2-yl, tetrahydrothiene-3-yl, 1-piperazinyl, and 2-piperazinyl.

In addition, the cycloalkyl or heterocycloalkyl may have a form in which cycloalkyl, heterocycloalkyl, aryl or heteroaryl is conjugated or connected by a covalent bond.

Wherein, the polyalkyleneoxide is a water-soluble polymer functional group, and examples of such polyalkyleneoxides include polyethylene glycol (PEG), polypropylene glycol (PPG), a polyethylene glycol-polypropylene glycol (PEG-PPG) copolymer, and N-substituted methacrylamide-containing polymers and copolymers.

The polyalkyleneoxide may be additionally substituted, as needed, as long as the characteristics of the polymer are maintained. For example, the substitution may be a chemical bond for increasing or decreasing the chemical or biological stability of the polymer. As a specific example, any carbon or terminal carbon in the polyalkyleneoxide may be substituted with hydroxy, alkyl ether (methyl ether, ethyl ether, propyl ether or the like), carboxymethyl ether, carboxyethyl ether, benzyl ether, dibenzylmethylene ether, or dimethylamine. In one embodiment, the polyalkyleneoxide may be polyethyleneoxide terminated with methyl ether (mPEG), wherein mPEG is represented by the formula —(CH$_2$CH$_2$O)$_n$CH$_3$, whose size may change depending on the size of n corresponding to the number of ethylene glycol repeat units.

In addition, the reporters represented by Formulas 1, 2, and 5 may have a structure further including a counter ion. The counter ion, which is an organic or inorganic anion, may be suitably selected in consideration of the solubility and stability of the reporter.

Examples of the counter ions of the reporter according to one embodiment of the present invention include inorganic anions such as a phosphoric acid hexafluoride ion, a halogen ion, a phosphoric acid ion, a perchloric acid ion, a periodic acid ion, an antimony hexafluoride ion, a tartaric acid hexafluoride ion, a fluoroboric acid ion, and a tetrafluoride ion; and organic anions such as a thiocyanate ion, a benzenesulfonic acid ion, a naphthalenesulfonic acid ion, a p-toluenesulfonic acid ion, an alkylsulfonic acid ion, a benzenecarboxylic acid ion, an alkylcarboxylic acid ion, a trihaloalkylcarboxylic acid ion, an alkyl sulfonic acid ion, a trihaloalkylsulfonic acid ion, and a nicotinic acid ion. In addition, metal compound ions such as bisphenylditol, thiobisphenol chelate, and bisdiol-α-diketone, metal ions such as sodium and potassium, and quaternary ammonium salts may also be selected as the counter ions.

Specific examples of the reporters represented by Formulas 1, 2, and 5 are as follows. However, the following exemplary compounds are provided to help understanding the reporters defined herein and are not intended to limit the scope of the reporters defined herein.

[Compound 1]

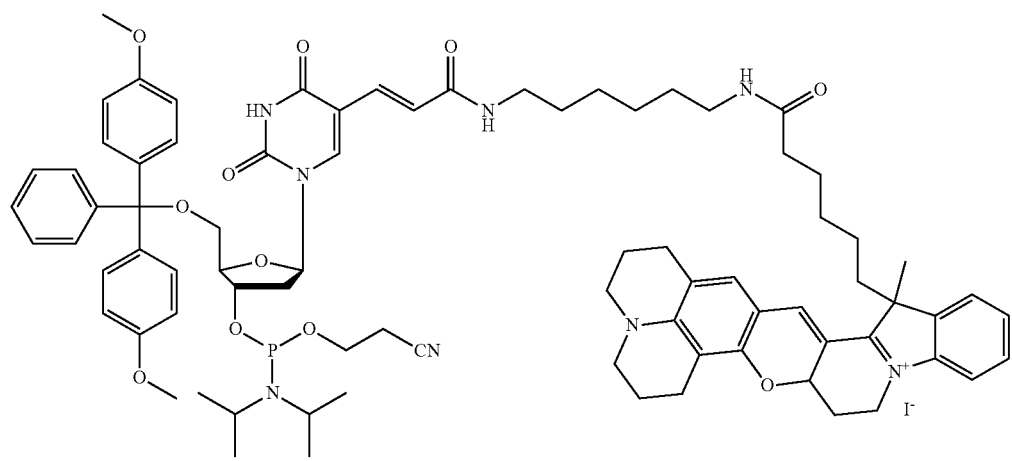

[Compound 2]

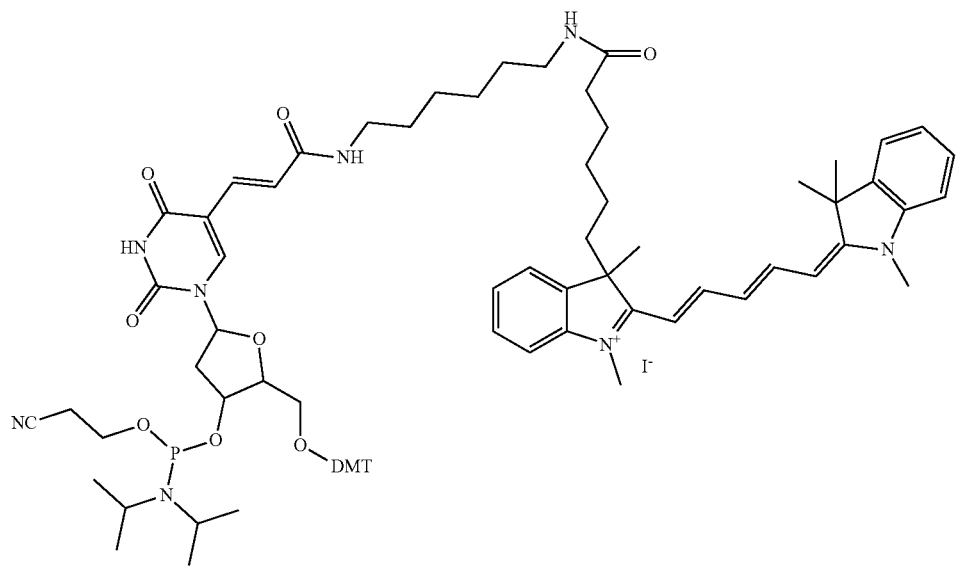

[Compound 3]
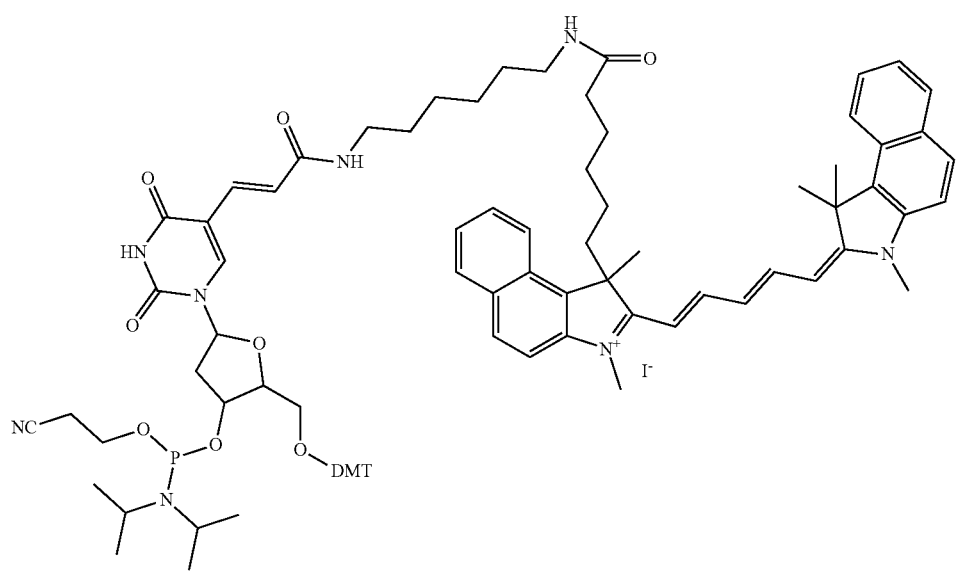
[Compound 4]
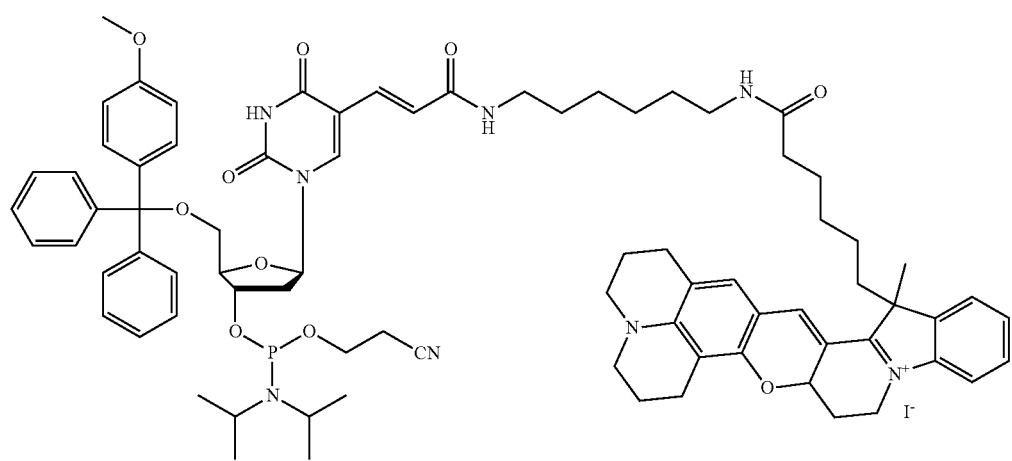
[Compound 5]
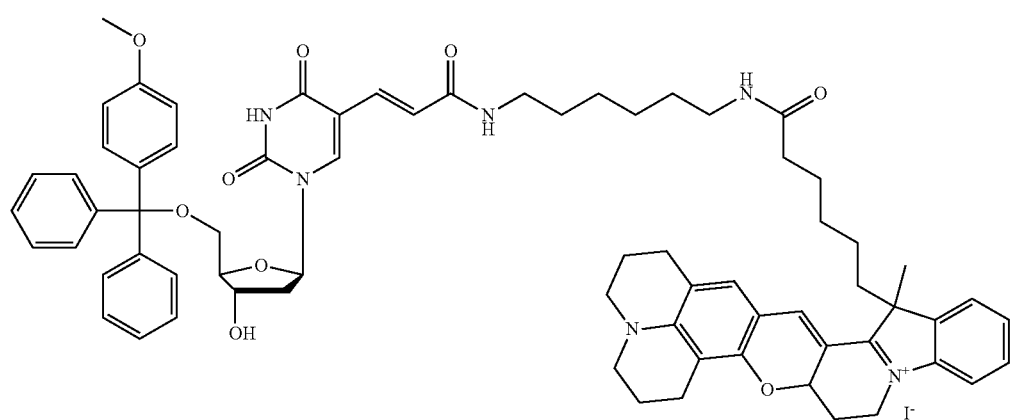

[Compound 6]
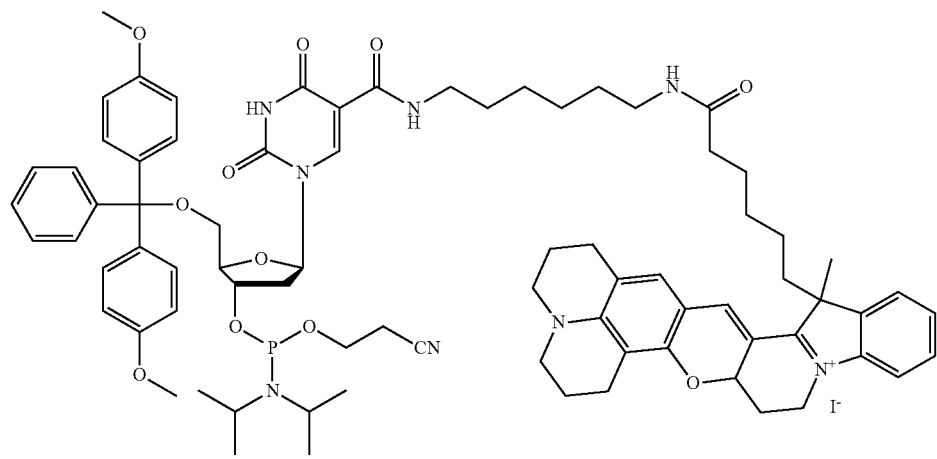
[Compound 7]
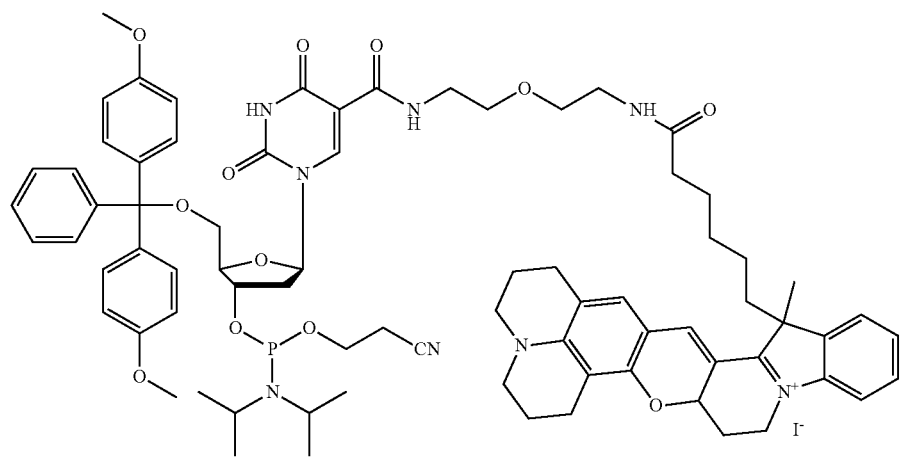
[Compound 8] [Compound 9]
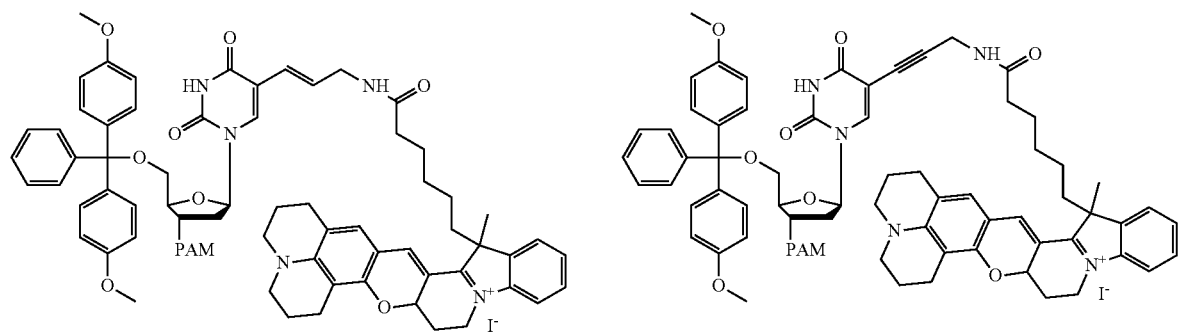

[Compound 10]
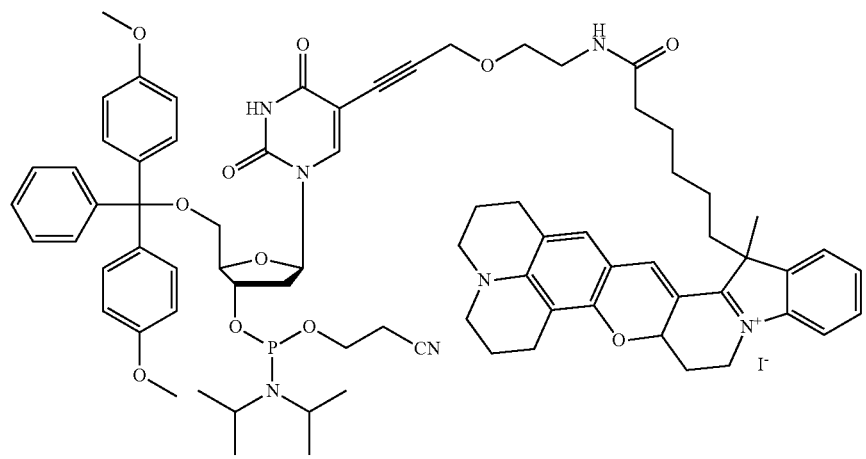
[Compound 11]
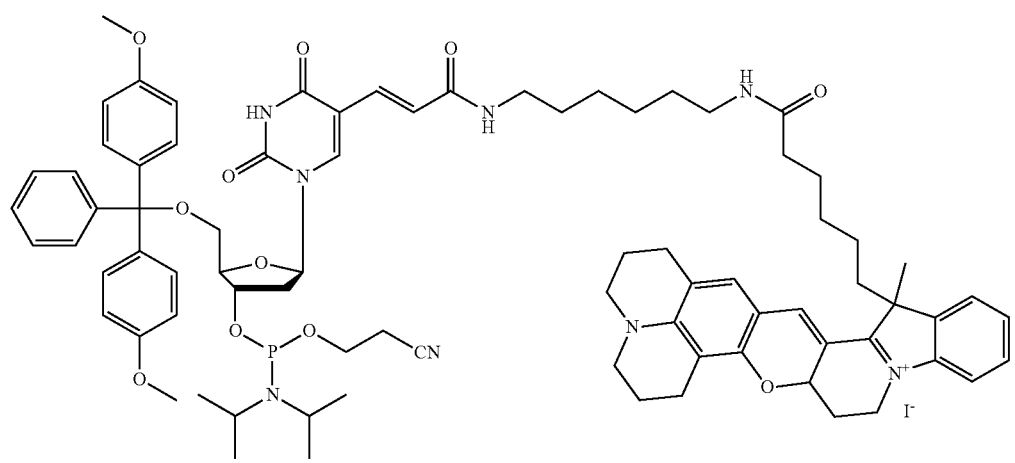
[Compound 12]
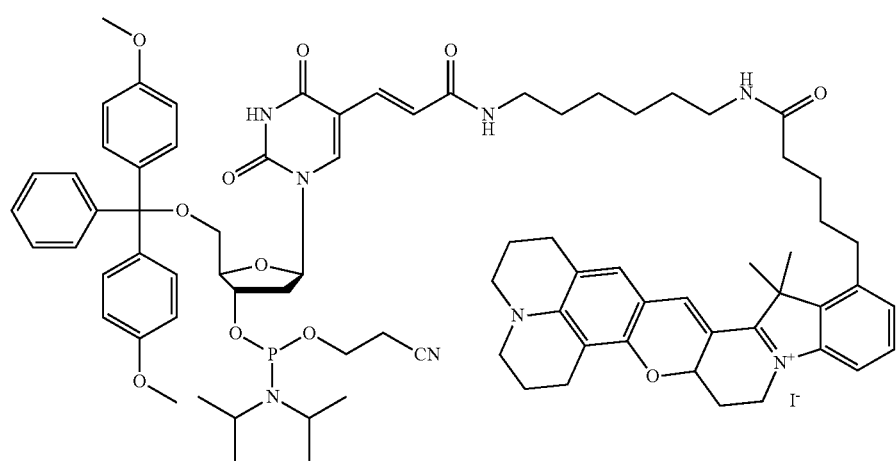

[Compound 13]
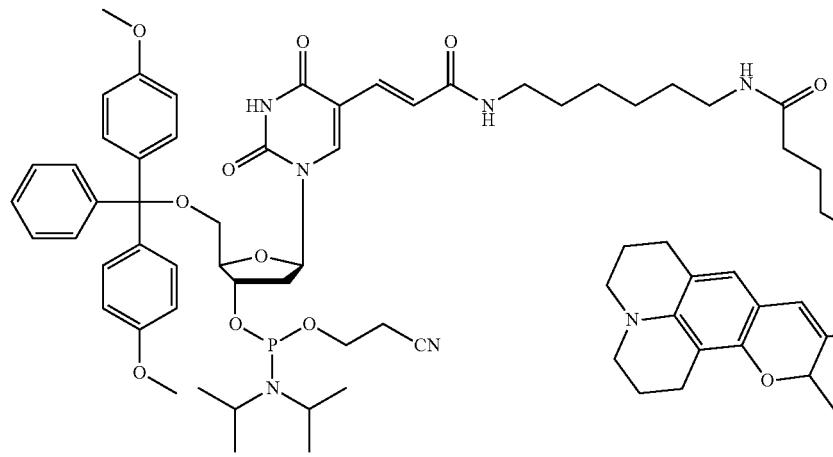
[Compound 14]
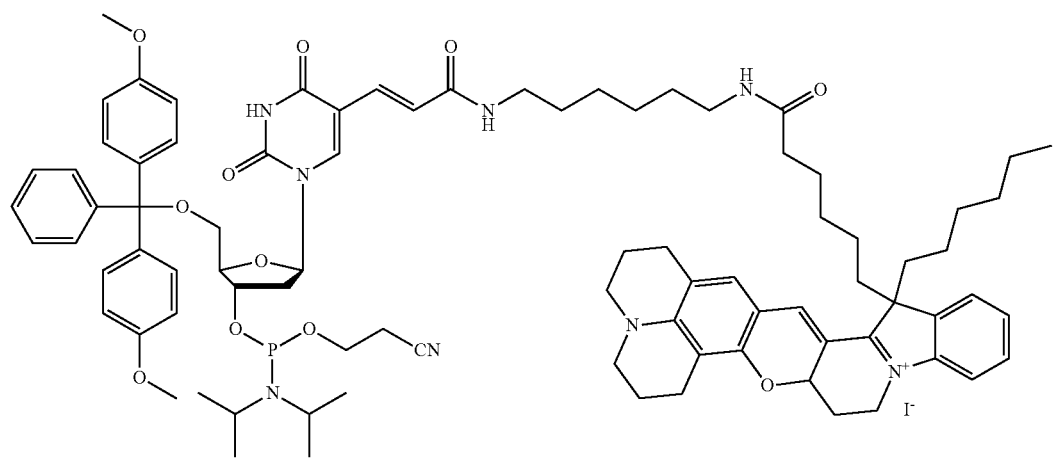
[Compound 15]
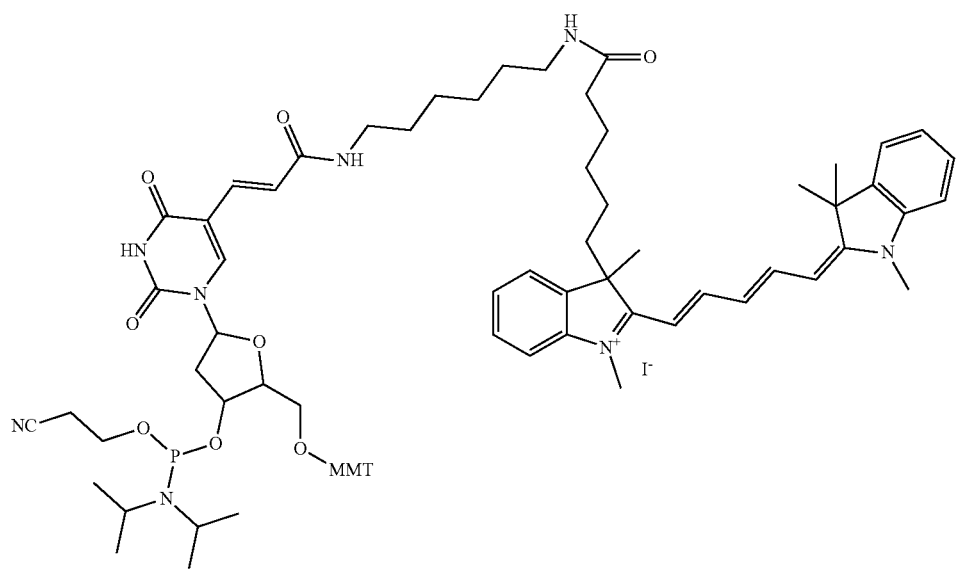

[Compound 16]
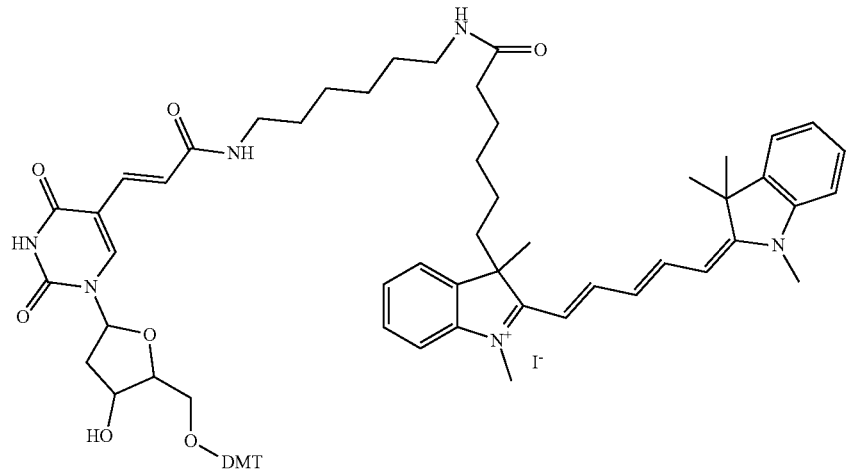
[Compound 17]
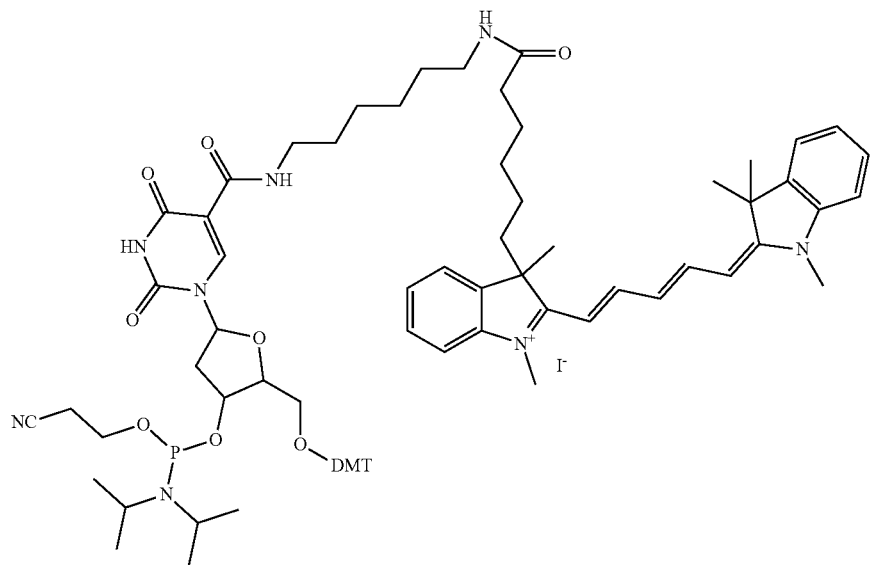
[Compound 18]
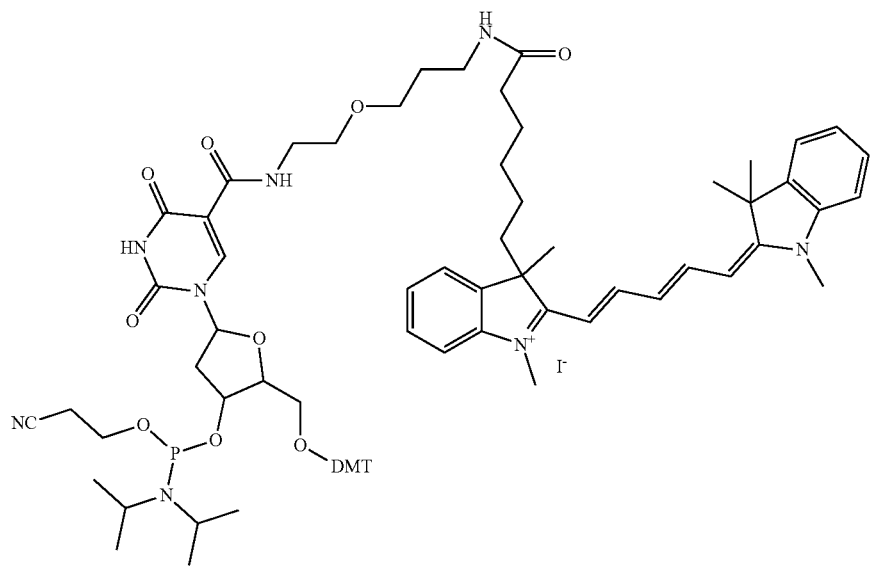

[Compound 19]
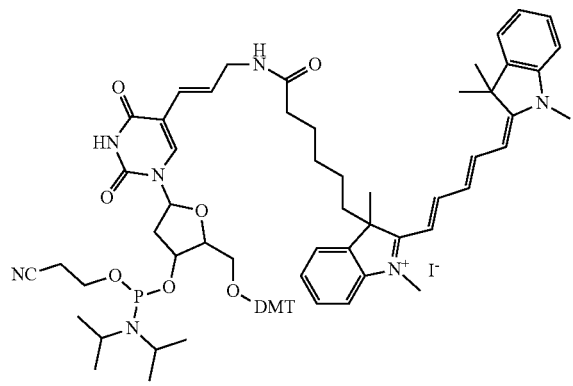
[Compound 20]
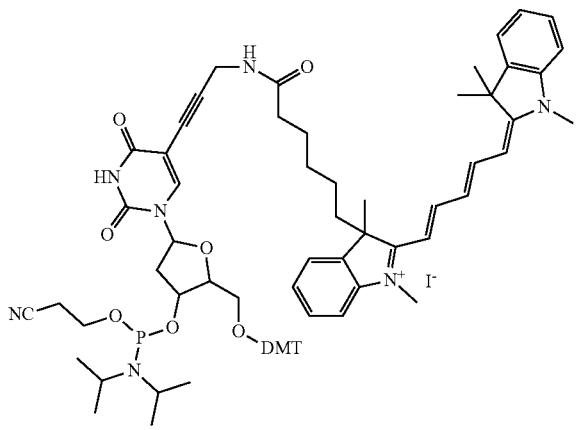
[Compound 21]
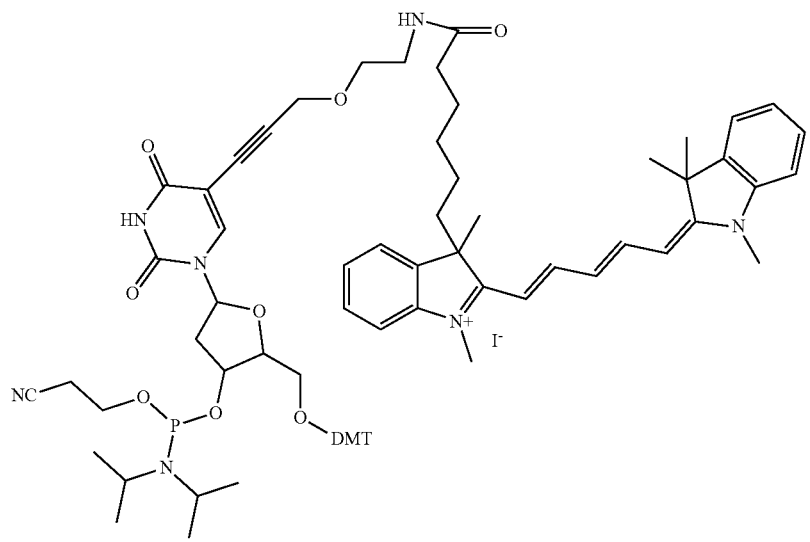
[Compound 22]
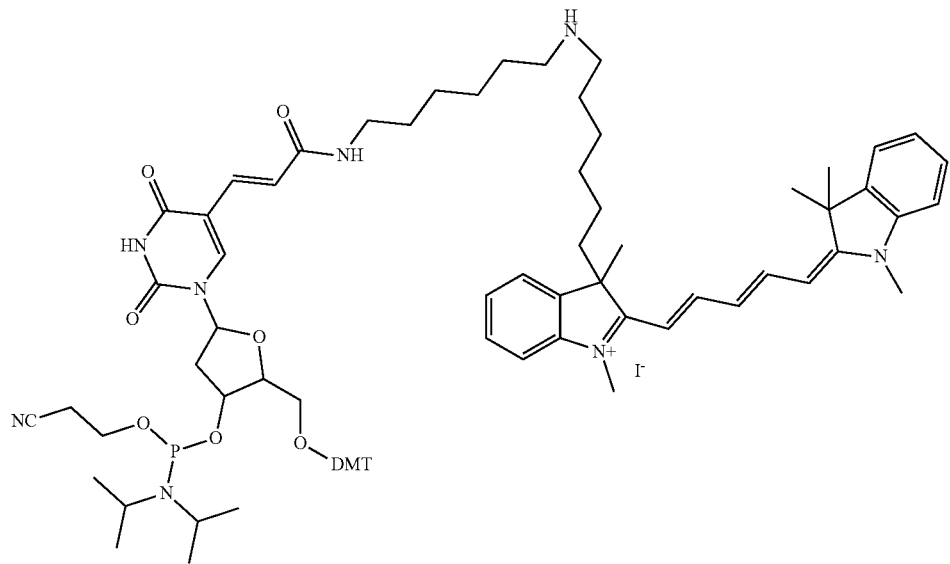

[Compound 23]
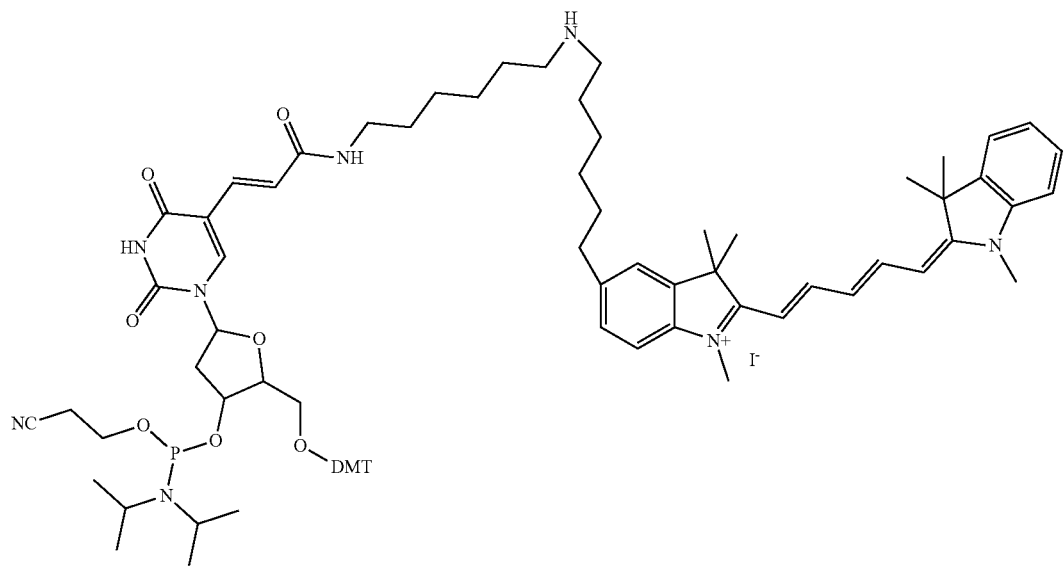
[Compound 24]
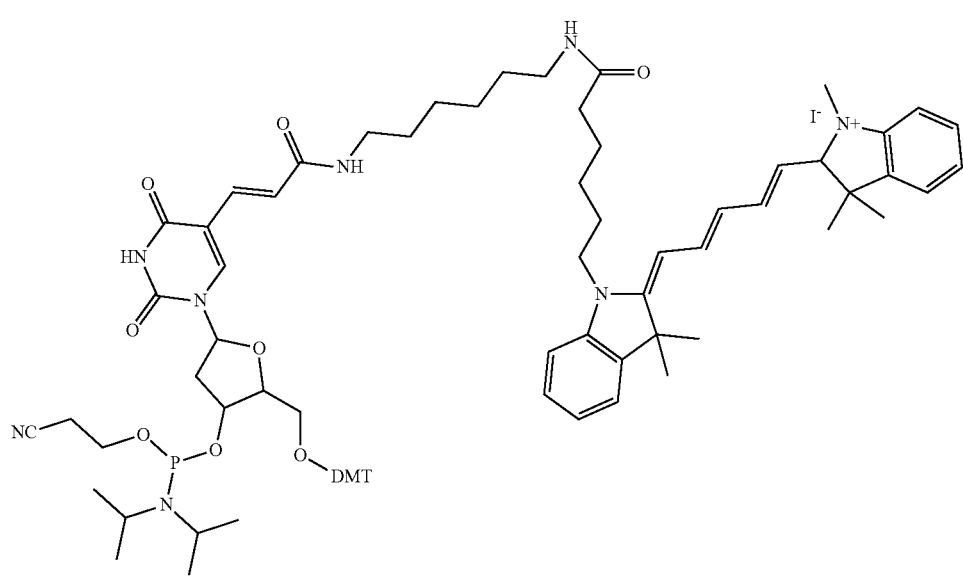

[Compound 25]
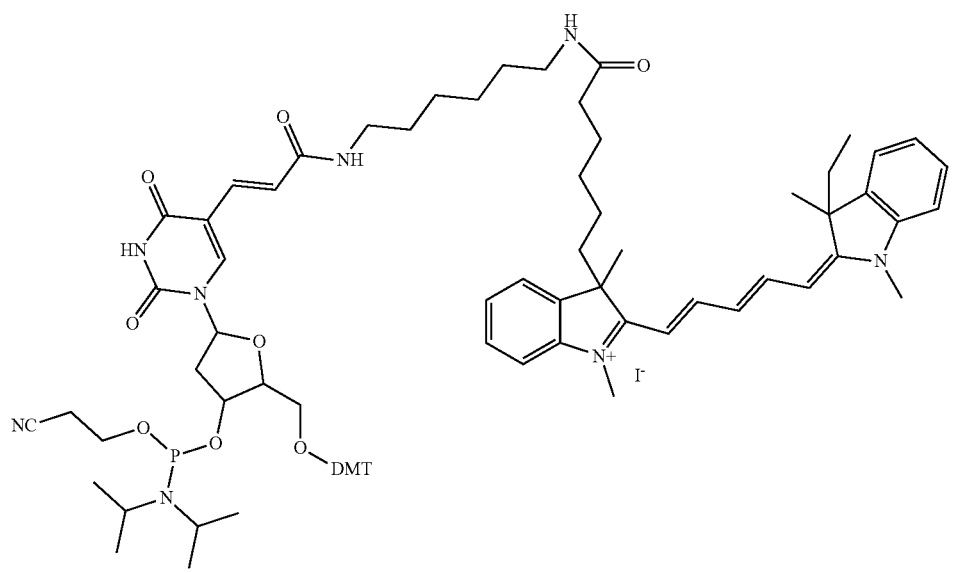
[Compound 26]
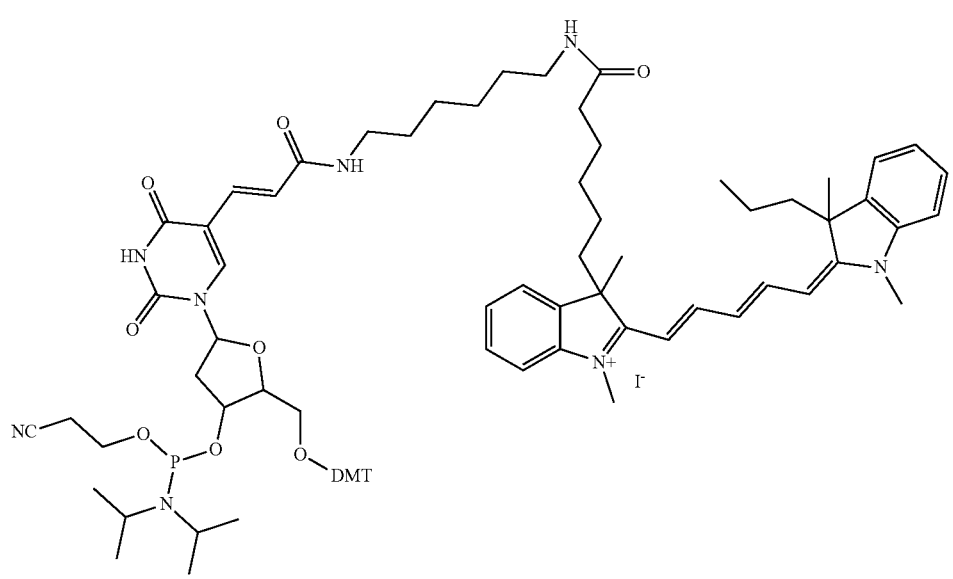

[Compound 27]
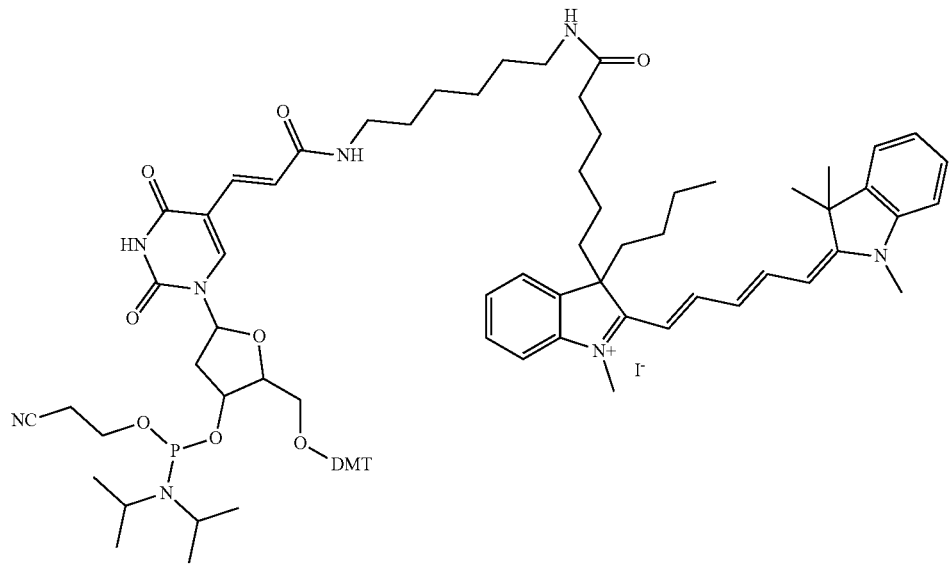
[Compound 28]
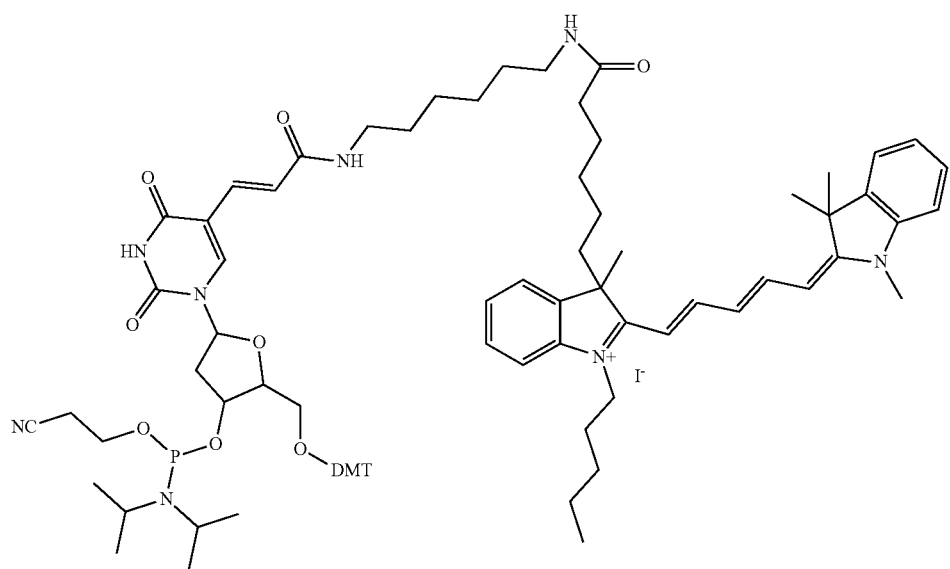

[Compound 29]
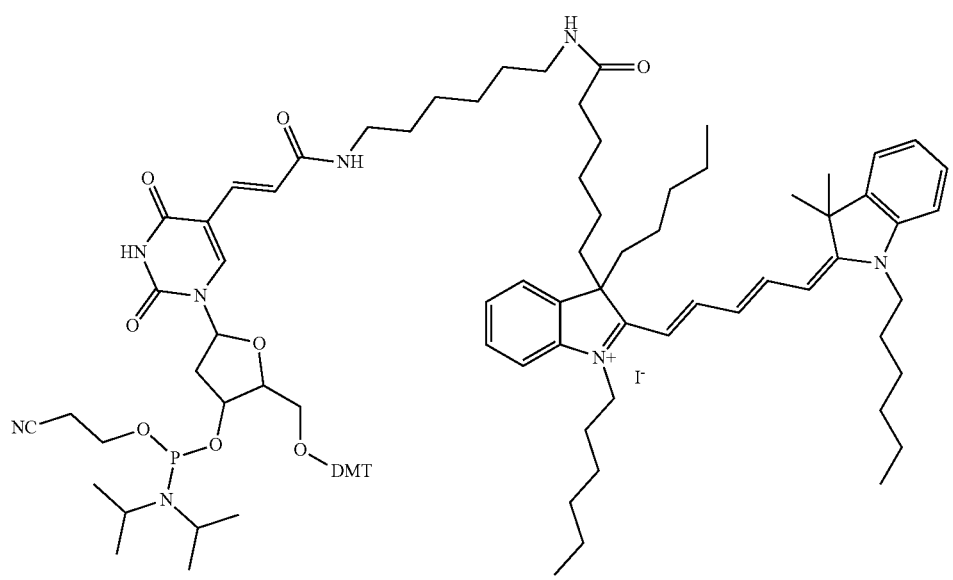
[Compound 30]
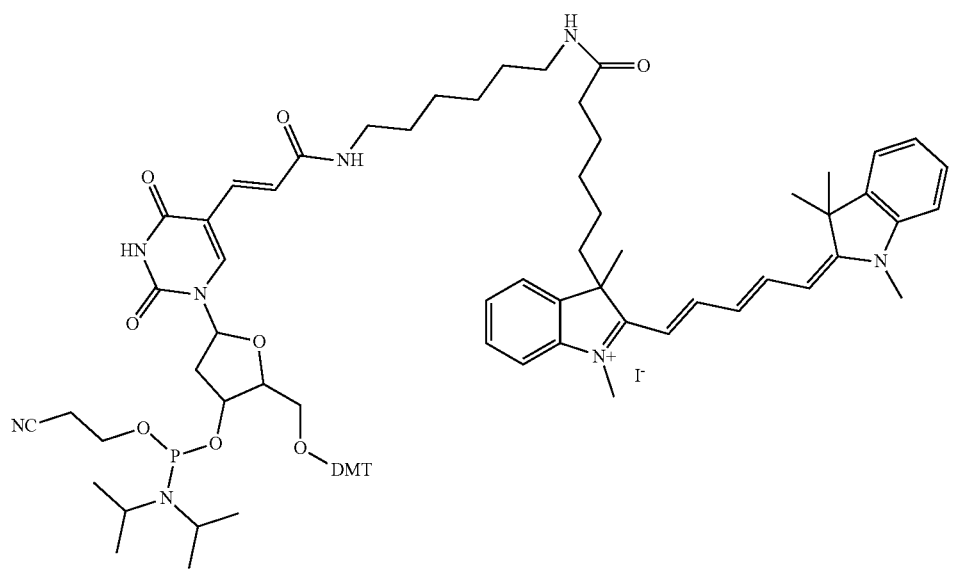

[Compound 31]
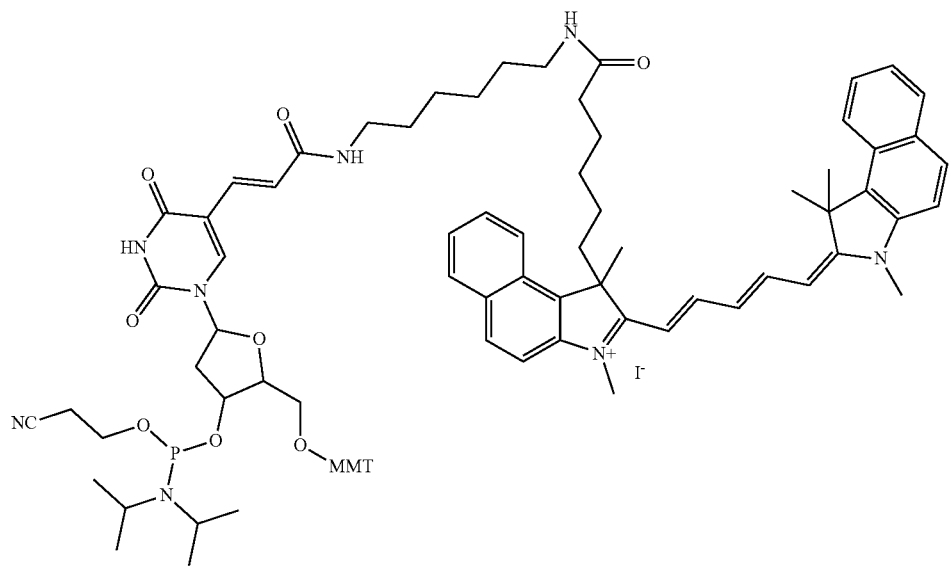
[Compound 32]
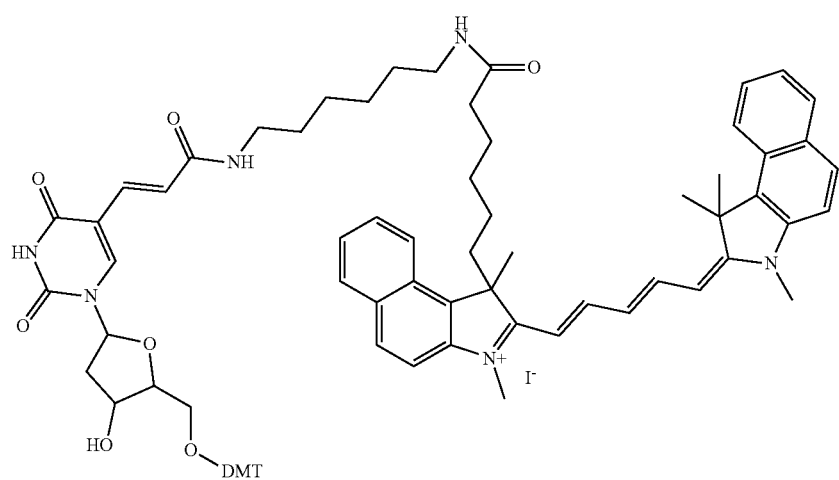
[Compound 33]
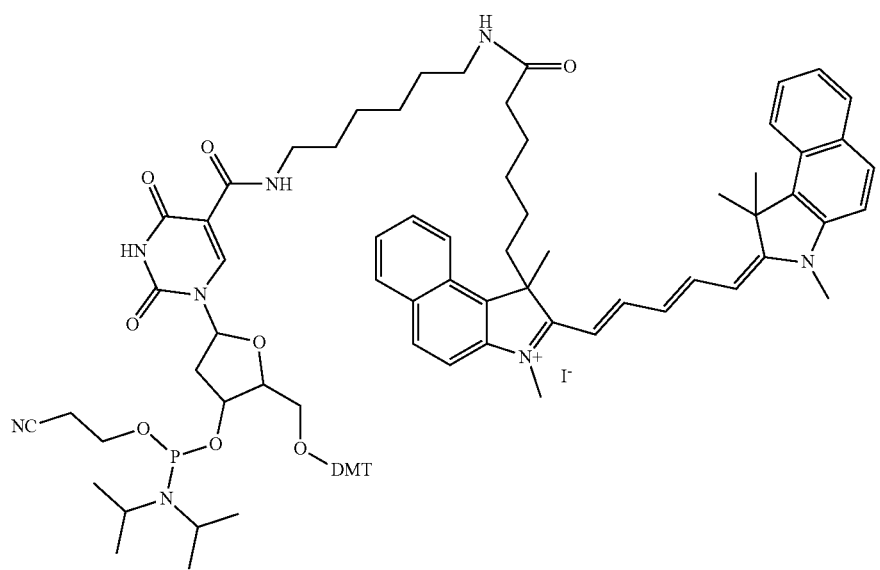

-continued
[Compound 34]
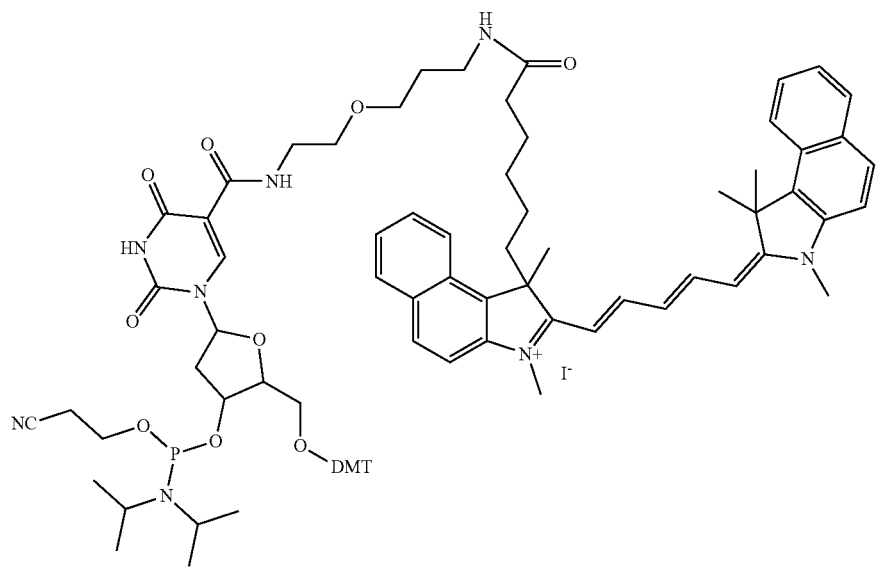
[Compound 35]
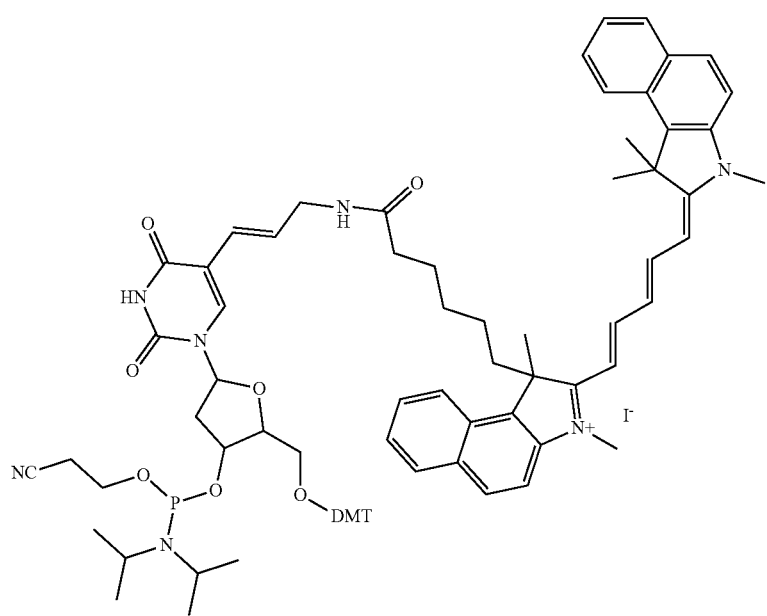

[Compound 36]
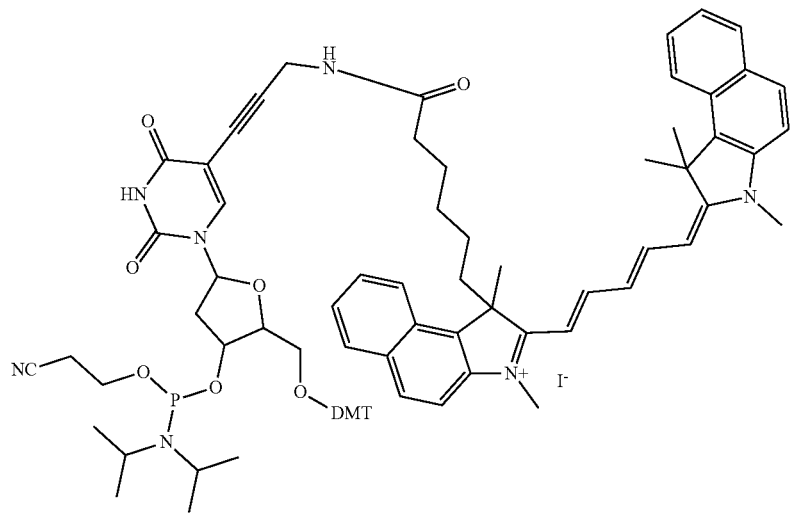
[Compound 37]
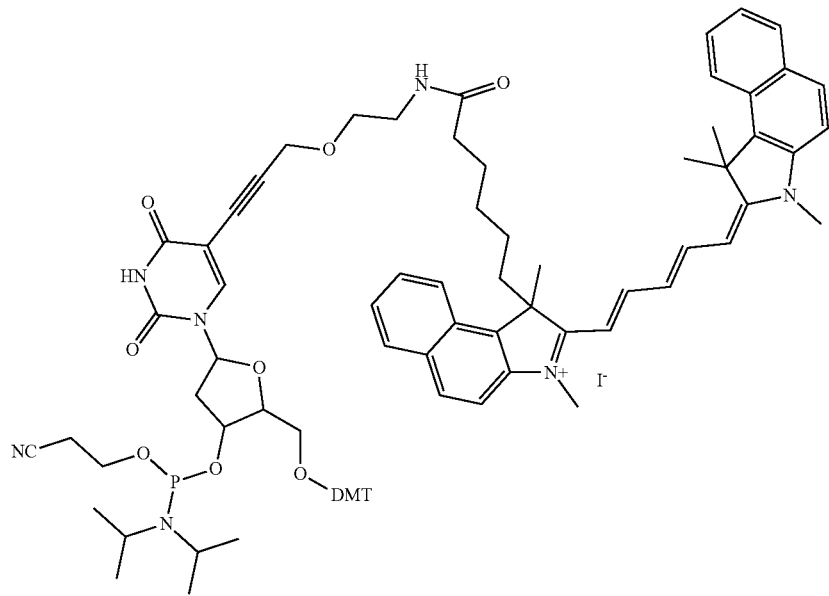

-continued
[Compound 38]
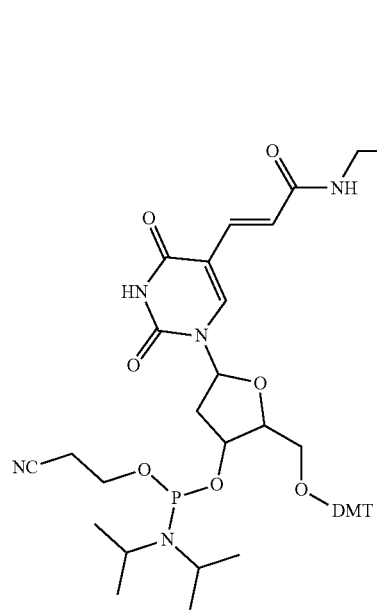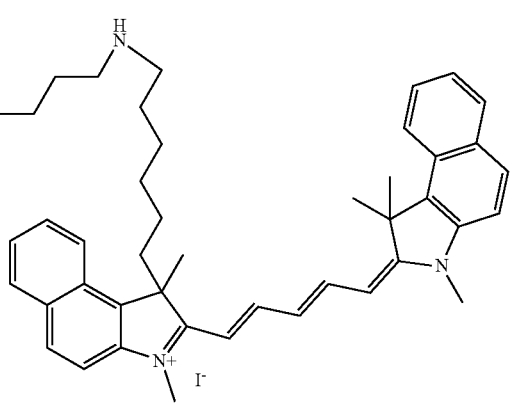
[Compound 39]
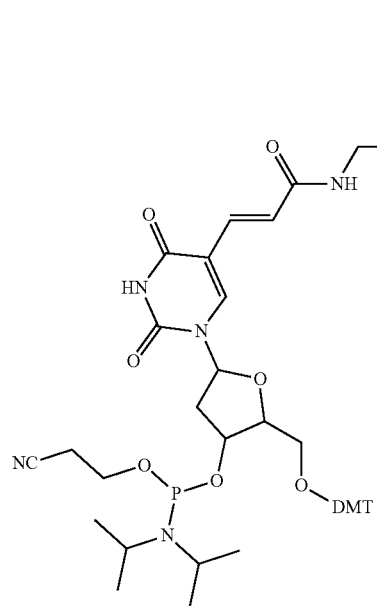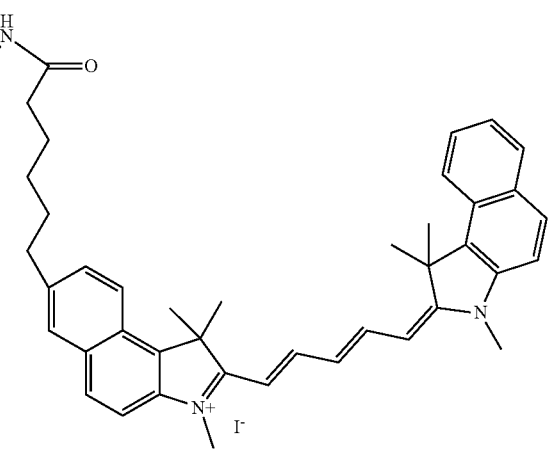

-continued
[Compound 40]
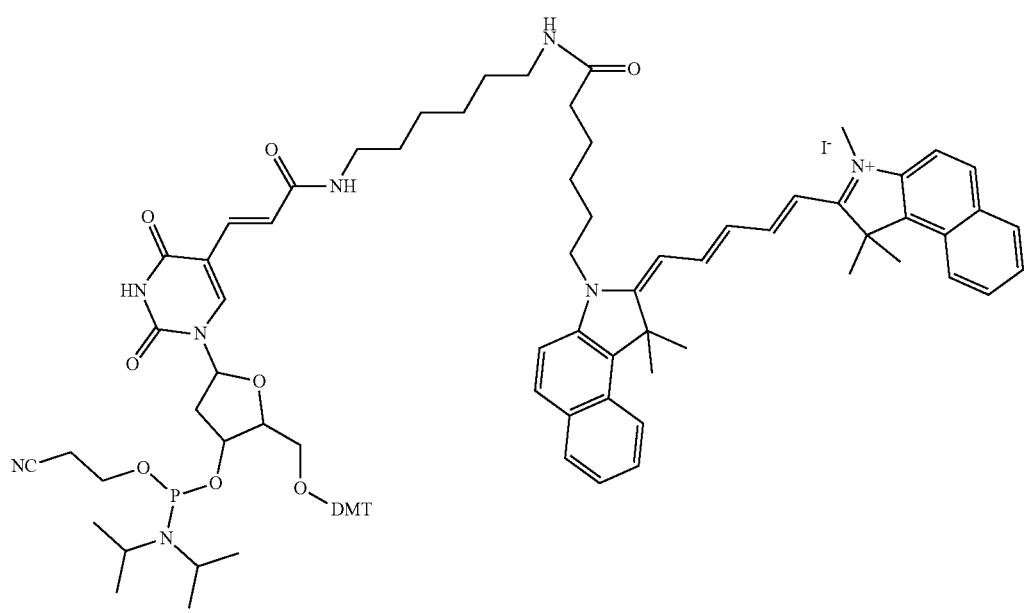
[Compound 41]
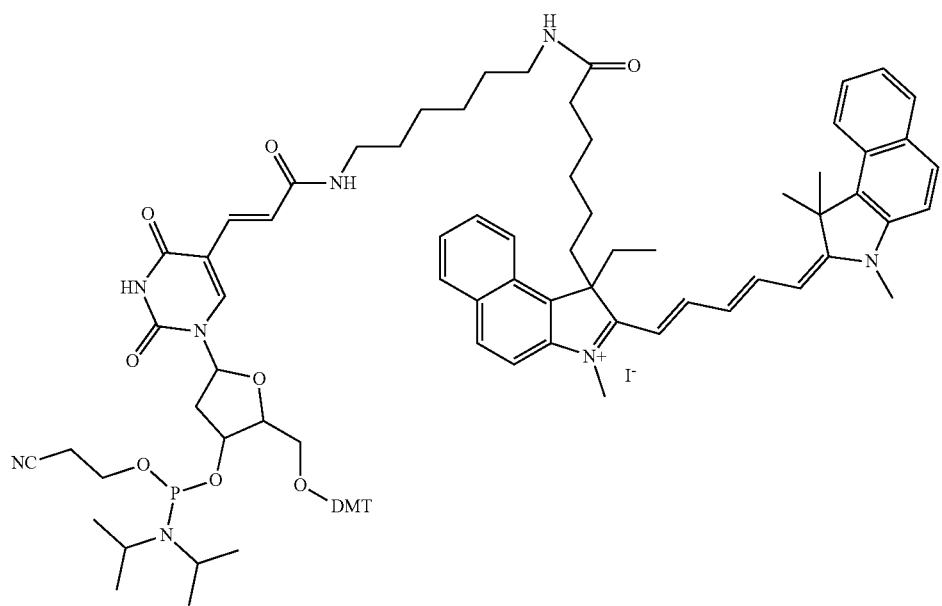

[Compound 42]
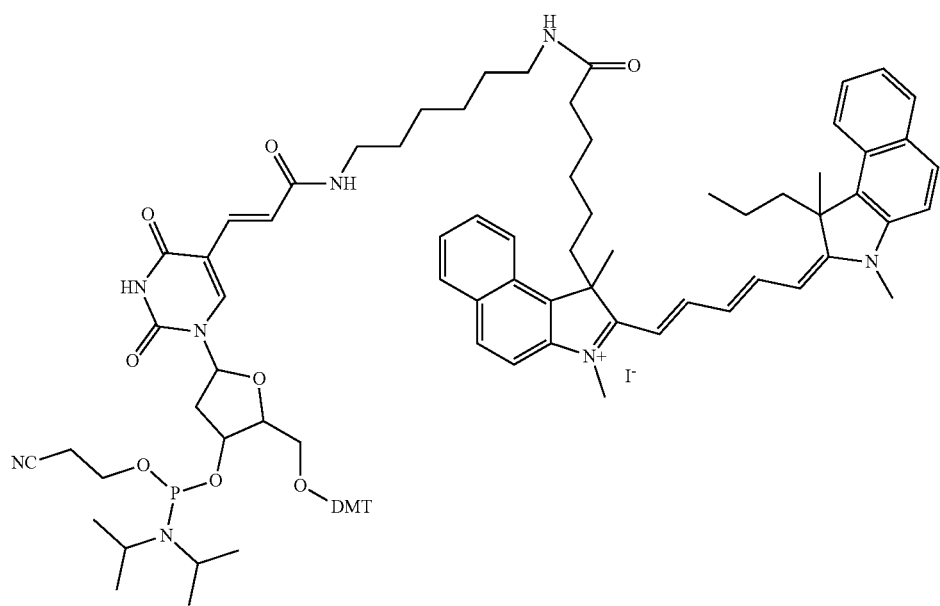
[Compound 43]
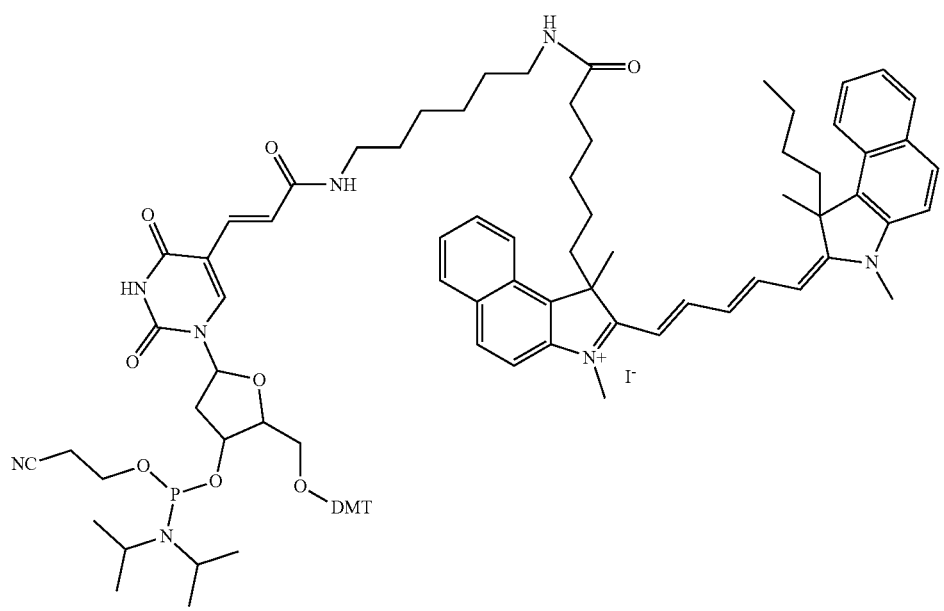

[Compound 44]
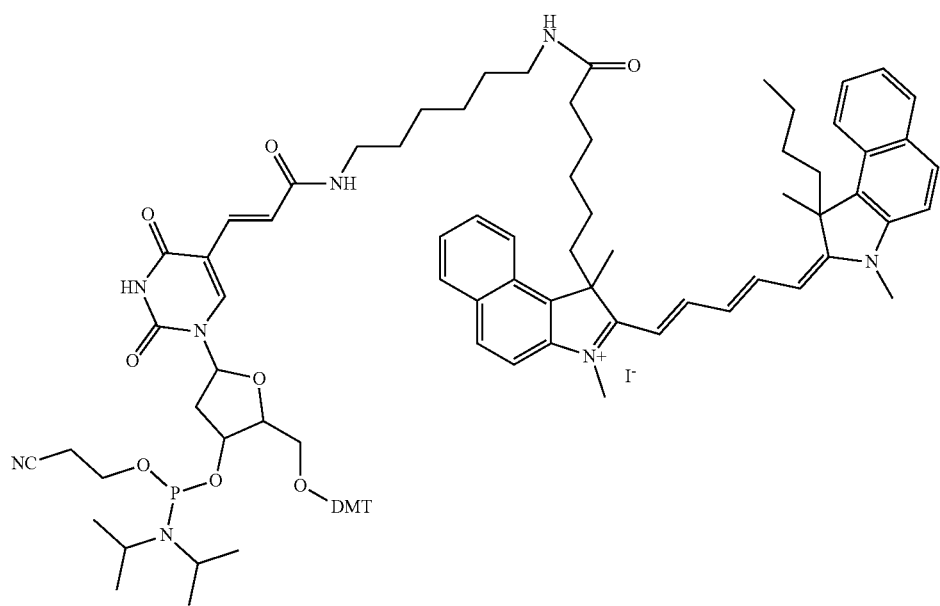
[Compound 45]
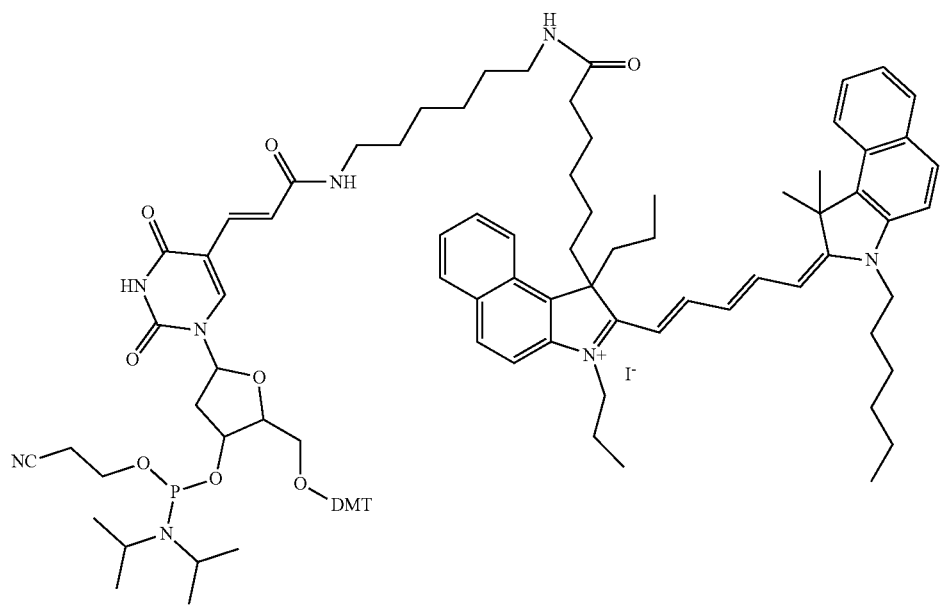

[Compound 46]

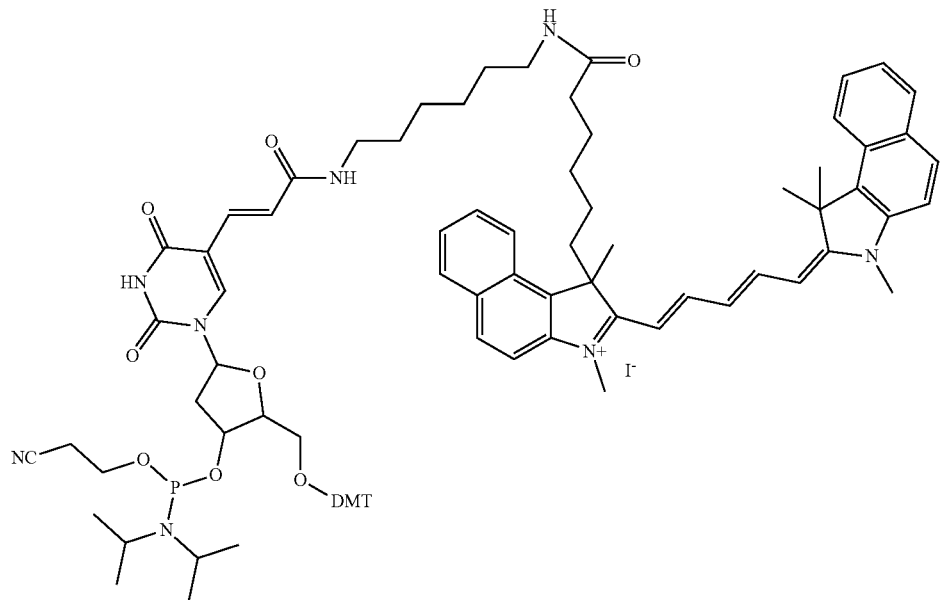

A biomolecule targeted by the reporter represented by Formula 1, 2, or 5 disclosed herein may be at least one selected from an antibody, a lipid, a protein, a peptide, a carbohydrate, a nucleic acid (including DNA, RNA or a nucleotide), and preferably, a nucleic acid (including DNA, RNA or a nucleotide).

Specific examples of lipids include fatty acids, phospholipids, and lipopolysaccharides, and specific examples of carbohydrates include monosaccharides, disaccharides, and polysaccharides (e.g., dextran).

Wherein, a biomolecule may include at least one selected from amino, sulfhydryl, carbonyl, hydroxyl, carboxyl, phosphate and thiophosphate, or a derivative thereof as any functional group of a reporter represented by Formula 1, 2, or 5 or a functional group for reacting with a reactive group binding to the reporter represented by Formula 1, 2, or 5.

In addition, the biomolecule may be an oxy or deoxy polynucleotide which includes at least one selected from amino, sulfhydryl, carbonyl, hydroxyl, carboxyl, phosphate and thiophosphate, or a derivative thereof.

Moreover, in addition to biomolecules, the reporter represented by Formula 1, 2, or 5 may be used to label a drug, a hormone (including a receptor ligand), a receptor, an enzyme or an enzyme substrate, cells, a cell membrane, a toxin, a microorganism or a nano-biomaterial (a polystyrene microsphere, etc.) including at least one selected from amino, sulfhydryl, carbonyl, hydroxyl, carboxyl, phosphate and thiophosphate.

Oligonucleotide, Composition for Detecting Nucleic Acid, and Support for Detecting Nucleic Acid, Including Novel Reporter According to another aspect of the present invention, an oligonucleotide including at least one selected from the reporters represented by Formulas 1, 2, and 5. The oligonucleotide refers to a polymer of one to several hundred nucleotides, and includes all of DNA, RNA, and PNA. In addition, examples of such oligonucleotides include those that can be easily modified by one of ordinary skill in the art, such as analogs thereof, for example, those in which chemical modifications have been applied to the nucleotides, or those in which sugars are linked, and encompasses single-stranded or double-stranded ones.

The oligonucleotide preferably includes a probe. Such a probe is more preferably a probe that is capable of complementarily binding to a target nucleic acid, but the present invention is not limited thereto. Wherein, the probe may be selected from a nucleic acid, a peptide, a saccharide, an oligonucleotide, a protein, an antibody, or a combination thereof, but the present invention is not limited thereto.

In one embodiment, the oligonucleotide may include a quencher. For example, the 5' end of the oligonucleotide may be labeled with the reporter represented by Formula 1, 2, or 5, and the 3' end thereof may be labeled with the quencher. A probe complementarily binding to a target nucleic acid may be located between the 5' end and the 3' end. In addition, the reporter represented by Formula 1, 2, or 5 may also be labeled at an internal site, other than the 5' or 3' end of the oligonucleotide.

The maximum absorbance of the quencher usable in the present invention may be 620 to 700 nm, and preferably, 660 to 680 nm, and the absorbance range of the quencher may be 530 to 730 nm. In addition, the maximum absorbance and absorbance range of the quencher may be appropriately selected considering the fluorescence properties of the reporter defined herein.

It is important that the probe is designed such that the reporter can be sufficiently quenched by the quencher while minimizing signal crosstalk. Accordingly, when designing a probe, depending on the type of target biomolecule (e.g., a nucleic acid), it is necessary to confirm that the reporter and the quencher, which are labeled at the 5' end and the 3' end of the probe, are compatible with each other.

As the quencher, various known or commercially available quenchers (e.g., BHQ0, BHQ1, BHQ2, BHQ3, BBQ650, DABCYL, TAMRA, MGBEclipse, Atto540Q, Atto575Q, Atto612Q, QSY7, and QSY21) may be used. In addition, as the quencher, the quenchers disclosed in Korean Unexamined Patent Application Publication No. 10-2020-0067733 may be used. Representative examples of the quenchers disclosed in Korean Unexamined Patent Application Publication No. 10-2020-0067733 are as follows.

[Quencher 1]
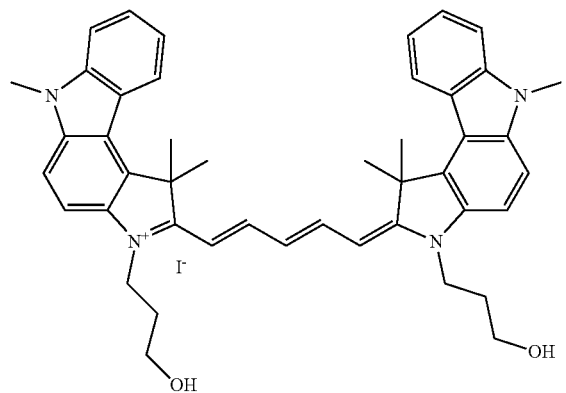
[Quencher 2]
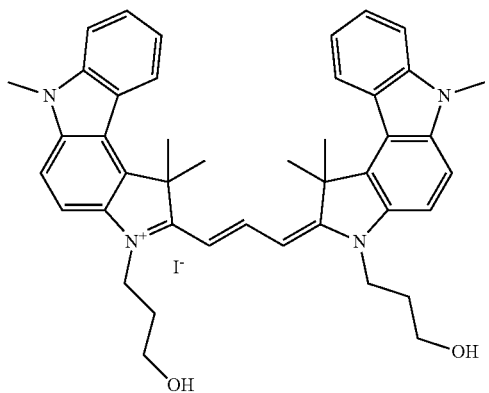
[Quencher 3]
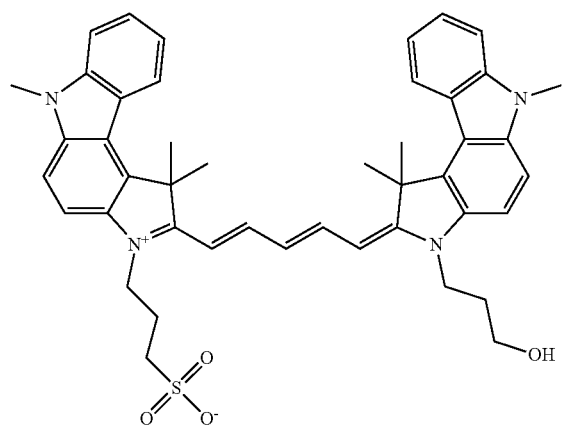
[Quencher 4]
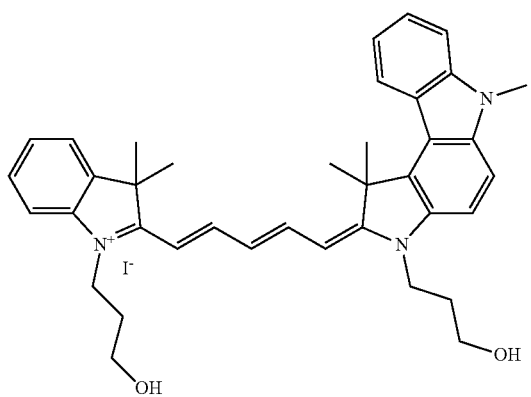
[Quencher 5]
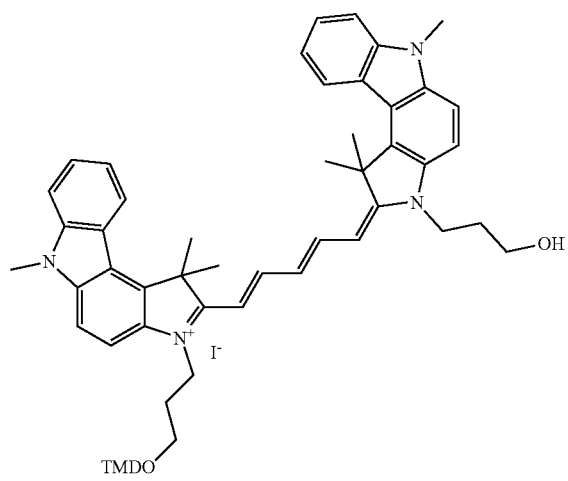
[Quencher 6]
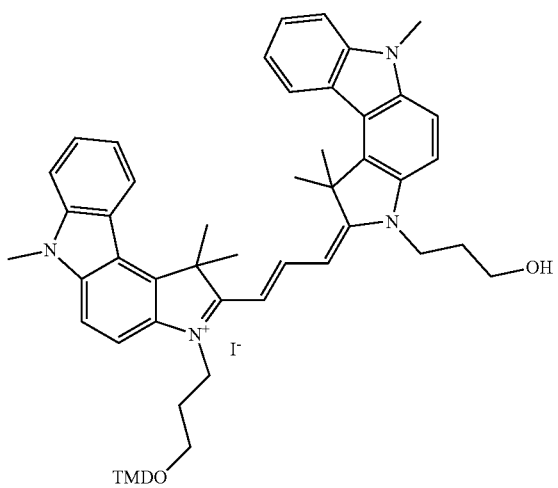

[Quencher 7]

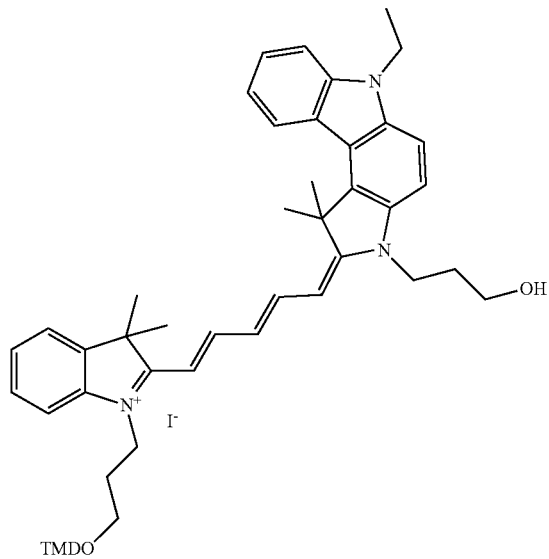

[Quencher 8]

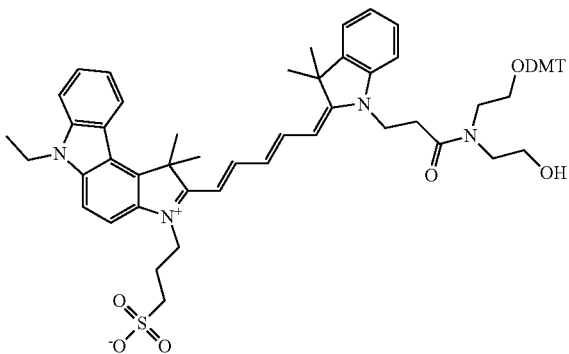

[Quencher 9]

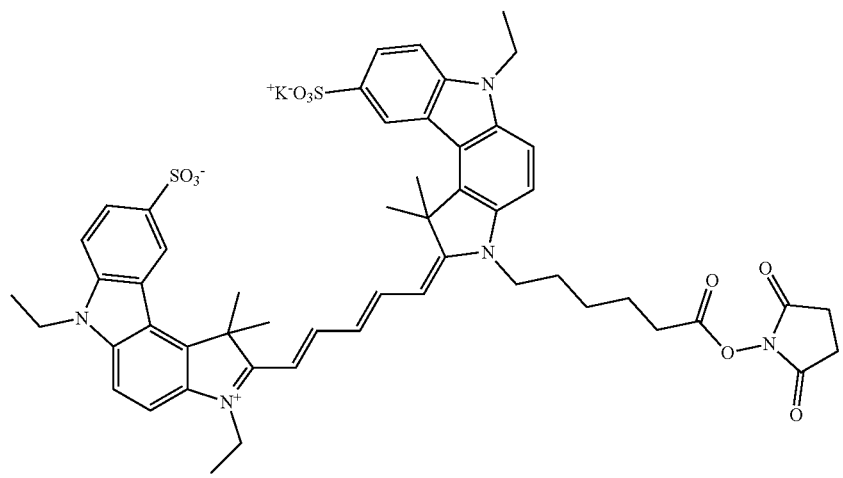

In addition, the oligonucleotide according to the present invention may further include a minor groove binder (MGB) to improve the binding strength to a nucleic acid.

The MGB is a crescent-shaped probe that can selectively bind non-covalently to a minor groove (e.g., shallow furrow in the DNA helix) included in a nucleic acid such as DNA.

Such an oligonucleotide may be used in various ways in the fields of chemistry and biology. Particularly, it may be useful for real-time PCR or a microarray, but the present invention is not limited thereto.

In addition, according to another aspect of the present invention, a composition for detecting a nucleic acid, including the oligonucleotide, is provided.

The composition for detecting a nucleic acid according to one embodiment of the present invention may further include an enzyme, a solvent (buffer, etc.) and other reagents, which are used for a reaction with a target biomolecule, in addition to an oligonucleotide including the reporter represented by Formula 1, 2, or 5, an MGB and a quencher at the same time.

Wherein, as the solvent, a buffer selected from the group consisting of a phosphate buffer, a carbonate buffer and a Tris buffer, an organic solvent selected from dimethyl sulfoxide, dimethylformamide, dichloromethane, methanol, ethanol and acetonitrile, or water may be used, and it is possible to adjust solubility by introducing various functional groups to the reporter according to the type of solvent.

In addition, according to still another aspect of the present invention, a support for detecting a nucleic acid, which includes the reporter represented by Formula 1, 2, or 5, a support, and a linker that connects the reporter and the support, is provided.

Accordingly, a biomolecule in a sample may be fixed on a support matrix through interaction with the reporter fixed on the support.

The support matrix may be manufactured with at least one selected from glass, cellulose, nylon, acrylamide gel, dextran, polystyrene, resin, alginate, collagen, peptides, fibrin, hyaluronic acid, agarose, polyhydroxyethylmethacrylate, polyvinyl alcohol, polyethylene glycol, polyethyleneoxide, polyethylene glycol diacrylate, gelatin, Matrigel, polylactic acid, carboxymethylcellulose, chitosan, latex, and Sepharose, and have a form of beads or a membrane.

As the support, glass, cellulose, nylon, acrylamide gel, dextran, polystyrene or resin may be used, but the present invention is not necessarily limited thereto. Preferably, as the support, controlled pore glass (CPG) or polystyrene, and more preferably, CPG is used.

Wherein, the linker is a part connecting the reporter and the support, and any material capable of connecting the reporter and the support may be used as a linker intended by the present invention.

For example, the linker may be selected from substituted or unsubstituted $C_1$-$C_{30}$ alkyl, substituted or unsubstituted $C_2$-$C_{30}$ heteroalkyl containing at least one hetero atom, substituted or unsubstituted $C_6$-$C_{30}$ aryl, and substituted or unsubstituted $C_3$-$C_{30}$ heteroaryl, and the above-mentioned functional groups may include at least one aminated carboxyl group (or amine group).

Such a linker merely connects a reporter and a support, and does not affect other reactions or the fluorescence and quenching actions of a reporter or fluorophore.

Method of Detecting Nucleic Acid

According to one embodiment of the present invention, a method of labeling a target nucleic acid through a reaction with a reporter-labeled probe or a probe dual-labeled with a reporter and a quencher may be implemented. In addition, a method of labeling a biomolecule using a target-specific interaction by introducing an appropriate reactive group to a reporter according to the type of target biomolecule may be implemented. In addition, a method of identifying the biomolecule labeled with the reporter through electrophoresis may be implemented.

DNA Microarray

A DNA microarray is for measuring the fluorescence of a target nucleic acid by preparing a single-stranded probe nucleic acid which labels a target nucleic acid through a reaction with a dye and has a complementary base sequence to the target nucleic acid, and hybridizing the probe nucleic acid with the target nucleic acid denatured into a single strand on a substrate.

In the labeling method, when gene expression is investigated, as the probe nucleic acid immobilized on the substrate, cDNA, which is prepared by amplifying a cDNA library, genome library, or any of all genomes as a template through PCR, may be used.

In addition, for investigation of gene mutations, various oligonucleotides corresponding to mutations may be synthesized based on a known sequence serving as a reference and used.

A proper method for immobilizing the probe nucleic acid on the substrate may be selected according to the type of nucleic acid or substrate. For example, a method for electrostatic binding to a substrate surface-treated with a cation such as polylysine using the charge of DNA may also be used.

The target nucleic acid denatured into a single strand is immobilized on the substrate, and hybridized with the oligonucleotide. Wherein, the 5' end of the oligonucleotide is labeled with at least one selected from the reporters represented by Formulas 1, 2, or 5, and the 3' end thereof is labeled with a quencher. Between the 5' end and the 3' end, a probe that is able to complimentarily bind to the target nucleic acid may be located.

Hybridization is preferably performed at room temperature to 70° C. for approximately 2 to 48 hours. Through hybridization, a target nucleic acid having a complementary base sequence with the probe nucleic acid is selectively bound to probe nucleic acid. Afterward, the substrate is washed and dried at room temperature.

Wherein, the oligonucleotide is hybridized to the target nucleic acid by the probe, but the fluorophore at the 5' end is present in a quenched state by the quencher at the 3' end.

Subsequently, the oligonucleotide hybridized to the target nucleic acid is elongated by a polymerase, separated from the target nucleic acid due to the exonuclease activity of the polymerase, and degraded. The fluorophore at the 5' end of the oligonucleotide and the quencher at the 3' end thereof are separated from each other, and thus the fluorophore may exhibit fluorescence.

Wherein, the intensity of the generated fluorescence is measured to measure the amplification amount of the target nucleic acid.

PCR Method

According to a PCR method, a probe complementary to the base sequence of a target nucleic acid to be labeled is labeled with a reporter, and reacted with the target nucleic acid before or after the amplification of the target nucleic acid, and then the fluorescence of the target nucleic acid is measured.

Specifically, the elongation reaction of the target nucleic acid is carried out by an enzyme (DNA polymerase or RNA polymerase), and Wherein, a double-stranded nucleic acid sequence formed of the target nucleic acid and a primer consisting of an oligonucleotide is recognized by the enzyme to carry out the elongation reaction from the recognition site, and only a target gene area is amplified.

When synthesis is performed by the enzyme, the synthesis reaction is carried out using nucleotides (dNTP and NTP) as raw materials.

Wherein, by mixing common nucleotides (dNTP and NTP) with reporter-bearing nucleotides in an arbitrary ratio, a nucleic acid into which the equivalent amount of dye is introduced may be synthesized.

In addition, a nucleic acid into which a reporter is introduced may be synthesized by bonding the reporter after introducing nucleotides having an amino group in an arbitrary ratio by PCR.

When synthesis is performed by the enzyme, the synthesis reaction is carried out using nucleotides as raw materials, and Wherein, when a material in which the 3' OH of the nucleotide is substituted with His used, a nucleic acid is no longer elongated, and at this point of time, the reaction ends.

This nucleotide, that is, dideoxynucleotide triphosphate (ddNTP) is called a terminator.

When a terminator is mixed with common nucleotides to synthesize a nucleic acid, the terminator is introduced with a certain probability to end the reaction, so nucleic acids of various lengths are synthesized.

When the above are separated by size through gel electrophoresis, DNA is lined up in order of length. Wherein, when labeled with a different reporter for each type of terminator base, at the end point (3' end) of the synthesis reaction, a dependency on each base is observed, and by reading fluorescence information starting with the reporter attached to the terminator, base sequence information of the target nucleic acid may be obtained.

In addition, instead of the terminator, primers previously labeled with the reporter may be used for hybridization with a target nucleic acid.

In addition, as a probe, a peptide nucleic acid (PNA) may also be used. PNA is obtained by replacing the pentose phosphate backbone, which is the basic skeleton of a nucleic acid, with a polyamide backbone composed of glycine as a unit, and PNA has a 3D structure highly similar to nucleic acids, and is very specific for a nucleic acid having a complementary base sequence and strongly binds thereto.

Accordingly, PNA may also be used as a reagent for telomere research by applying a telomere PNA probe, in addition to a conventional DNA analysis method such as in-situ hybridization (ISH).

For labeling, for example, double-stranded DNA is brought into contact with PNA having a base sequence complementary to all or a part of the base sequence of the DNA and labeled with a reporter for hybridization, the mixture is heated to generate single-stranded DNA, and slowly cooled to room temperature to prepare a PNA-DNA complex, and then fluorescence is measured.

In the above example, a method of amplifying a target nucleic acid through PCR and measuring the fluorescence of a product has been described, but in this method, it is necessary to identify the size of the product through electrophoresis and then investigate the amount of amplification product by measuring fluorescence intensity.

To this end, the amount of product may be measured in real time using the energy transfer of a fluorescent dye and a probe designed to generate fluorescence by hybridizing it to the PCR product.

For example, DNA labeled with a donor and an acceptor may be used. A specific labeling method may be a molecular beacon method, a TaqMan-PCR method, or a cycling probe method, which is used to confirm the presence of a nucleic acid having a specific sequence.

Other Labeling Methods

In addition, the reporter of the present invention may also be used in a method of labeling a target using specific binding.

That is, in the labeling of a sample including a target or a sample modified by a modifying material, one of a binding material specifically binding to the sample and a binding material specifically binding to the modifying material may be labeled with a reporter, and fluorescence may be measured from the labeled binding materials.

Wherein, for the combination of the sample or modifying material with the binding material, antigen-antibody, hapten-anti-hapten antibody, biotin-avidin, a Tag antigen, a Tag antibody, lectin-glycoprotein, or hormone-receptor may be used.

Specifically, a specific antigen may be labeled through antigen-specific interaction of an antibody by reacting a binding material such as a reporter-labeled antibody with an antigen present in a substrate, solution, beads, or an antibody.

An antigen may be a protein, a polysaccharide, a nucleic acid, or a peptide, and other than the antigen, a hapten such as a low-molecular-weight molecule, for example, FITC or a dinitrophenyl group may also be used. Wherein, as an antigen (or hapten)-antibody combination, there are GFP and anti-GFP antibodies, FITC and anti-FITC antibodies and the like.

Labeled antigens may be used in various measurement methods including immunostaining, ELISA, Western blotting or flow cytometry.

In addition, an intracellular signaling phenomenon may be observed using the reporter of the present invention. Various enzymes are involved in internal signaling or cell responses according to the signaling. In a representative signaling phenomenon, it is known that a special protein kinase is activated, thereby inducing protein phosphorylation to initiate signaling.

Binding and hydrolysis of a nucleotide (e.g., ATP or ADP) play a critical role in its activity, and an intracellular signaling phenomenon may be observed with high sensitivity by introducing a reporter into a nucleotide derivative.

In addition, the reporter of the present invention may also be used in observation of a gene expression phenomenon using RNA interference (RNAi).

RNAi is inhibition of expression by degradation of mRNA of a target gene by introducing double-stranded RNA (dsRNA) into cells, and thus it is possible to observe the RNAi phenomenon by labeling designed dsRNA with a reporter.

In addition, since the reporter of the present invention has a reactive group capable of labeling a target nucleic acid or target protein in tissue or cells, it may be used as a dye for confirming the transcription level of a target nucleic acid or the expression level of a target protein.

Hereinafter, specific examples of the present invention are presented. However, the following examples are only for exemplifying or explaining the present invention in detail, and the present invention is not limited thereto. In addition, among the reporters defined in the claims and detailed description of the present invention, compounds whose synthesis methods are not disclosed through the following preparation examples may be synthesized with reference to the following preparation examples.

Preparation Example 1

(1) Synthesis of Compound 1

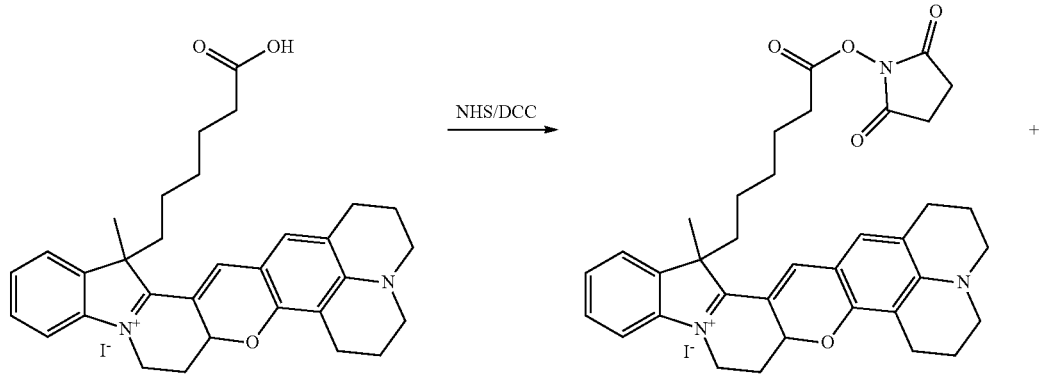

-continued
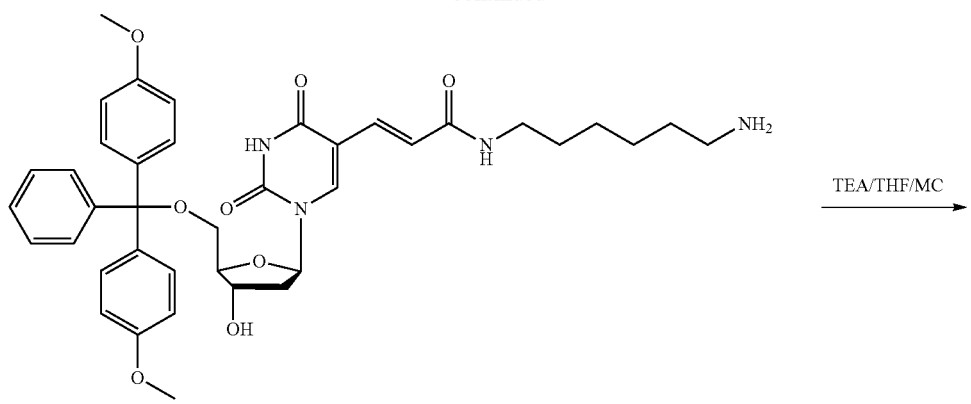
3
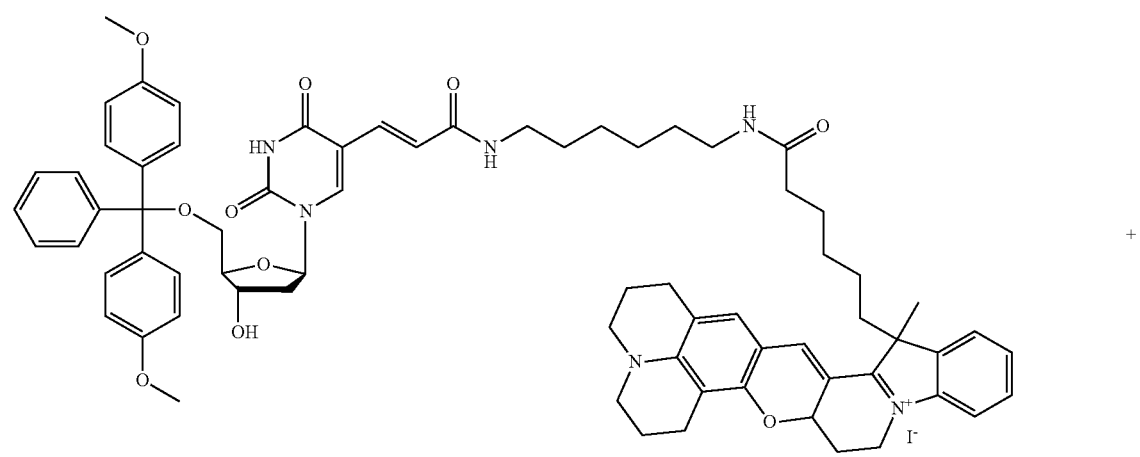
4
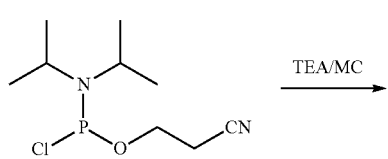
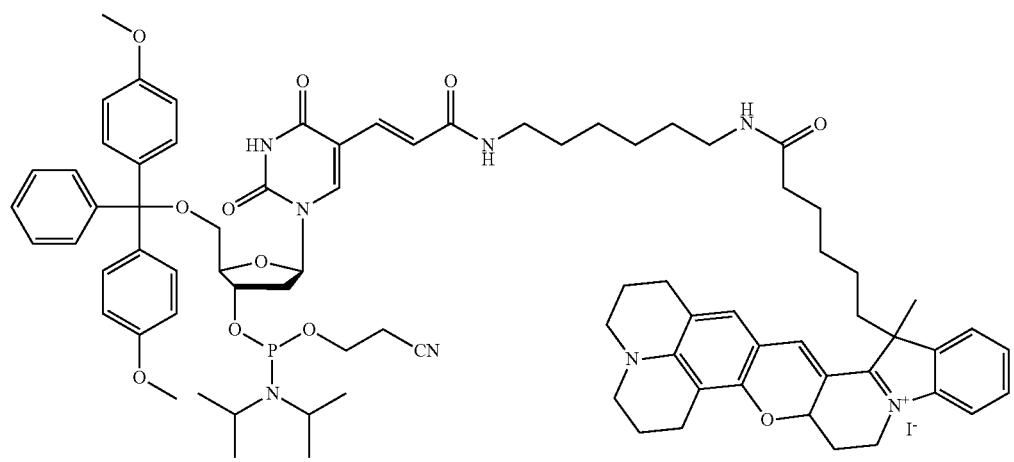
6
compound 1

Synthesis of Intermediate 2

Intermediate 1 (synthesized with reference to Korean Unexamined Patent Application Publication No. 10-2017-0009795) (30 g, 0.048 mol), N-hydroxysuccinimide (6.63 g, 0.058 mol), N,N'-dicyclohexylcarbodiimide (11.89 g, 0.058 mol), and dichloromethane (600 mL) were put into a reactor and stirred at room temperature for 2 hours, and the resulting solid was filtered and the filtrate was concentrated.

Synthesis of Intermediate 4

Intermediate 2 (15 g, 0.021 mol), Intermediate 3 (synthesized with reference to International laid-open Patent Application Publication No. 2016-100401) (17.4 g, 0.025 mol), triethylamine (7.2 mL, 0.052 mol), tetrahydrofuran (300 mL), and dichloromethane (300 mL) were put into a reactor and stirred at room temperature for 1.5 hours. An aqueous sodium bicarbonate solution was put into the reactor and stirred vigorously and then the organic layer was separated. After adding sodium sulfate to the organic layer and stirring, the solid was filtered, and the filtrate was concentrated and purified by column chromatography.

Synthesis of Compound 1

Intermediate 4 (8 g, 0.006 mol), 2-cyanoethyl N,N-diisopropylchlorophosphoamidite (4.06 g, 0.017 mol), triethylamine (5.0 ml, 0.037 mol), and dichloromethane (160 mL) were put into a reactor and stirred at room temperature for 1.5 hours. After adding water to the reactor and stirring vigorously, the organic layer was separated. After adding sodium sulfate to the organic layer and stirring, the solid was filtered and the filtrate was concentrated and purified by column chromatography.

$^1$H-NMR of the obtained Compound 1 is as follows.

$^1$H NMR (400 MHZ, CDCl$_3$) δ 7.93-7.73 (m, 2H), 7.44-7.21 (m, 14H), 7.07-6.97 (m, 3H), 6.86-6.85 (m, 4H), 6.70-6.60 (m, 1H), 6.31 (br t, 1H), 5.75-5.71 (m, 1H), 5.53-5.46 (m, 1H), 4.53-4.15 (m, 4H), 3.77-3.11 (m, 18H), 2.69-2.62 (m, 6H), 2.44-1.95 (m, 9H), 1.47-1.05 (m, 34H), 0.94-0.80 (m, 1H), 0.70-0.50 (m, 1H), (2) Synthesis of Compound 2

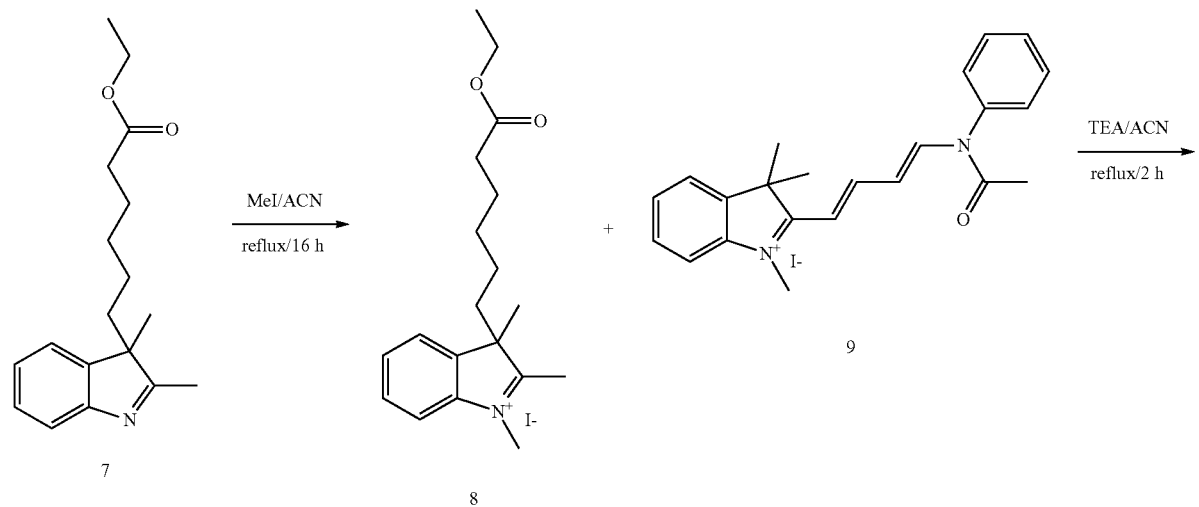

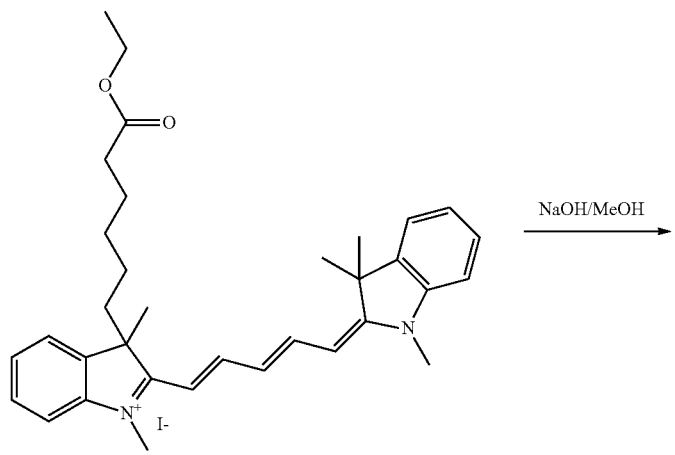

-continued
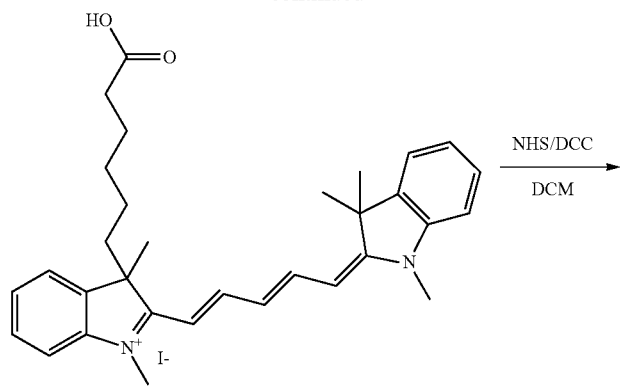
11
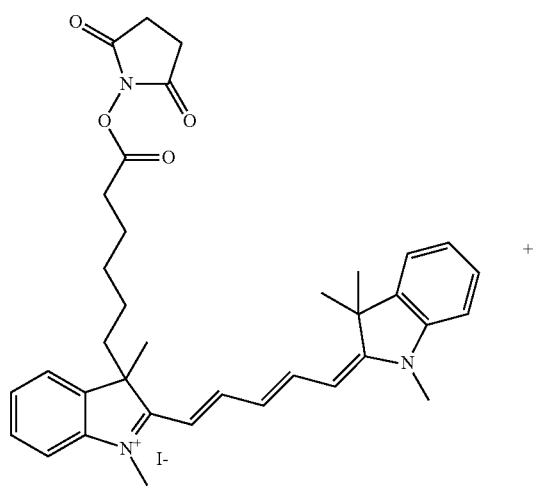
12
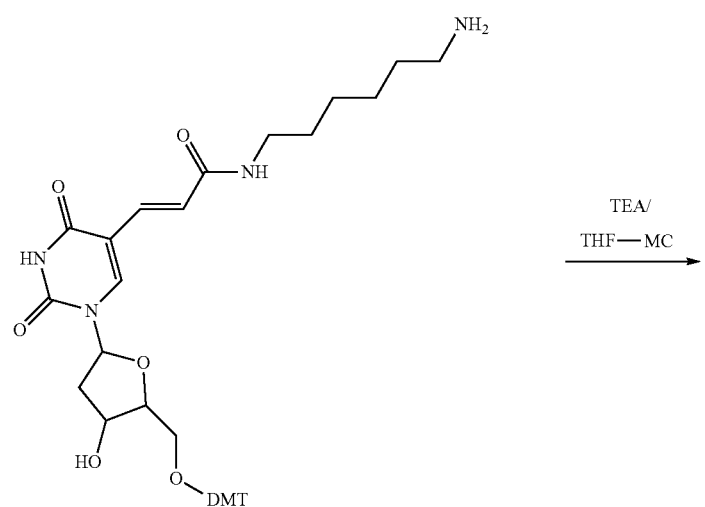
3

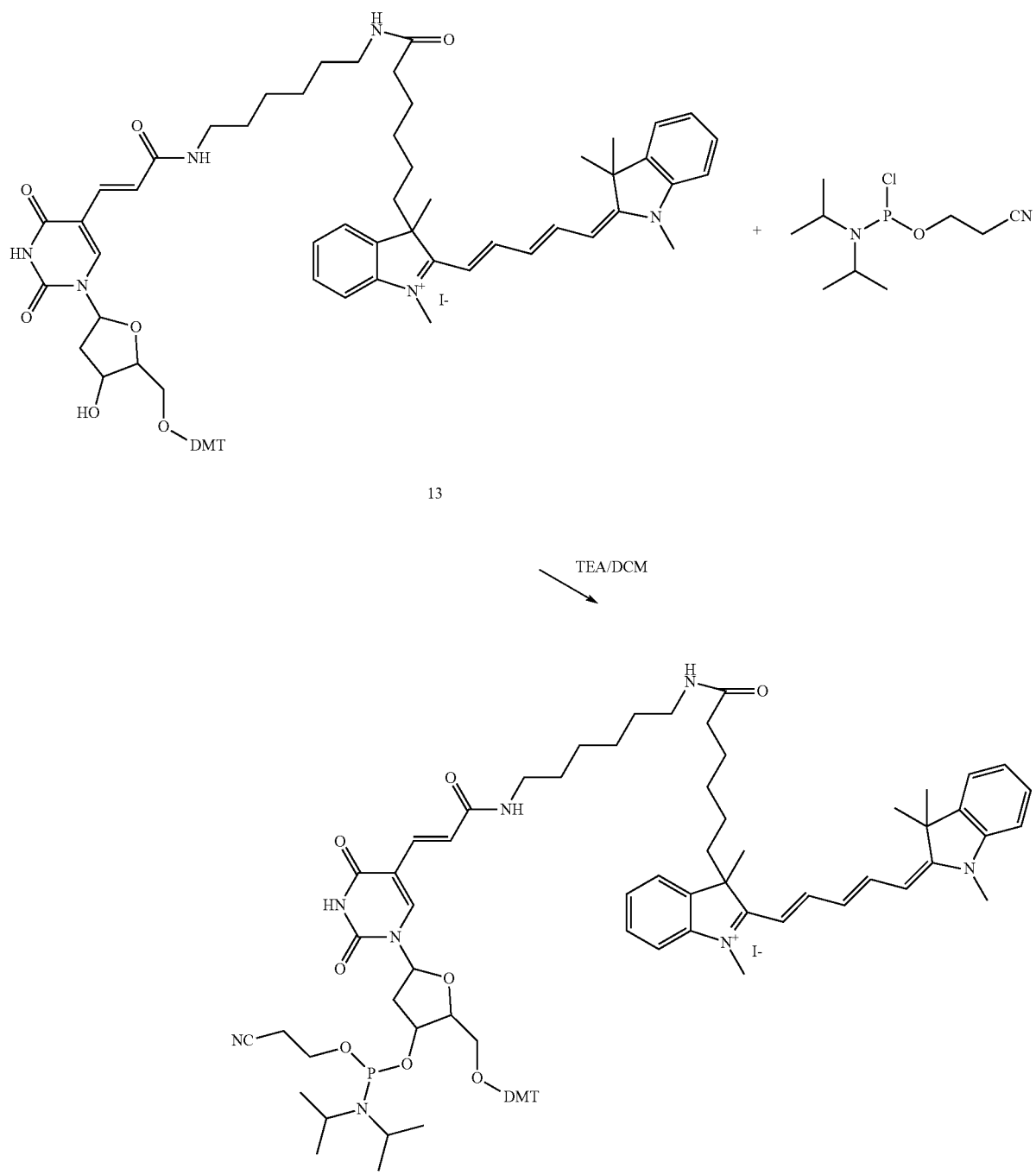

Synthesis of Intermediate 8

Intermediate 7 (synthesized with reference to International laid-open Patent Application Publication No. 2017-010852X (40.0 g, 0.139 mol), methyl iodide (39.5 g, 0.278 mol), and acetonitrile (400 mL) were put into a reactor, and stirred for 16 hours under reflux. After cooling, the resulting solid was filtered.

Synthesis of Intermediate 10

Intermediate 8 (54.5 g, 0.127 mol), Intermediate 9 (synthesized with reference to US Patent Publication No. 5760201) (50 g, 0.105 mol), triethyl amine (73.7 ml, 529.0 mol), and acetonitrile (500 mL) were put into a reactor, stirred for 2 hours under reflux and then concentrated and purified by column chromatography.

Synthesis of Intermediate 11

Intermediate 10 (40 g, 0.062 mol), a 1N sodium hydroxide solution (630 mL), tetrahydrofuran (400 mL), and methanol (400 mL) were put into a reactor and stirred at room temperature for 16 hours. The reaction solution was acidified with hydrochloric acid and concentrated, and then extracted with dichloromethane. Sodium sulfate was added to the organic layer, stirred, filtered, and then the filtrate was concentrated and purified by column chromatography.

Synthesis of Intermediate 12

Intermediate 12 was synthesized in the same manner as in Synthesis of Intermediate 2.

Synthesis of Intermediate 13

Intermediate 13 was synthesized in the same manner as in Synthesis of Intermediate 4.

Synthesis of Compound 2

Compound 2 was synthesized in the same manner as in Synthesis of Compound 1.

$^1$H-NMR of the obtained Compound 2 is as follows.

$^1$H NMR (400 MHZ, CDCl$_3$) δ 8.14 (t, 2H), 7.93-7.88 (m, 1H), 7.44-7.03 (m, 19H), 7.06 (d, 1H), 6.85-6.83 (m, 4H), 6.74-6.59 (m, 3H), 6.31-6.17 (m, 3H), 5.39-5.30 (m, 1H), 4.54 (br t, 1H), 4.18 (m, 1H), 3.76-3.40 (m, 16H), 3.33-3.07 (m, 4H), 2.64-2.41 (m, 6H), 2.11 (t, 3H), 1.74-1.70 (m, 8H), 1.31-1.04 (m, 16H), 0.94-0.80 (m, 1H), 0.60-0.40 (m, 1H)

(3) Synthesis of Compound 3

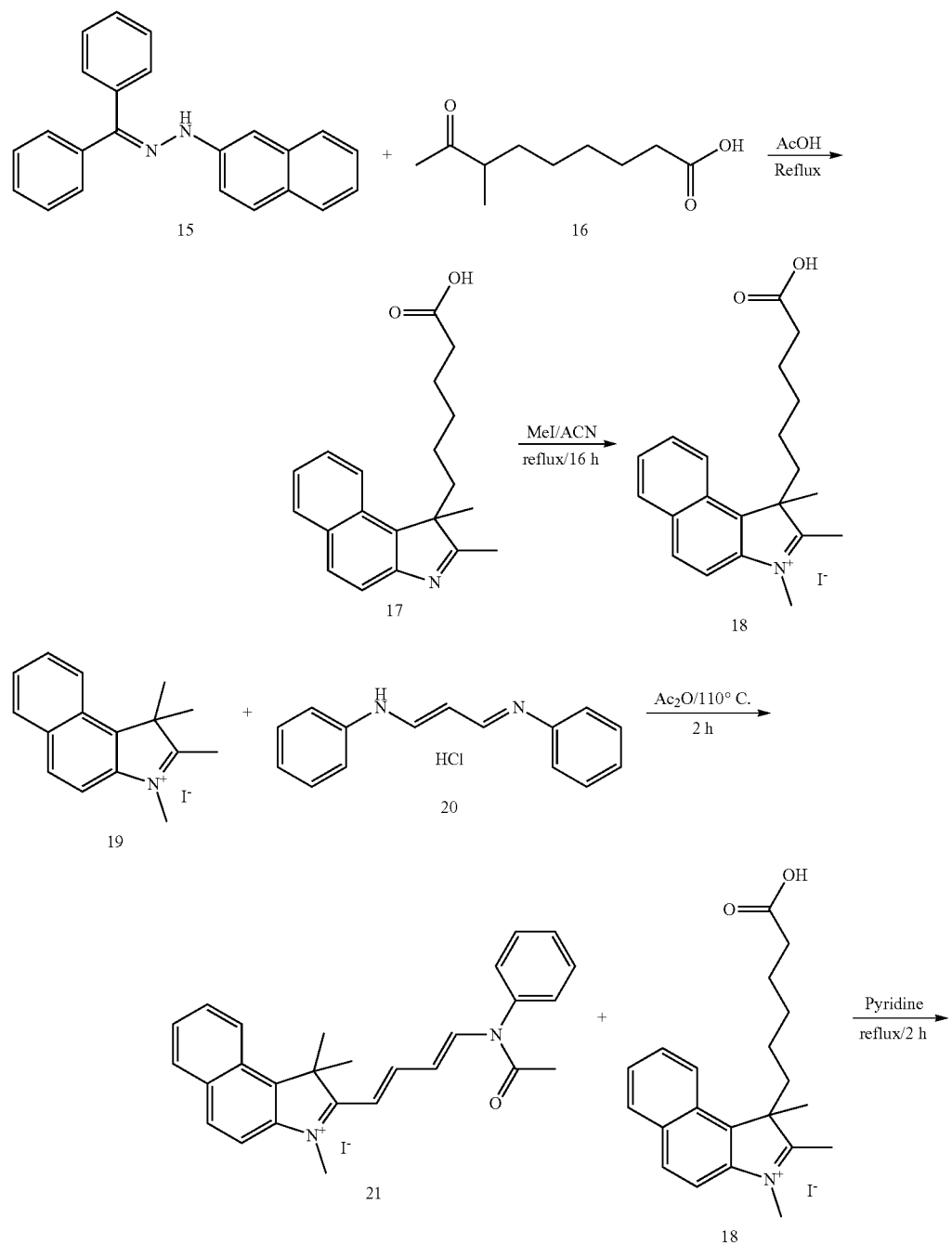

-continued
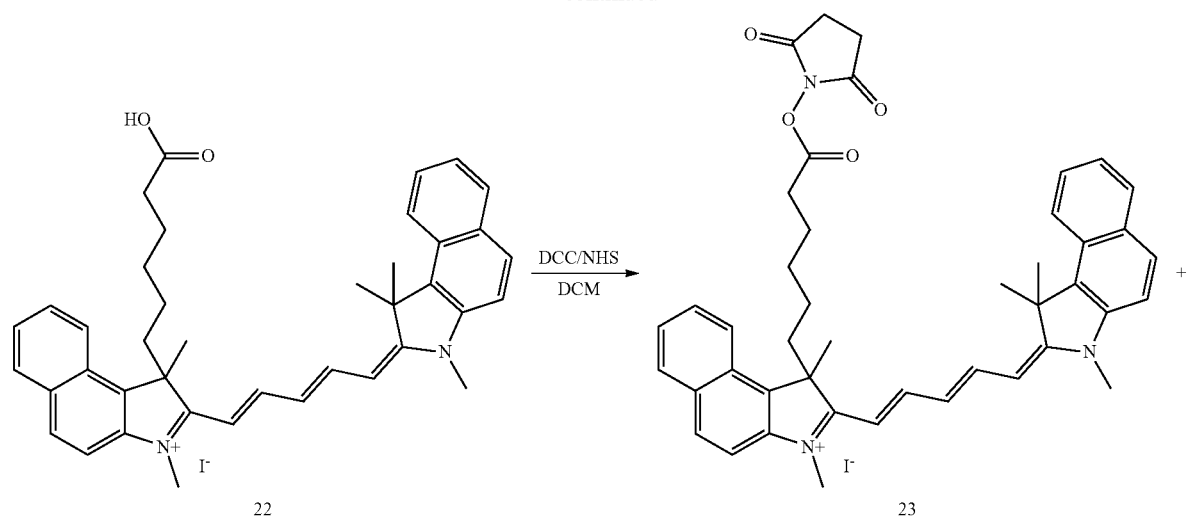
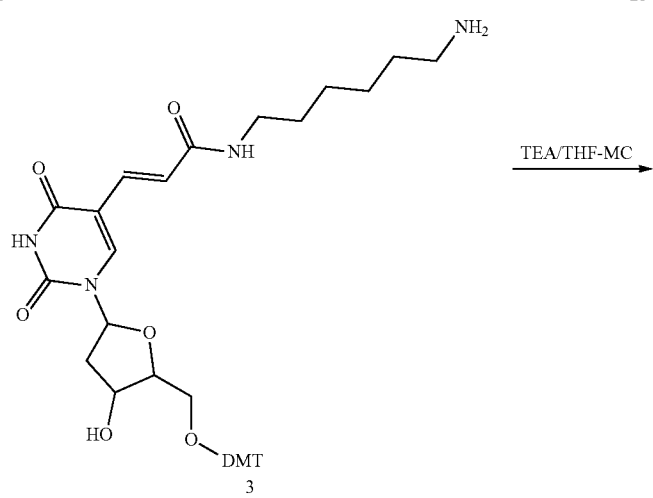
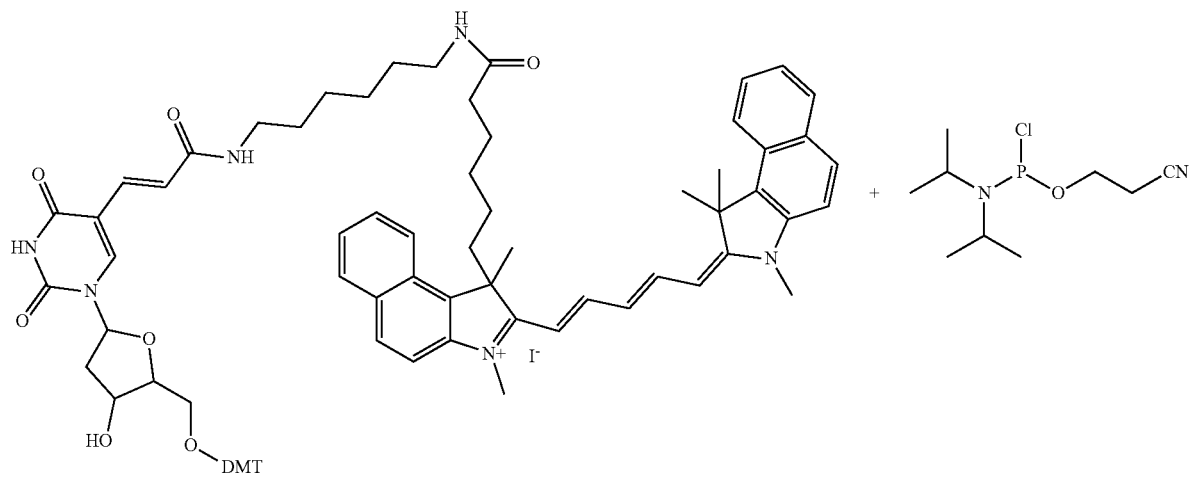

-continued

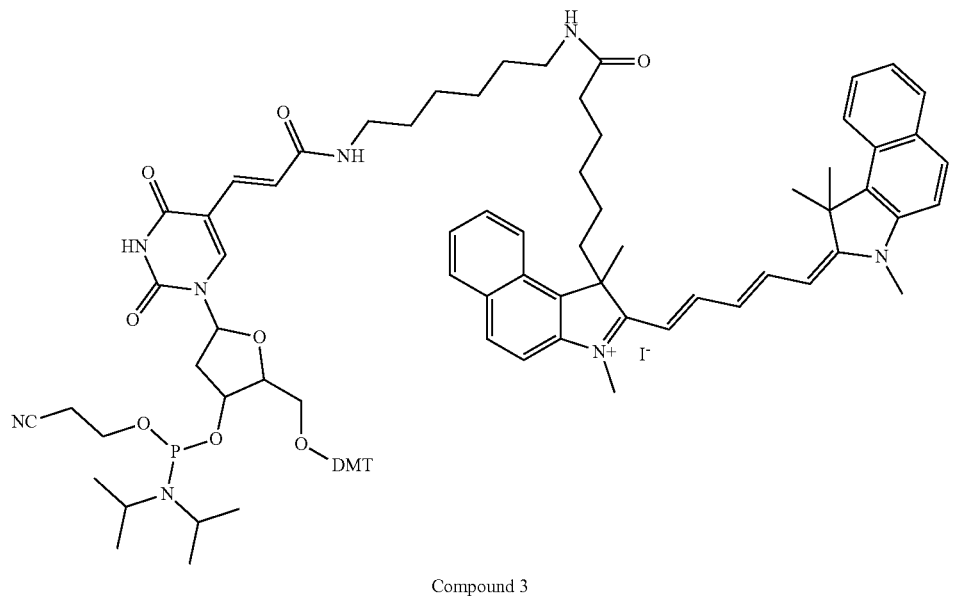

Compound 3

Synthesis of Intermediate 17

Intermediate 15 (synthesized with reference to International Patent Application Publication No. 2017-010852) (35 g, 108.0 mol), Intermediate 16 (synthesized with reference to European Patent Application Publication No. 1209205) (22.24 g, 119.0 mol), and citric acid (250 mL) were put into a reactor, stirred for 3 days under reflux, and then concentrated and purified by column chromatography.

Synthesis of Intermediate 18

Intermediate 18 was synthesized in the same manner as in Synthesis of Intermediate 8.

Synthesis of Intermediate 21

Intermediate 19 (synthesized with reference to Organic & Biomolecular Chemistry (2015), 13 (30), 8169-8172) (164.6 g, 0.468 mol), Intermediate 20 (133.0 g, 0.515 mol), and acetic anhydride (1.6 L) were put into a reactor and stirred at 110° C. for 2 hours. After cooling, the reaction solution was added to ethyl ether (6 L) and stirred vigorously, and the resulting solid was filtered.

Synthesis of Intermediate 22

Intermediate 18 (17.9 g, 0.039 mol), Intermediate 21 (24.9 g, 0.047 mol), and pyridine (180 mL) were put into a reactor, stirred at 70° C. for 4 hours and then concentrated and purified by column chromatography.

Synthesis of Intermediate 23

Intermediate 23 was synthesized in the same manner as in Synthesis of Intermediate 2.

Synthesis of Intermediate 24

Intermediate 24 was synthesized in the same manner as in Synthesis of Intermediate 4.

Synthesis of Compound 3

Compound 3 was synthesized in the same manner as in Synthesis of Compound 1.

$^1$H-NMR of the obtained Compound 3 is as follows.

$^1$H NMR (400 MHZ, CDCl$_3$) δ 8.38 (t, 2H), 8.15 (t, 2H), 7.95-7.93 (m, 4H), 7.62-7.61 (m, 2H), 7.50-7.22 (m, 16H), 7.06 (d, 1H), 6.85-6.83 (m, 4H), 6.61 (t, 1H), 6.51-6.20 (m, 5H), 5.31-5.22 (m, 1H), 4.54 (br t, 1H), 4.18 (m, 1H), 3.83 (s, 3H), 3.78-3.76 (m, 9H), 3.64-3.40 (m, 4H), 3.20-3.06 (m, 4H), 2.64-2.30 (m, 6H), 2.07-1.98 (m, 11H), 1.26-1.05 (m, 16H), 0.94-0.80 (m, 1H), 0.60-0.40 (m, 1H),

Preparation Example 2. Synthesis of Single-Labeled Probe (Oligonucleotide)

A single-labeled oligonucleotide in which Compound 1, 2 or 3 as a reporter was labeled at the 5' end was synthesized using the MerMade™ 48xDNA Synthesizer and Universal UnyLinker Support (Chemgene, 500 Å) as CPG. The sequence of the single-labeled oligonucleotide is shown in Table 1 below.

TABLE 1

| Classification | Sequence |
| --- | --- |
| SLP1 | 5'-Compound 1-dt-TTT TTT TTT T-3' |
| SLP2 | 5'-Compound 2-dt-TTT TTT TTT T-3' |
| SLP3 | 5'-Compound 3-dt-TTT TTT TTT T-3' |

After synthesis, the single-labeled oligonucleotide was deprotected and purified by RP-HPLC. After purification, the absorption and emission spectra of the synthesized single-labeled oligonucleotide were measured. The result of measuring the maximum absorption/emission wavelengths of Compounds 1 to 3 (an error rate of less than 0.1%) is shown in Table 2 below.

TABLE 2

| Reporter | Excitation$_{max}$ (nm) | Emission$_{max}$ (nm) |
|---|---|---|
| Compound 1 | 602 | 628 |
| Compound 2 | 647 | 674 |
| Compound 3 | 689 | 716 |

Preparation Example 3. Synthesis of Dual-Labeled Probe (Oligonucleotide)

Using the Universal UnyLinker Support (Chemgene, 500 Å), each of 5'-ATG CAA CAT TAA CCC GAG ATA CG-3' as a forward primer and 5'-ACT CGG CTT GGG AAG AGC TT-3' as a reverse primer for *Chlamydia trachomatis* (CT) was synthesized at 1 μmol scale and purified by HPLC.

The dual-labeled probe is a CT-selective labeled probe, and 5'-TTG TCC ATA TCT TTG ATA CGA CGC CGC-quencher-3' was synthesized using [Quencher 7]-attached CPG (synthesized with reference to Korean Unexamined Patent Application Publication No. 10-2020-0067733) and CPG to which Black Hole Quenchers 2 and 3 (BHQ2 and BHQ3, LGC Biosearch Technologies), which are commercially available quenchers, are attached, and then dual-labeled probes labeled with Compound 1, 2, or 3 were synthesized as reporters at 1 μmol scale each and then subjected to HPLC purification.

The forms of the synthesized dual-labeled probes are shown in Table 3 below, and the absorption wavelength ranges of Quencher 7, BHQ2, and BHQ3, used as the quenchers of the dual-labeled probes, are shown in Table 4 below.

TABLE 3

| Classification | Sequence |
|---|---|
| DLP1 | 5'-Compound 1-dT-TTGTCCATATCT TTGATACGACGCCGC-Quencher 7-3' |
| DLP2 | 5'-Compound 2-dT-TTGTCCATATCT TTGATACGACGCCGC-Quencher 7-3' |
| DLP3 | 5'-Compound 3-dT-TTGTCCATATCT TTGATACGACGCCGC-Quencher 7-3' |
| DLP4 | 5'-Compound 1-dT-TTGTCCATATCT TTGATACGACGCCGC-BHQ2-3' |
| DLP5 | 5'-Compound 2-dT-TTGTCCATATCT TTGATACGACGCCGC-BHQ2-3' |
| DLP6 | 5'-Compound 3-dT-TTGTCCATATCT TTGATACGACGCCGC-BHQ3-3' |

TABLE 4

| Classification | $\lambda_{Max}$ (nm) | ε (mol$^{-1}$ · cm$^{-1}$) |
|---|---|---|
| Quencher 7 | 580~710 | 140,000 |
| BHQ2 | 550~650 | 38,000 |
| BHQ3 | 620~730 | 42,000 |

The structure of the Quencher 7-attached CPG used in Preparation Example 3 is as follows.

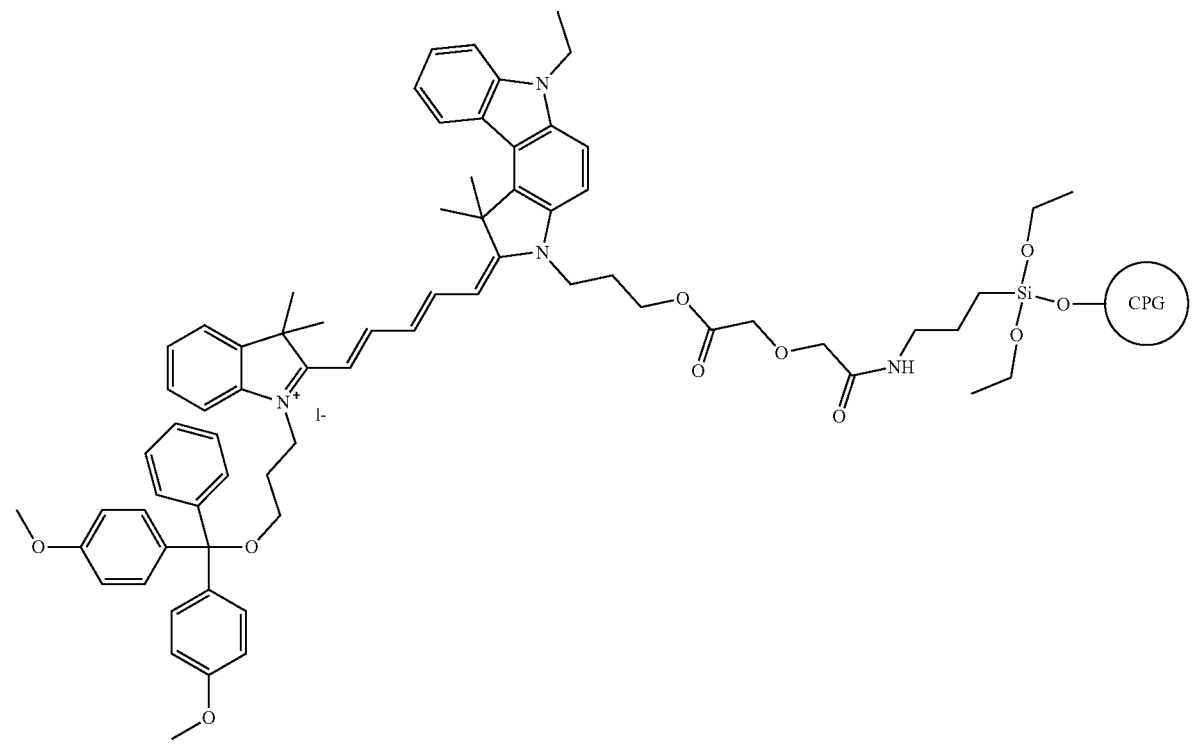

Experimental Example 1. Real-Time PCR Experiment Using Dual-Labeled Probe

Real-Time PCR was repeatedly performed twice on CT plasmid DNA using each dual-labeled probe synthesized according to Preparation Example 3 with the composition shown in Table 5 (using CFX-96, Biorad). The real-time PCR results are shown in FIGS. 1 and 2.

TABLE 5

| Classification | Content (µl) |
| --- | --- |
| (Bioline)SensiFAST ™ Probe No-ROX Mix (2X) | 10 |
| CT plasmid DNA ($5 \times 10^6$, $5 \times 10^4$, $5 \times 10^3$ copies/µl) | 1 |
| CT F/R primer mix (10 pmole/µl) | 1 |
| CT Dual-labeled probe (7 pmole/µl) | 3 |
| Pure Water | 5 |

Figure 2:
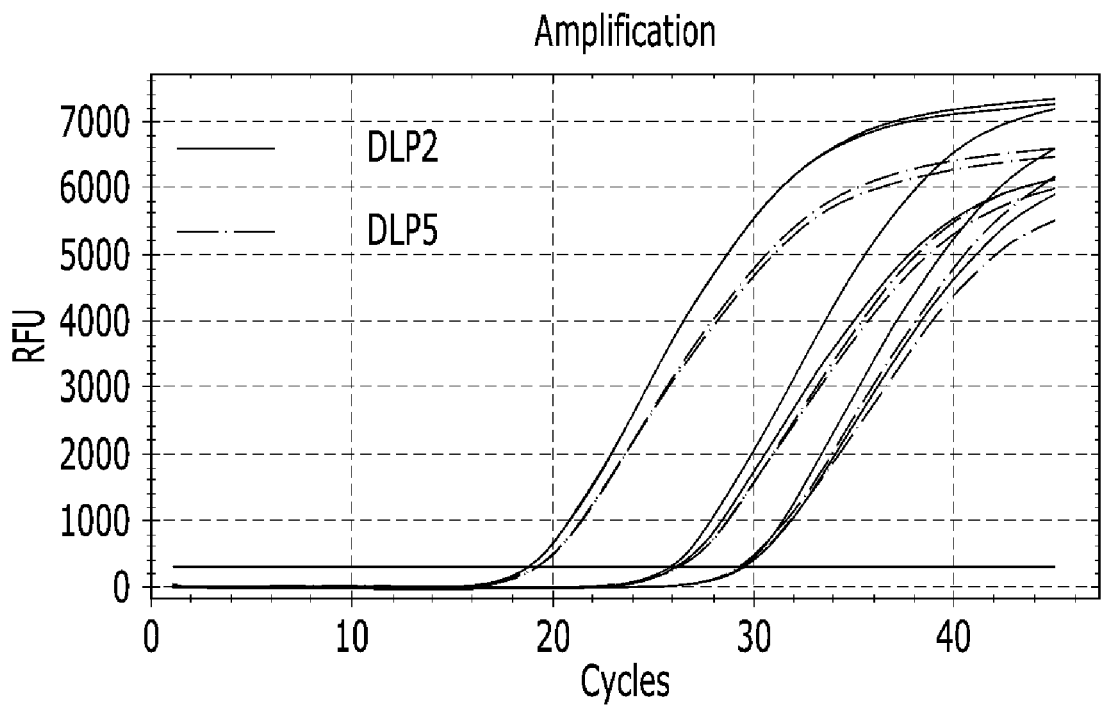
FIG. 2 is a graph showing the result of real-time PCR repeated twice on a CT target sequence using a dual-labeled probe with DLP2 and DLP5.
Figure 3:
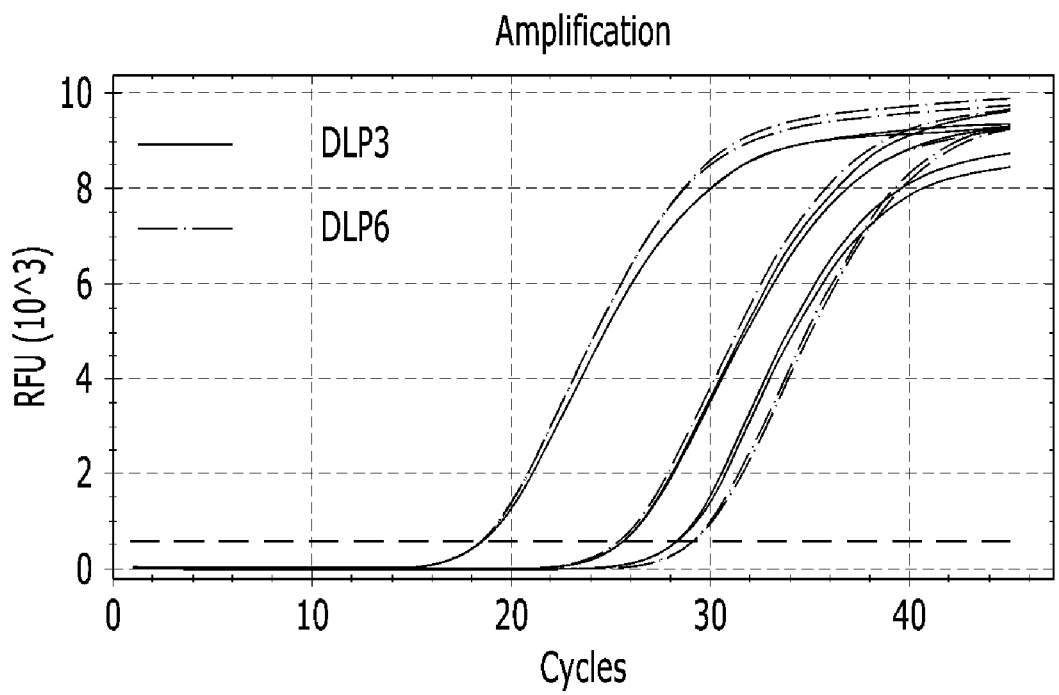
FIG. 3 is a graph showing the result of real-time PCR repeated twice on a CT target sequence using a dual-labeled probe with DLP3 and DLP6.
Figure 4:
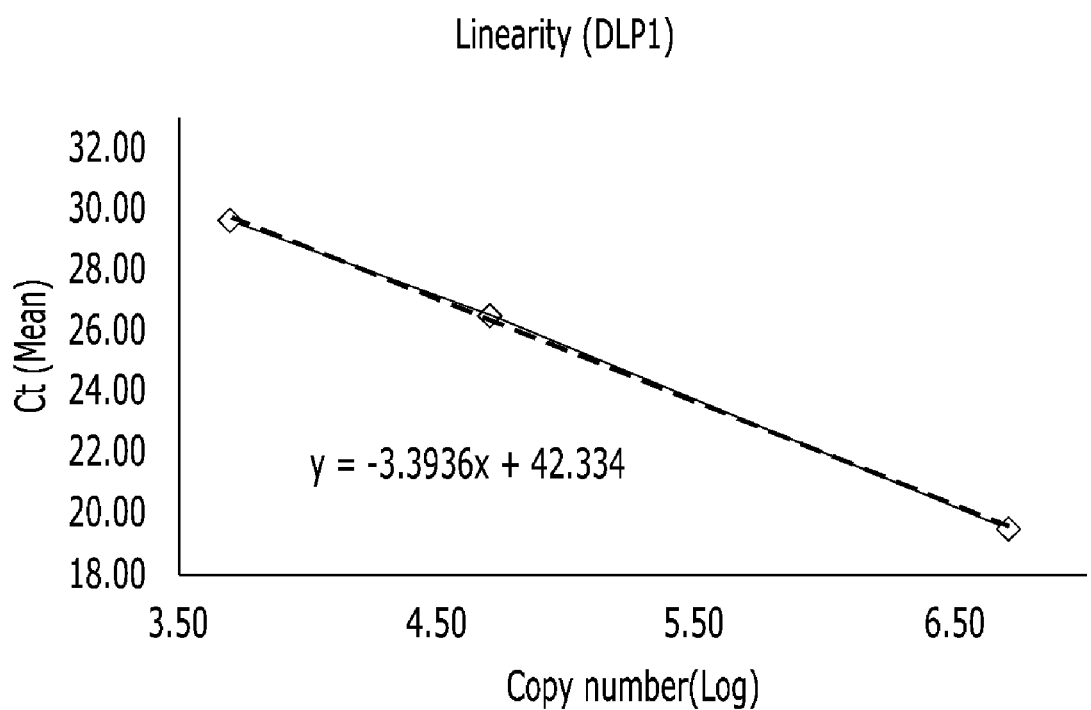
FIGS. 4 to 9 show the results (linearity) of real-time PCR using a dual-labeled probe with DLP1 to DLP6, respectively.
Figure 5:
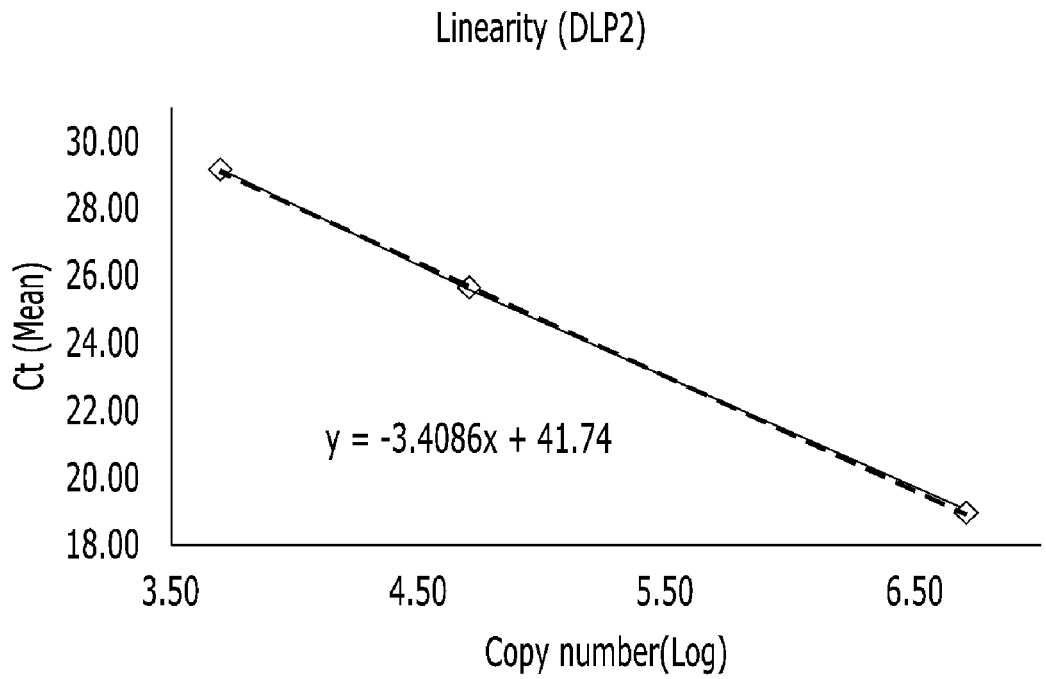
Figure 6:
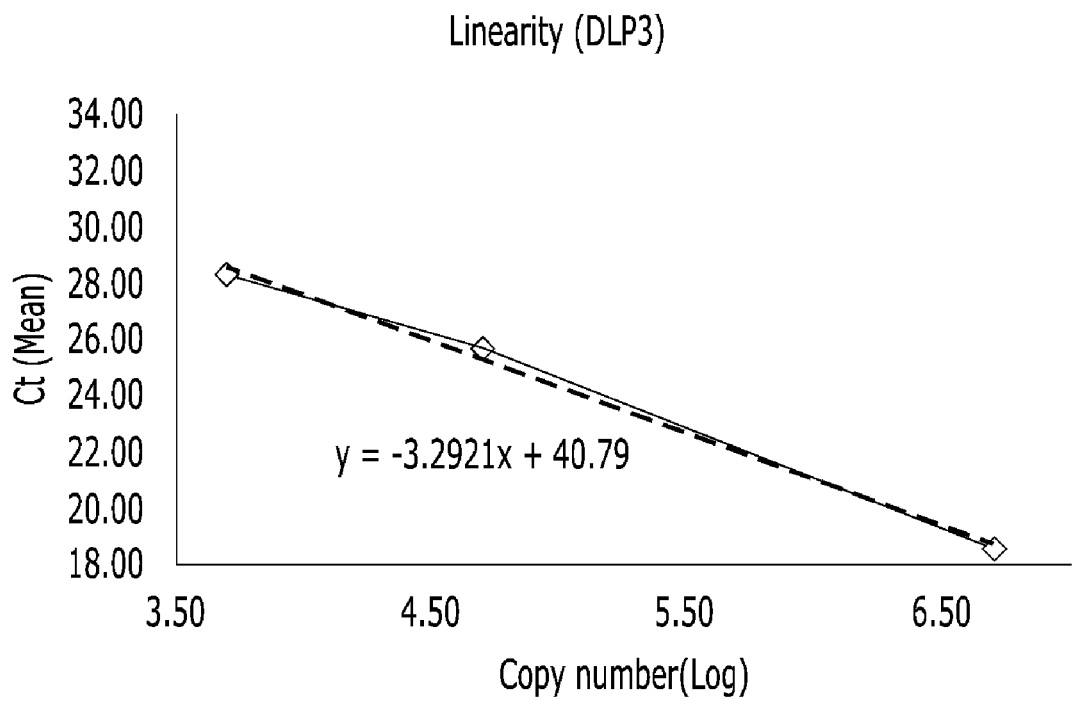
Figure 7:
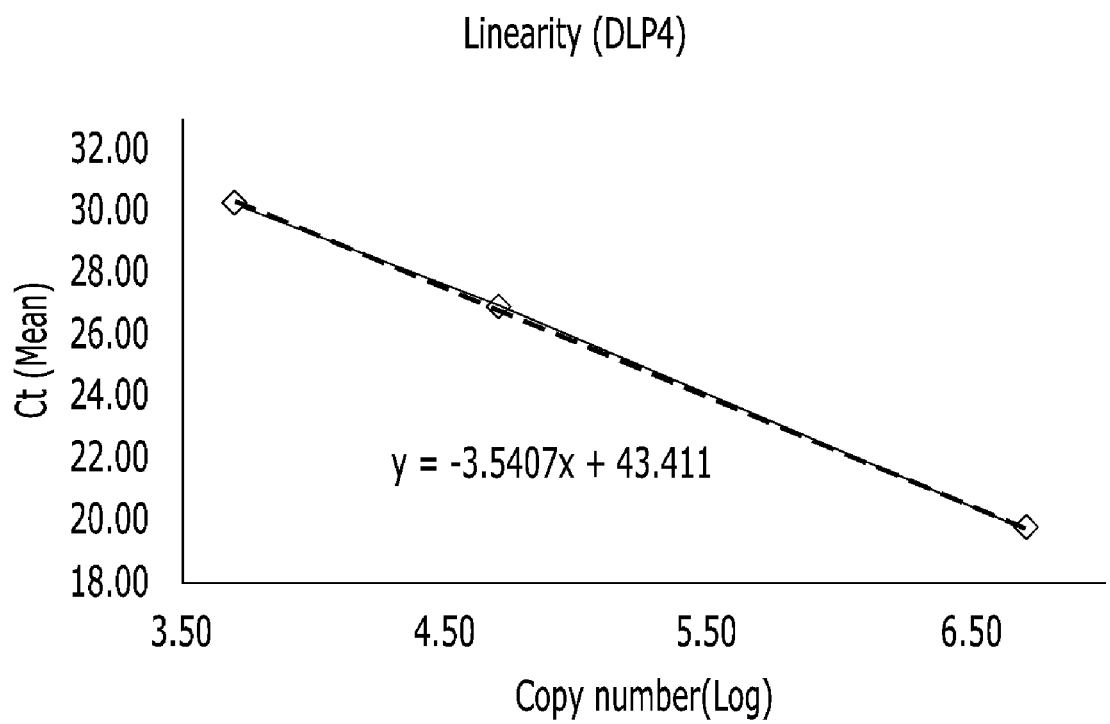
Figure 8:
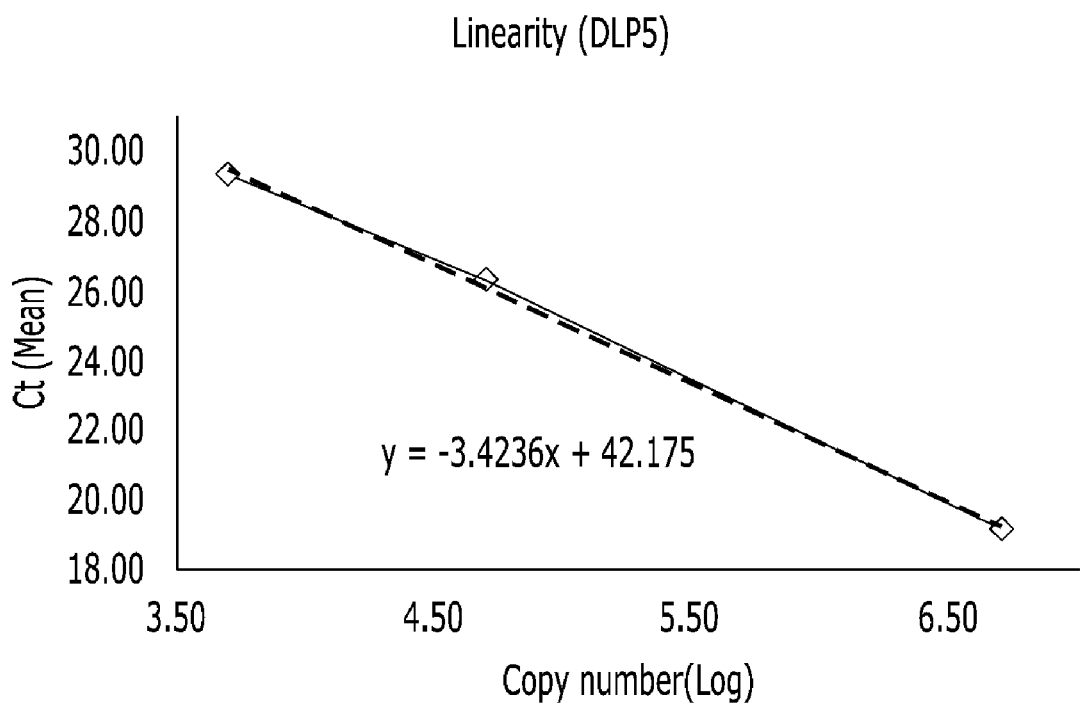
Figure 9:
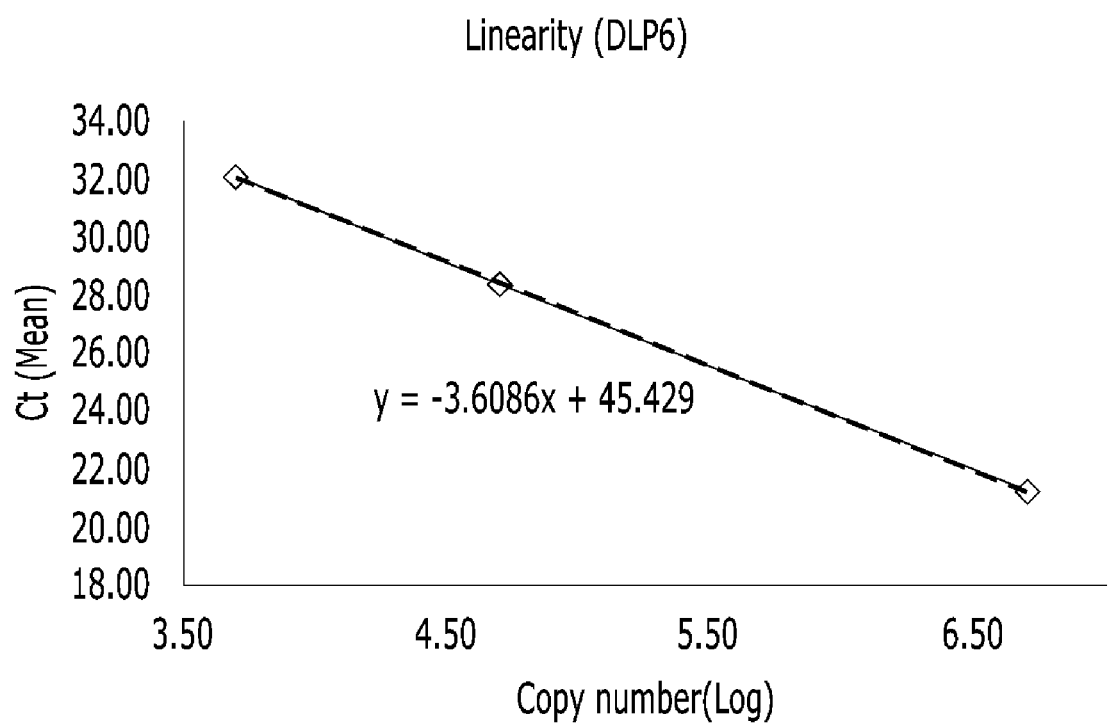

Referring to FIGS. 1 to 3 showing the real-time PCR results, compared with DLP4 to DLP6 using commercially-available BHQ2 or BHQ3 as one of the quenchers of Compounds 1 to 3, it can be seen that DLP 1 to DLP3 using Quencher 7 show relatively low Ct values, and the final fluorescence amplification intensity is improved approximately 5 to 10%.

Considering the limit of detection (LoD) of molecular diagnostics dealing with 1 to 2 copies of DNA or RNA contained in bacteria or viruses, when Compounds 1 to 3 are used as reporters, it can be expected that the ease of detecting the target will be improved by using Quencher 7 as a quencher.

In addition, referring to FIGS. 4 to 9, it can be confirmed that Compounds 1 to 3 as reporters for labeling a nucleic acid defined herein exhibit excellent linearity not only for commercially available quencher BHQ2 or BHQ3 but also for Quencher 7.

Accordingly, the reporter for labeling a nucleic acid defined herein is expected to be sufficiently used to label not only CT nucleic acids but also various nucleic acids, and it can be seen that the reporter for labeling a nucleic acid defined herein can also be easily applied to existing commercially available quenchers without separate technical modifications.

Meanwhile, it is known that most existing, commercially-available reporters for labeling a nucleic acid have limitations in that substitutions can only be made at the 5' end. On the other hand, as the reporter for labeling a nucleic acid defined herein has a substituted form at dT, substitution can be made not only at the 5' end but also internal position of the sequence and thus can be contributed to improve the intensity of fluorescence amplification by closely adjusting the distance between a reporter and a quencher.

Although embodiments of the present invention have been described above, it will be understood by those of ordinary skill in the art that the present invention may be modified and altered in various ways by adding, altering, or deleting a component without departing from the spirit of the present invention defined in the appended claims, and such modifications and alterations are also be included in the scope of the present invention.

What is claimed is:

1. A reporter for labeling a nucleic acid represented by Formula 5 below:

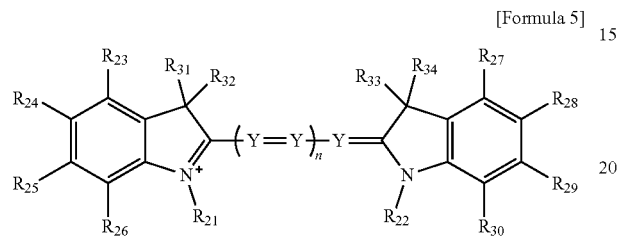

[Formula 5]

wherein, $R_{21}$ and $R_{22}$ are each independently selected from hydrogen, deuterium, substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, substituted or unsubstituted $C_2$-$C_{20}$ heterocycloalkyl, substituted or unsubstituted $C_5$-$C_{20}$ aryl, and substituted or unsubstituted $C_2$-$C_{20}$ heteroaryl, $R_{23}$ to $R_{30}$ are each independently a functional group selected from hydrogen, deuterium, substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, substituted or unsubstituted $C_2$-$C_{20}$ heterocycloalkyl, hydroxy, oxido (—O⁻), substituted or unsubstituted $C_1$-$C_{10}$ alkoxy, substituted or unsubstituted $C_3$-$C_{20}$ cycloalkyloxy, substituted or unsubstituted $C_5$-$C_{20}$ aryloxy, substituted or unsubstituted $C_2$-$C_{20}$ heteroaryloxy, substituted or unsubstituted $C_5$-$C_{20}$ aryl, substituted or unsubstituted $C_2$-$C_{20}$ heteroaryl, substituted or unsubstituted $C_5$-$C_{20}$ aralkyl, substituted or unsubstituted $C_1$-$C_{10}$ alkylthio, substituted or unsubstituted $C_5$-$C_{20}$ arylthio, substituted or unsubstituted $C_3$-$C_{20}$ cycloalkylthio, substituted or unsubstituted $C_2$-$C_{20}$ heteroarylthio, substituted or unsubstituted acylamino, acyloxy, substituted or unsubstituted phosphino, trifluoromethylsulfonyl (—SO$_2$CF$_3$), substituted or unsubstituted ammonium, nitro, substituted sulfonyl, substituted sulfonic acid ester, substituted or unsubstituted sulfonamide, substituted thioketone, trihalomethyl (—CF$_3$, —CCl$_3$, —CBr$_3$, or —CI$_3$), haloformyl (—COCl, —COBr, or —COI), formyl (—CHO), acyl, substituted ester, substituted or unsubstituted aminocarbonyl, nitro, nitroso (—N=O), fluoro (—F), chloro (—Cl), bromo (—Br), iodo (—I), substituted or unsubstituted germanium, substituted or unsubstituted boron, substituted or unsubstituted aluminum, substituted or unsubstituted silyl, substituted or unsubstituted amide, carbamate, substituted or unsubstituted phosphine, nitrile, hydrazine, acetal, ketal, polyalkyleneoxide, and -$L_1$-$R_{12}$, or two adjacent functional groups are bonded to each other to form a ring, $R_{31}$ to $R_{34}$ are each independently selected from hydrogen, deuterium, substituted or unsubstituted $C_1$-$C_{10}$ alkyl, substituted or unsubstituted $C_1$-$C_{10}$ heteroalkyl containing at least one hetero atom, and -$L_1$-$R_{12}$, and at least one of $R_{31}$ to $R_{34}$ is -$L_1$-$R_{12}$, $L_1$ includes a single bond or at least one selected from substituted or unsubstituted $C_1$-$C_{10}$ alkyl, substituted or unsubstituted $C_1$-$C_{10}$ heteroalkyl containing at least one hetero atom, substituted or unsubstituted $C_2$-$C_{10}$ alkenyl, substituted or unsubstituted $C_2$-$C_{10}$ alkynyl, substituted or unsubstituted $C_3$-$C_{20}$ cycloalkyl, substituted or unsubstituted $C_3$-$C_{20}$ cycloalkenyl, and substituted or unsubstituted $C_2$-$C_{20}$ heterocycloalkyl, and $R_{12}$ is a deoxyribonucleoside represented by Formula 3 below,

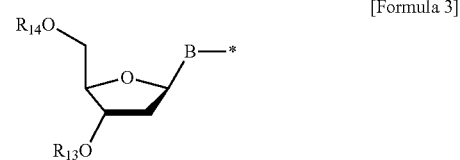

[Formula 3]

Wherein,

* indicates a location where the deoxyribonucleoside is bonded to $L_1$,

B is a nucleobase, $R_{13}$ is selected from hydrogen, deuterium, P(OR$_{15}$)(N(R$_{16}$R$_{17}$), and -$L_2$-$R_{18}$, $R_{14}$ is an alcohol protecting group, hydrogen or P(OR$_{15}$)(N(R$_{16}$R$_{17}$), or a support or nucleic acid to which the reporter is bound, at least one of $R_{13}$ and $R_{14}$ is P(OR$_{15}$)(N(R$_{16}$R$_{17}$), $R_{15}$ to $R_{17}$ are each independently selected from hydrogen, deuterium, substituted or unsubstituted $C_1$-$C_{10}$ alkyl, and substituted or unsubstituted $C_1$-$C_{10}$ heteroalkyl containing at least one hetero atom, $L_2$ is a single bond, or selected from an internucleotide phosphodiester bond, substituted or unsubstituted $C_1$-$C_{10}$ alkyl and substituted or unsubstituted $C_1$-$C_{10}$ heteroalkyl containing at least one hetero atom, $R_{18}$ is hydroxy or P(OR$_{15}$)(N(R$_{16}$R$_{17}$), or a support or nucleic acid to which the reporter is bound, Y is CR$_{35}$, each $R_{35}$ is selected from hydrogen, deuterium, substituted or unsubstituted $C_1$-$C_{10}$ alkyl, substituted or unsubstituted $C_1$-$C_{10}$ heteroalkyl containing at least one hetero atom, fluoro (—F), chloro (—Cl), bromo (—Br), and iodo (—I), and n is an integer of 1 to 4, when any functional group of $R_{21}$ to $R_{35}$ is a substituted functional group, any substituent other than hydrogen bonded to at least one carbon of the functional group, wherein the substituent is selected from deuterium, $C_1$-$C_{10}$ alkyl, $C_1$-$C_{10}$ heteroalkyl containing at least one hetero atom, $C_2$-$C_{10}$ alkenyl, $C_2$-$C_{10}$ alkynyl, $C_3$-$C_{20}$ cycloalkyl, $C_3$-$C_{20}$ cycloalkenyl, $C_2$-$C_{20}$ heterocycloalkyl, hydroxy, oxido (—O⁻), $C_1$-$C_{10}$ alkoxy, $C_3$-$C_{20}$ cycloalkyloxy, $C_5$-$C_{20}$ aryloxy, $C_2$-$C_{20}$ heteroaryloxy, $C_5$-$C_{20}$ aryl, $C_2$-$C_{20}$ heteroaryl, $C_5$-$C_{20}$ aralkyl, $C_1$-$C_{10}$ alkylthio, $C_5$-$C_{20}$ arylthio, $C_3$-$C_{20}$ cycloalkylthio, $C_2$-$C_{20}$ heteroarylthio, acylamino, acyloxy, phosphino, trifluoromethylsulfonyl (—$SO_2CF_3$), ammonium, nitro, substituted sulfonyl, substituted sulfonic acid ester, sulfonamide, substituted thioketone, trihalomethyl (—$CF_3$, —$CCl_3$, —$CBr_3$, or —$CI_3$), haloformyl (—COCl, —COBr, or —COI), formyl (—CHO), acyl, substituted ester, aminocarbonyl, nitro, nitroso (—N=O), fluoro (—F), chloro (—Cl), bromo (—Br), iodo (—I), germanium, boron, aluminum, silyl, amide, carbamate, phosphine, nitrile, hydrazine, acetal, ketal, polyalkyleneoxide, and -$L_1$-$R_{12}$.

2. The reporter of claim 1, wherein $L_1$ is a linker including at least one carbon, and any carbon of the linker is a carbonyl carbon.

3. The reporter of claim 1, wherein $R_{12}$ is a deoxyribonucleoside represented by Formula 4 below:

[Formula 4]

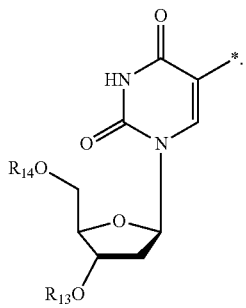

4. An oligonucleotide, comprising:
the reporter according to claim 1; and
a quencher.

5. The oligonucleotide of claim 4, further comprising:
a minor groove binder (MGB) interposed between the reporter and the quencher.

6. A composition for detecting a nucleic acid, comprising the oligonucleotide of claim 4.

7. A support for detecting a nucleic acid, comprising:
the reporter of claim 1;
a support; and
a linker connecting the reporter and the support, through any position of the compound of Formula 3.

8. The support of claim 7, wherein the support is glass, cellulose, nylon, acrylamide gel, dextran, polystyrene, or resin.

9. A method of detecting a nucleic acid, comprising:
(a) preparing a reaction mixture including a target nucleic acid, a reagent required for amplifying the target nucleic acid, and the oligonucleotide of claim 4;
(b) amplifying the target nucleic acid in the reaction mixture through polymerase chain reaction; and
(c) measuring a fluorescence intensity of the reaction mixture.

10. The method of claim 9, wherein (b) includes
(b-1) elongating the oligonucleotide hybridized to the target nucleic acid by a polymerase;
(b-2) separating the reporter and the quencher of the oligonucleotide from the target nucleic acid by the exonuclease activity of the polymerase; and
(b-3) allowing the reporter separated from the quencher to emit fluorescence.

11. The method of claim 9, further comprising:
(d) measuring an amplification amount of the target nucleic acid from the fluorescence intensity measured in (c).

12. An oligonucleotide, comprising:
the reporter according to claim 1.

* * * * *

SEQUENCE LISTING

```
Sequence total quantity: 4
SEQ ID NO: 1            moltype = DNA  length = 10
FEATURE                 Location/Qualifiers
misc_feature            1..10
                        note = oligonucleotide for a single-labeled oligonucleotide
                        in Preparation Example 2
source                  1..10
                        mol_type = other DNA
                        organism = synthetic construct
SEQUENCE: 1
ttttttttt                                                                        10

SEQ ID NO: 2            moltype = DNA  length = 23
FEATURE                 Location/Qualifiers
misc_feature            1..23
                        note = forward primer for synthesis of dual-labeled probe
                        in Preparation Example 3
source                  1..23
                        mol_type = other DNA
                        organism = synthetic construct
SEQUENCE: 2
atgcaacatt aacccgagat acg                                                        23

SEQ ID NO: 3            moltype = DNA  length = 20
FEATURE                 Location/Qualifiers
misc_feature            1..20
                        note = reverse primer for synthesis of dual-labeled probe
                        in Preparation Example 3
source                  1..20
                        mol_type = other DNA
                        organism = synthetic construct
SEQUENCE: 3
actcggcttg ggaagagctt                                                            20

SEQ ID NO: 4            moltype = DNA  length = 27
FEATURE                 Location/Qualifiers
misc_feature            1..27
                        note = oligonucleotide for a dual-labeled oligonucleotide
                        in Preparation Example 3
```

```
source          1..27
                mol_type = other DNA
                organism = synthetic construct
SEQUENCE: 4
ttgtccatat ctttgatacg acgccgc                                              27
```